United States Patent
Nishimura et al.

(10) Patent No.: US 9,206,125 B2
(45) Date of Patent: Dec. 8, 2015

(54) USE OF COMPOUND BINDING TO MSIN3B THAT SPECIFICALLY BINDS TO NEURON RESTRICTIVE SILENCER FACTOR (NRSF)

(75) Inventors: Yoshifumi Nishimura, Yokohama (JP); Aritaka Nagadoi, Yokohama (JP); Yuuka Hirao, Yokohama (JP); Yoshio Goshima, Yokohama (JP); Naoya Yamashita, Yokohama (JP); Naoki Miyata, Nagoya (JP); Takayoshi Suzuki, Nagoya (JP); Ryuta Hiraishi, Nagoya (JP); Hiroshi Ueda, Nagasaki (JP)

(73) Assignees: PUBLIC UNIVERSITY CORPORATION YOKOHAMA CITY UNIVERSITY, Kanagawa (JP); NAGASAKI UNIVERSITY, Nagasaki (JP); NAGOYA CITY UNIVERSITY, Aichi (JP)

( * ) Notice: Subject to any disclaimer, the term of this patent is extended or adjusted under 35 U.S.C. 154(b) by 0 days.

(21) Appl. No.: 13/578,230

(22) PCT Filed: Feb. 9, 2011

(86) PCT No.: PCT/JP2011/052710
§ 371 (c)(1),
(2), (4) Date: Sep. 24, 2012

(87) PCT Pub. No.: WO2011/099502
PCT Pub. Date: Aug. 18, 2011

(65) Prior Publication Data
US 2013/0203738 A1    Aug. 8, 2013

(30) Foreign Application Priority Data
Feb. 10, 2010    (JP) .................................. 2010-027066

(51) Int. Cl.
| | | |
|---|---|---|
| *C07D 211/16* | (2006.01) | |
| *C07D 211/14* | (2006.01) | |
| *C07D 211/10* | (2006.01) | |
| *C07C 233/65* | (2006.01) | |
| *A61K 31/445* | (2006.01) | |
| *C07D 211/96* | (2006.01) | |

(Continued)

(52) U.S. Cl.
CPC ............ *C07D 211/16* (2013.01); *A61K 31/445* (2013.01); *C07C 233/65* (2013.01); *C07C 233/66* (2013.01); *C07D 207/06* (2013.01); *C07D 211/10* (2013.01); *C07D 211/14* (2013.01); *C07D 211/96* (2013.01); *C07D 223/04* (2013.01); *C07D 225/02* (2013.01); *C07D 265/30* (2013.01); *C07D 295/192* (2013.01); *C07C 2101/14* (2013.01)

(58) Field of Classification Search
None
See application file for complete search history.

(56) References Cited

U.S. PATENT DOCUMENTS

| 3,206,439 A | 9/1965 | Detoro et al. |
|---|---|---|
| 3,463,855 A | 8/1969 | Yoho |

(Continued)

FOREIGN PATENT DOCUMENTS

| EP | 1792911 | 6/2007 |
|---|---|---|
| JP | 11-501319 | 2/1999 |

(Continued)

OTHER PUBLICATIONS

Soto. Unfolding the role of protein misfolding in neurodegenerative diseases, (2003) Nature Neuroscience, vol. 4, pp. 49-60.*

(Continued)

*Primary Examiner* — Melenie McCormick
*Assistant Examiner* — Taina D Matos Negron
(74) *Attorney, Agent, or Firm* — Morgan, Lewis & Bockius LLP

(57) ABSTRACT

The present invention identifies a compound which binds to the PAH1 domain of mSin3B that specifically binds to neural restrictive silencer factor NRSF, and uses the compound as a prophylactic and/or a therapeutic for diseases associated with abnormal expression of neural restrictive silencer factor NRSF/REST or abnormal expression of genes targeted by NRSF/REST, such as Huntington's disease, medulloblastoma and neuropathic pain.

The present invention provides a pharmaceutical composition comprising a substance capable of binding to the PAH1 domain of mSin3B, e.g., a compound represented by the following formula (1), a pharmacologically acceptable salt thereof, or a pharmacologically acceptable ester thereof:

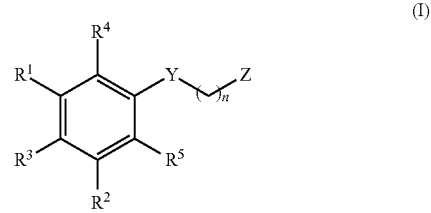

wherein n represents 0 or 1; $R^1$, $R^2$, $R^3$, $R^4$ and $R^5$ each independently represent a hydrogen atom, a hydrocarbon group or a functional group; Y represents a single bond, a carbonyl group, —CONH—, —NHCO— or a sulfonyl group; and Z represents a nitrogen-containing heterocyclic group which may have a substituent, an amino group which may have a hydrocarbon group or an aromatic hydrocarbon group, or a nitrogen and oxygen-containing heterocyclic group which may have a substituent.

3 Claims, 12 Drawing Sheets

(51) Int. Cl.

| | |
|---|---|
| C07D 295/192 | (2006.01) |
| C07C 233/66 | (2006.01) |
| C07D 207/06 | (2006.01) |
| C07D 223/04 | (2006.01) |
| C07D 225/02 | (2006.01) |
| C07D 265/30 | (2006.01) |

(56) References Cited

U.S. PATENT DOCUMENTS

| | | | | |
|---|---|---|---|---|
| 5,643,965 | A | 7/1997 | Flitter et al. | 514/619 |
| 5,658,953 | A | 8/1997 | Flitter et al. | 514/616 |
| 5,659,082 | A | 8/1997 | Flitter et al. | 564/166 |
| 5,756,548 | A | 5/1998 | Flitter et al. | 514/616 |
| 5,907,061 | A | 5/1999 | Flitter et al. | 564/142 |
| 5,914,350 | A | 6/1999 | Flitter et al. | 514/619 |
| 5,955,506 | A | 9/1999 | Flitter et al. | 514/616 |
| 6,066,765 | A | 5/2000 | Flitter et al. | 564/155 |
| 6,077,870 | A | 6/2000 | Flitter et al. | 514/616 |
| 6,140,369 | A | 10/2000 | Flitter et al. | 514/616 |
| 6,509,378 | B2 | 1/2003 | Flitter et al. | 514/616 |
| 6,759,433 | B2 | 7/2004 | Flitter et al. | 514/616 |
| 7,005,546 | B2 | 2/2006 | Flitter et al. | 564/153 |
| 2001/0037040 | A1 | 11/2001 | Flitter et al. | 564/156 |
| 2003/0176510 | A1 | 9/2003 | Flitter et al. | 514/616 |
| 2004/0266881 | A1 | 12/2004 | Flitter et al. | 514/616 |
| 2005/0239881 | A1 | 10/2005 | Dunn et al. | 514/522 |
| 2006/0035890 | A1 | 2/2006 | Banerjee | 514/229.2 |
| 2006/0100461 | A1 | 5/2006 | Flitter et al. | 564/152 |
| 2006/0111366 | A1 | 5/2006 | Andersen et al. | 514/253.01 |
| 2006/0121488 | A1 | 6/2006 | Rothstein | 435/6 |
| 2009/0036420 | A1 | 2/2009 | Galley et al. | 514/210.2 |
| 2009/0062292 | A1 | 3/2009 | Charrier et al. | 514/250 |
| 2009/0111791 | A1 | 4/2009 | De Lombaert et al. | 514/210.18 |

FOREIGN PATENT DOCUMENTS

| | | |
|---|---|---|
| JP | 2006-522746 | 10/2006 |
| JP | 2006-524637 | 11/2006 |
| JP | 2007-533682 | 11/2007 |
| JP | 2009-529577 | 8/2009 |
| JP | 2009-536155 | 10/2009 |
| WO | WO2004089470 A2 * | 11/2004 |
| WO | WO 2006/020681 | 2/2006 |
| WO | WO 2007/106706 A1 | 9/2007 |
| WO | WO2007106705 * | 9/2007 |
| WO | WO 2009/016088 A1 | 2/2009 |

OTHER PUBLICATIONS

Fuller et al. Many human medulloblastoma tumors overexpress repressor element-1 silencing transcription (REST)/neuron-restrictive silencer factor, which can be functionally countered by REST-VP16 Mol. Cancer Ther. (2005), vol. 4, pp. 343-349.*

Database CAPlus on Stn, American Chemical Society, Dn:93:142676, abstract, Zhang, X. et al., Relation between chemical structure and physiological activity in cinnamamides and their analogs, 1980, vol. 12, No. 2, p. 83-91.

Database CAPlus on STN, American Chemical Society, DN:126:139503, abstract, Srivastava, V et al., Evaluation of some acylamide derivatives as potential hypoglycemic agents, 1996, vol. 135, No. 7, p. 452-457.

Database CAPlus on STN, American Chemical Society, DN: 68:95646, abstract, Sam, J. at al., Preparation of Some N-benzylpiperidines, 1967, vol. 56, No. 6, p. 729-31.

Palmer et al., "Mechanism of cell death induced by the novel enzyme-prodrug combination, nitroreductase/CB1954, and identification of synergism with 5-fluorouracil", British Journal of Cancer, 2003, vol. 89, No. 5, p. 944-950.

Benoit-Guyod, M et al., Dipropylacetic acid series. IX. Structural Homologs: 1-methyl-2-propylpentylamine, and substituted amides and ureas, Chimica Theraputica, 1973, vol. 8, No. 4, p. 412-418.

Database CAPlus on STN, American Chemical Society, DN: 80:729, abstract, Pagani G. et al., Phytotoxic activity of di-sec-butylamides of alkyl-and halonitrobenzoic acids, Farmaco, Edizione Scientifica, 1973, vol. 28, No. 9, p. 741-752.

Database Registry on STN, RN333350-41-7, entered STN on Apr. 27, 2001, Chemical library supplier : AsInEx.

Database Registry on STN, RN438529-71-6, entered STN on Jul. 15, 2001, Chemical library supplier : Ambinter.

Database Registry on STN, RN333350-40-6, entered STN on Apr. 27, 2001, Chemical library supplier : AsInEx.

Database Registry on STN, RN303137-53-3, entered STN on Nov. 11, 2000, Chemical library supplier : ChemStar.

International preliminary report on patentability dated Oct. 11, 2012 issued in corresponding PCT application PCT/JP2011/052710.

Database Registry(Online) Chemical Abstracts Service, Columbus Ohio, US; 2008, Chemical Abstract: XP002719377.

Extended European Search Report mailed Feb. 14, 2014 for European Application No. 11742245.1.

Nomura et al: "The Neutral Repressor NRSF/REST Binds the PAH1 Domain of the Sin2 Corepressor by using its Distinct Short Hydrophobic Helix", Journal of Molecular Biology, Academic Press, United Kingdom, vol. 354, No. 4, Dec. 9, 2005 pp. 903-915.

Sahu et al: "Conserved Themes in Targe Recognition by the PAH1 and PAH2 Domains of the Sin3 Transcriptional Corepressor", Journal of Molecular Biology, Academic Press, United Kingdom., vol. 375, No. 5, Dec. 4, 2007, pp. 1444-1456.

* cited by examiner

USE OF COMPOUND BINDING TO MSIN3B THAT SPECIFICALLY BINDS TO NEURON RESTRICTIVE SILENCER FACTOR (NRSF)

CROSS REFERENCE TO THE RELATED APPLICATIONS

This application is a national stage of international application No. PCT/JP2011/052710, filed on Feb. 9, 2011 and claims the benefit of priority under 35 USC 119 to Japanese Patent Application No. 2010-027066, filed on Feb. 10, 2010, the entire contents of which are incorporated herein by reference.

TECHNICAL FIELD

The present invention relates to use of compounds binding to mSin3B that specifically binds to a neural restrictive silencer factor (NRSF). More specifically, the present invention relates to medicinal applications of compounds binding to mSin3B that specifically binds to NRSF.

BACKGROUND ART

Formation of normal cells, tissues and organs in the body is achieved through expression of genes at appropriate times, in appropriate places and in appropriate quantities. As a result, normal function is exerted. For example, neural genes must be expressed properly in neuronal cells but not in non-neural cells. NRSE/RE1 (neural restrictive silencer element/repressor element 1) is a silencer consisting of 21 base pairs and present in the vicinity of neuron specific genes. This silencer plays a central role in neuron-specific transcriptional regulation of more than 30 genes for such substances as neurotransmitter synthetases, ion channels, neuronal growth-associated proteins, and so forth. It is said that approximately 1000 genes (mainly neuron specific genes) have this silencer. This silencer does not work in neuronal cells but suppresses expression of neuron specific genes in non-neuronal cells, to thereby assure expression of neuron specific genes in neuronal cells. It is also believed that this silencer is not only involved in the expression control of neuron specific genes but also involved in terminal differentiation of neuronal cells. It is NRSF/REST (neural restrictive silencer factor) that has been identified as a transcriptional repression factor which binds to the above-described NRSE/RE1 and represses expression of neuron specific genes in non-neuronal cells.

It is reported that abnormal expression of NRSF/REST and genes targeted by NRSF/REST is involved in neurodegenerative diseases, such as Down's syndrome, Alzheimer's disease and Huntington's disease, and medulloblastoma.

Down's syndrome is a disease caused by chromosome 21 trisomy mutation. Examination of difference in genes between neural tissues of fetuses dying from Down's syndrome and those of normal fetuses revealed that expression of SCG10 (a neuron-specific growth-associated protein) gene and other genes targeted by NRSF/REST such as decreased greatly in the former. On the other hand, those proteins regulated by transcription factors other than NRSF/REST were expressed normally (Non-Patent Document No. 1).

Alzheimer's disease is a disease caused by accumulation of β amyloid and neurofibrillary tangle and neuronal death. Expression of SCG10 was altered in Alzheimer's disease brains (Non-Patent Document No. 2).

Medulloblastoma is the most malignant brain tumor in children. Expression levels of NRSF/REST in medulloblastoma cells are very high. A recombinant protein REST-VP16 that antagonizes NRSF/REST and activates genes there targeted thereby promotes expression of neuronal genes and also activates the caspase cascade to thereby induce apoptosis. REST-VP16 is a potential therapeutic (Non-Patent Document No. 3).

Huntington's disease is a progressive, neurodegenerative disease manifesting choreic movement, dementia and personality change as major symptoms. It is believed that abnormal huntingtin molecules with a repeat structure of glutamine residues form aggregates to thereby induce neurodegeneration. Wild-type huntingtin binds to NRSF/REST in the cytoplasm to regulate the binding of NRSF/REST to NRSE/RE1. On the other hand, this control is lost in Huntington's disease; thus, neuronal genes are not expressed sufficiently (Non-Patent Document No. 4).

Chronic pain caused by neuronal disorders (neuropathic pain) presents complicated pain symptoms in which positive symptoms (pain hypersensitivity and allodynia (a strong pain induced by a tactile stimulus)) and negative symptoms (hypoesthesia) are mixed. Since this abnormal pain shows resistance to anti-inflammatory drugs and morphine, it is regarded as intractable pain.

Recently, Uchida et al. revealed that expression of the silencer factor NRSF/REST is enhanced in primary sensory neurons after neuropathy to silence a group of pain-associated genes ($Na_v1.8$, MOP, TRPM8, TRPA1 and $K_v4.3$) through epigenetic modification (lowering of histone acetylation) and induce C-fiber hypoesthesia and morphine resistance which are characteristic of neuropathic pain (Non-Patent Documents Nos. 7, 8, 9 and 10).

Further, Naruse et al. revealed that the N-terminal transcriptional repressor domain of NRSF/REST recruits HDAC through co-repressor mSin3 and that the C-terminal transcriptional repressor domain recruits HDAC through CoREST, and suggested that NRSF/REST represses transcription by deactivation of the chromatin structure (Non-Patent Document No. 5).

The present inventors have already analyzed the structure of a complex composed of the N-terminal transcription repressor domain of NRSF (associated with Huntington's disease, medulloblastoma and neuropathic pain) and the PAH1 domain of co-repressor mSin3B which specifically binds to that domain (Patent Document No. 1 and Non-Patent Document No. 6).

However, no compounds have been reported so far which bind to mSin3B that specifically binds to neural restrictive silencer factor NRSF.

DISCLOSURE OF THE INVENTION

Problem for Solution by the Invention

It is an object of the present invention to identify compounds which bind to the PAH1 domain of mSin3B that specifically binds to neural restrictive silence factor NRSF that is associated with Huntington's disease, medulloblastoma and neuropathic pain. Such compounds may be used as lead compounds for therapeutics for Huntington's disease, medulloblastoma and neuropathic pain.

Means to Solve the Problem

The present inventors identified by NMR those compounds which bind to the PAH1 domain of mSin3B that specifically binds to neural restrictive silence factor NRSF. Further, the present inventors subjected the above-identified compounds to MTT assay using human medulloblastoma cell strains and found compounds which cause cell death and compounds which inhibit cell growth. Further, hypoesthesia is observed in electrical stimulation-induced paw withdrawal (EPW) test which evaluates pain threshold in response to C-fiber specific electrical stimulation (5 Hz) at the time of neuropathic pain, and disappearance of morphine analgesia is observed in thermal paw withdrawal test which evaluates pain threshold against thermal stimulation. The present inventors found that some of the above-identified compounds that cause recovery from such modulations. The present invention has been achieved based on these findings.

A summary of the present invention is as described below.

(1) A pharmaceutical composition comprising a substance capable of binding to the PAH1 domain of mSin3B.

(2) The pharmaceutical composition according to (1), wherein the substance capable of binding to the PAH1 domain of mSin3B is a compound represented by the following formula (I), a pharmacologically acceptable salt thereof or a pharmacologically acceptable ester thereof:

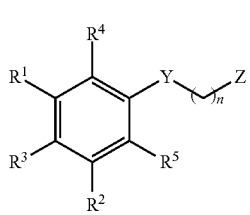

wherein n represents 0 or 1; $R^1$, $R^2$, $R^3$, $R^4$ and $R^5$ each independently represent a hydrogen atom, a hydrocarbon group or a functional group; Y represents a single bond, a carbonyl group, —CONH—, —NHCO— or a sulfonyl group; and Z represents a nitrogen-containing heterocyclic group which may have a substituent, an amino group which may have a hydrocarbon group or an aromatic hydrocarbon group, or a nitrogen and oxygen-containing heterocyclic group which may have a substituent.

(3) The pharmaceutical composition according to (1) or (2), which is used as a prophylactic and/or a therapeutic for diseases associated with abnormal expression of neural restrictive silencer factor NRSF/REST or abnormal expression of genes targeted by NRSF/REST.

(4) The pharmaceutical composition according to (3), wherein the disease associated with abnormal expression of neural restrictive silencer factor NRSF/REST or abnormal expression of genes targeted by NRSF/REST is neurodegenerative disease, cancer, atopic dermatitis, diabetes, cardiomyopathy or neuropathic pain.

(5) The pharmaceutical composition according to (4), wherein the neurodegenerative disease is Down's syndrome, Alzheimer's disease, Huntington's disease or Parkinson's disease.

(6) The pharmaceutical composition according to (4), wherein the cancer is medulloblastoma.

(7) The pharmaceutical composition according to any one of (1) to (6), wherein the compound represented by formula (I) is represented by any of the following formulas:

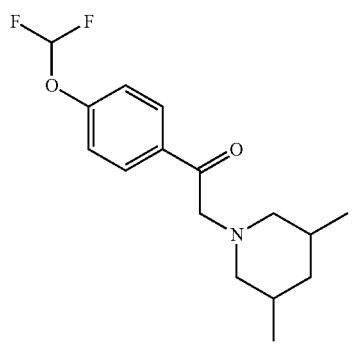
A28

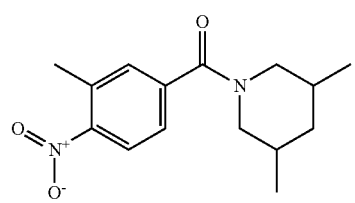
155

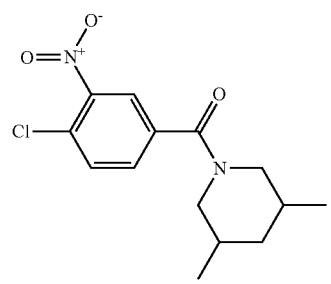
5

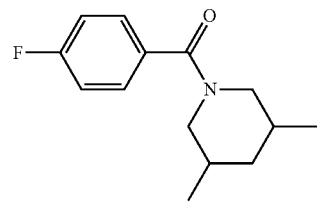
15

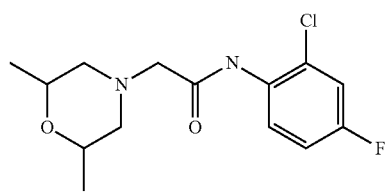
23

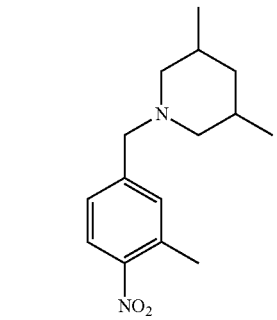
NCR-7

(8) A method of preventing and/or treating diseases associated with abnormal expression of neural restrictive silencer factor NRSF/REST or abnormal expression of genes targeted by NRSF/REST, comprising administering to a subject a pharmacologically effective amount of a substance capable of binding to the PAH1 domain of mSin3B.

(9) Use of a substance capable of binding to the PAH1 domain of mSin3B, for preparing a prophylactic and/or a therapeutic for diseases associated with abnormal expression of neural restrictive silencer factor NRSF/REST or abnormal expression of genes targeted by NRSF/REST.

(10) Use of a substance capable of binding to the PAH1 domain of mSin3B, for preventing and/or treating diseases associated with abnormal expression of neural restrictive silencer factor NRSF/REST or abnormal expression of genes targeted by NRSF/REST.

(11) A substance capable of binding to the PAH1 domain of mSin3B, for use in a method of preventing and/or treating diseases associated with abnormal expression of neural restrictive silencer factor NRSF/REST or abnormal expression of genes targeted by NRSF/REST.

(12) A compound represented by the following formula (Ia), a pharmacologically acceptable salt thereof, or a pharmacologically acceptable ester thereof

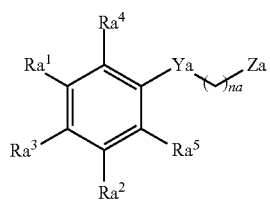

(Ia)

wherein $n_a$ represents 0 or 1; $R_a^1$, $R_a^2$, $R_a^3$, $R_a^4$ and $R_a^5$ each independently represent a hydrogen atom, a hydrocarbon group or a functional group; $Y_a$ represents a single bond, a carbonyl group, —CONH—, —NHCO— or a sulfonyl group; and $Z_a$ represents a nitrogen-containing heterocyclic group which may have a substituent, an amino group which may have a hydrocarbon group or an aromatic hydrocarbon group, or a nitrogen and oxygen-containing heterocyclic group which may have a substituent.

(13) The compound, the pharmacologically acceptable salt thereof or the pharmacologically acceptable ester thereof according to (8), wherein the compound represented by formula (Ia) is a compound represented by any of the following formulas:

NCR-1

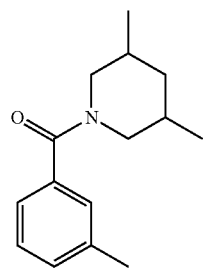

-continued

NCR-2

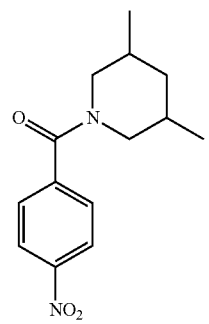

NCR-3

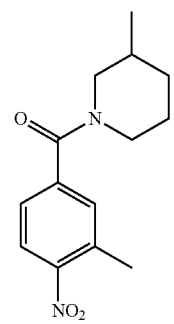

NCR-4

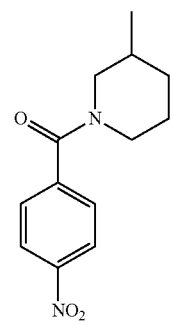

NCR-5

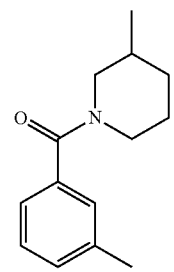

NCR-6

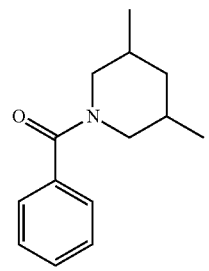

NCR-7
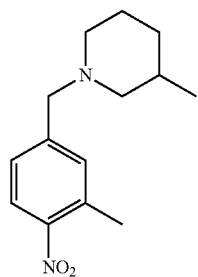
NCR-8
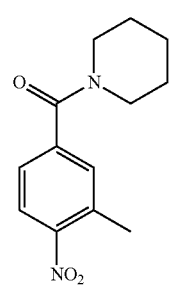
NCR-9
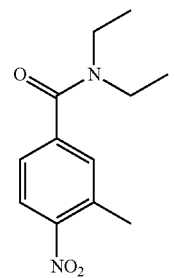
NCR-10
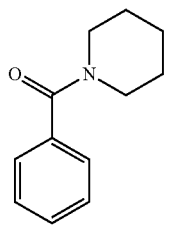
NCR-11
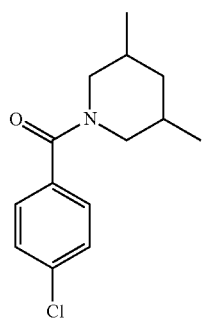
NCR-12
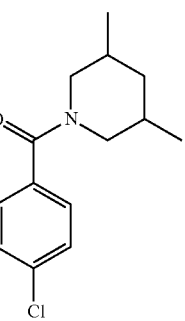
NCR-13
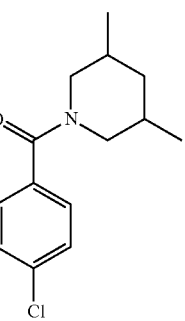
NCR-14
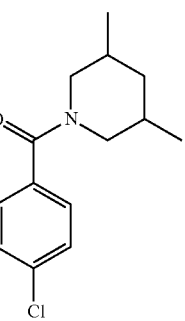
NCR-15
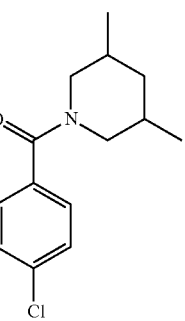
NCR-16
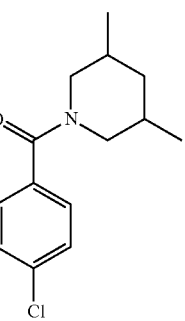

-continued

NCR-17
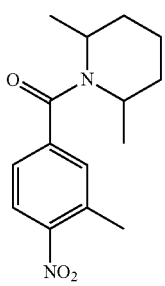

NCR-18
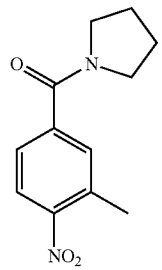

NCR-19
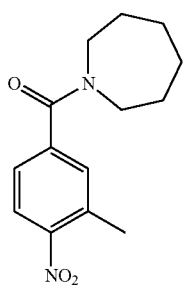

NCR-20
NCR-21
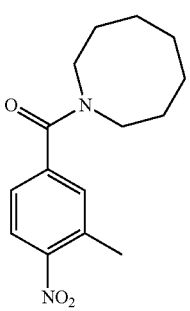

-continued

NCR-22
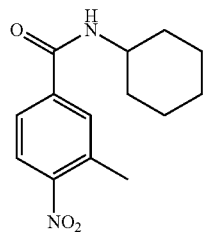

Effect of the Invention

Substances capable of binding to the PAH1 domain of mSin3B (for example, compounds represented by formula (I), pharmacologically acceptable salts thereof, or pharmacologically acceptable esters thereof) may be used as a medicine, in particular, a prophylactic and/or a therapeutic for diseases associated with abnormal expression of neural restrictive silencer factor NRSF/REST or abnormal expression of genes targeted by NRSF/REST.

The present specification encompasses the contents disclosed in the specification and/or the drawings of Japanese Patent Application No. 2010-27066 based on which the present application claims priority.

BEST MODES FOR CARRYING OUT THE INVENTION

Figure 1:
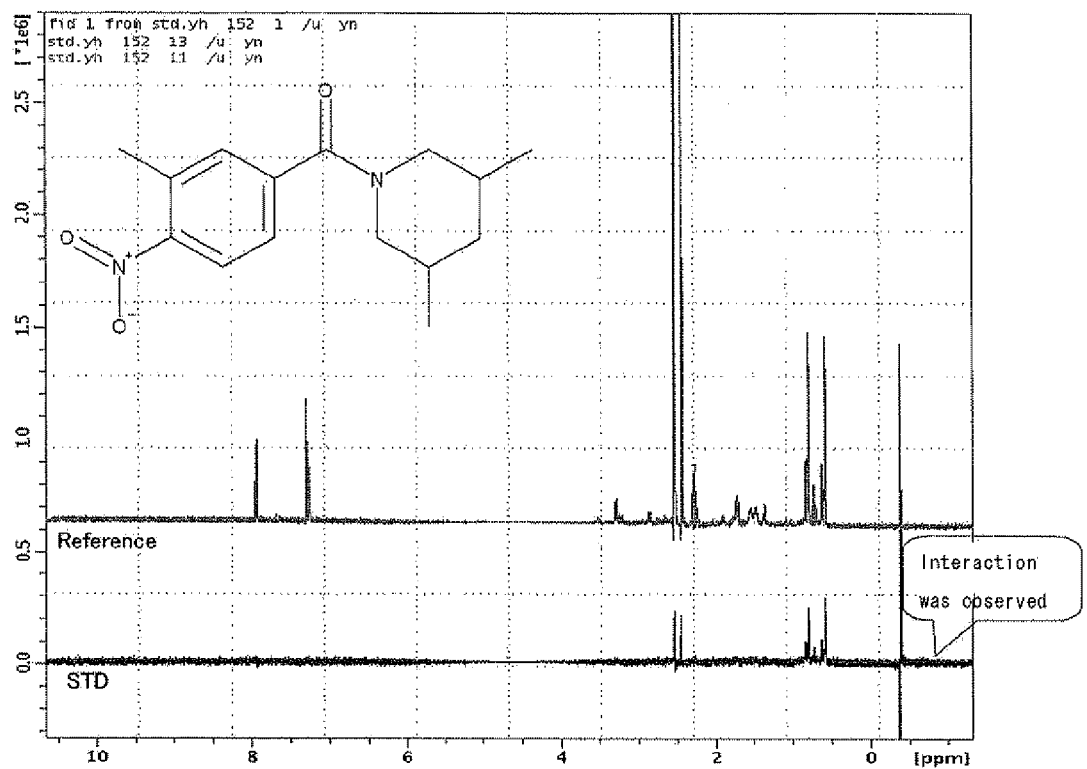
FIG. 1 shows the STD (saturation transfer difference) of 3,5-dimethylpiperidyl 3-methyl-4-nitrophenyl ketone (compound/mSin3B: 400 μM/10 μM).
Figure 2:
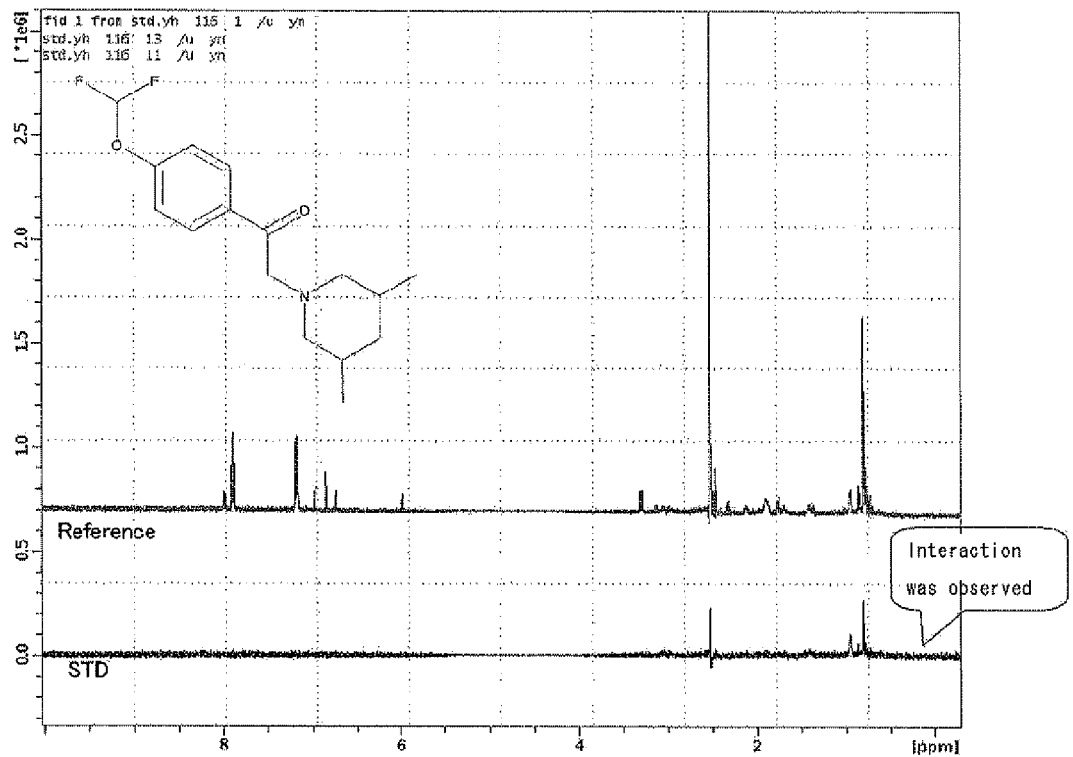
FIG. 2 shows the STD (saturation transfer difference) of 1-[4-(difluoromethoxy)phenyl]-2-(3,5-dimethylpiperidyl) ethan-1-one (compound/mSin3B: 400 μM/10 μM).
Figure 3:
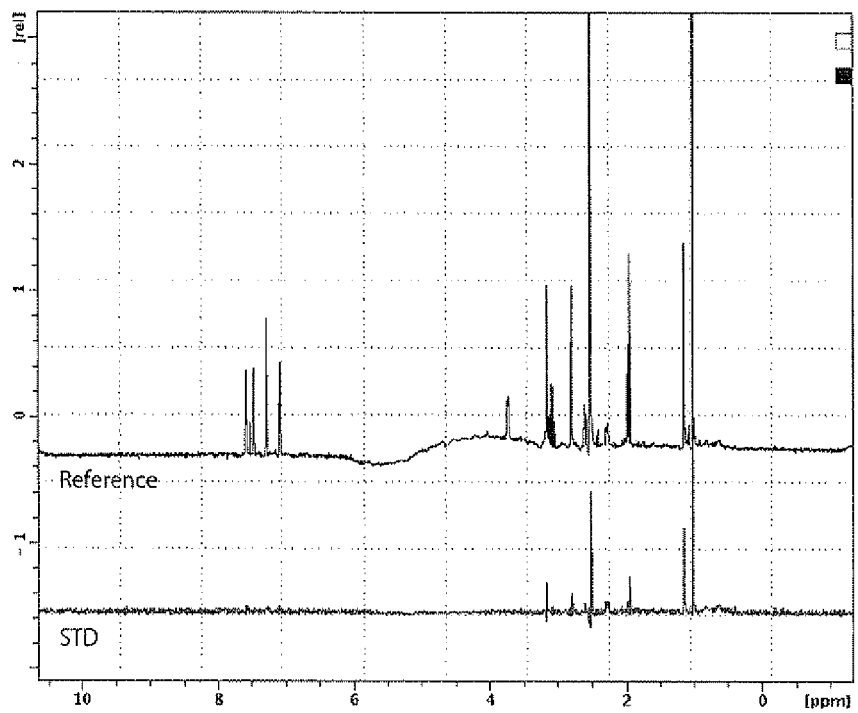
FIG. 3 shows the STD (saturation transfer difference) of compound 5 (3,5-dimethylpiperidyl 4-chloro-3-nitrophenyl ketone) (compound/mSin3B: 400 μM/10 μM).
Figure 4:
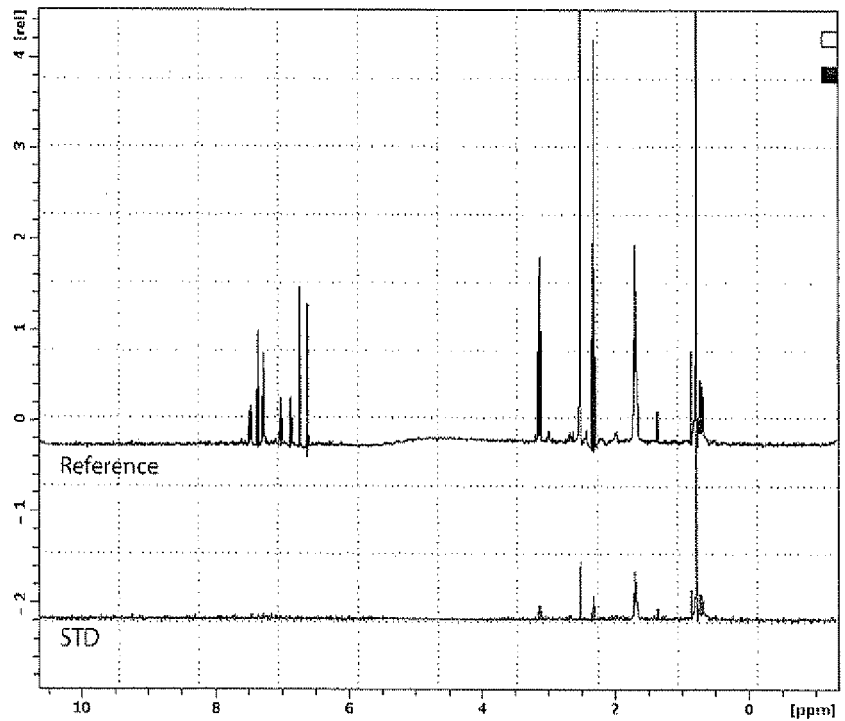
FIG. 4 shows the STD (saturation transfer difference) of compound 15 (3,5-dimethylpiperidyl 4-fluorophenyl ketone) (compound/mSin3B: 400 μM/10 μM).
Figure 5:
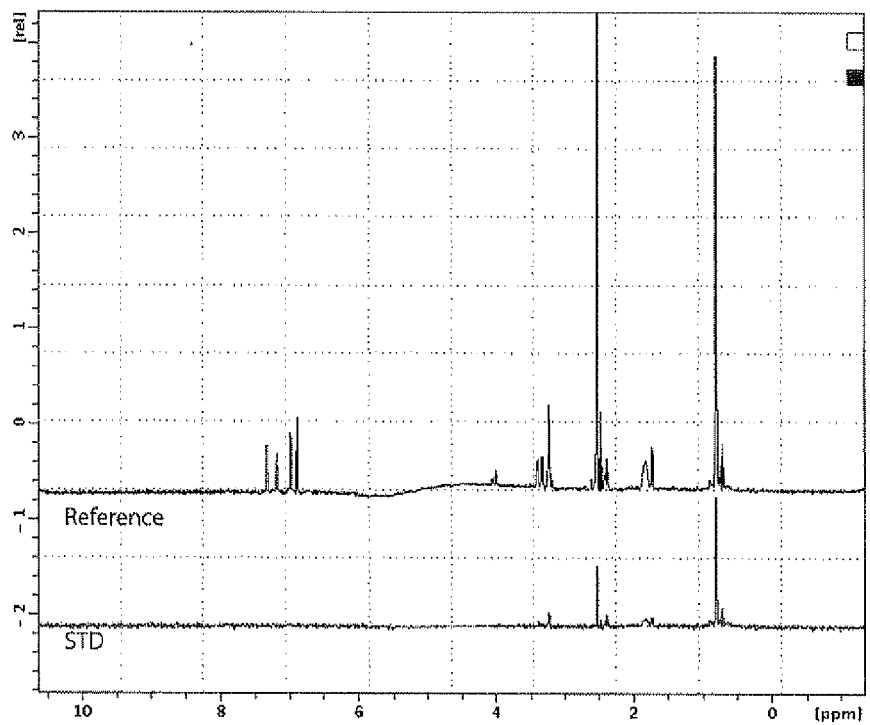
FIG. 5 shows the STD (saturation transfer difference) of compound 23 (2-(2,6-dimethylmorpholin-4-yl)-N-(2-chloro-4-fluorophenyl)acetamide) (compound/mSin3B: 400 μM/10 μM).
Figure 6:
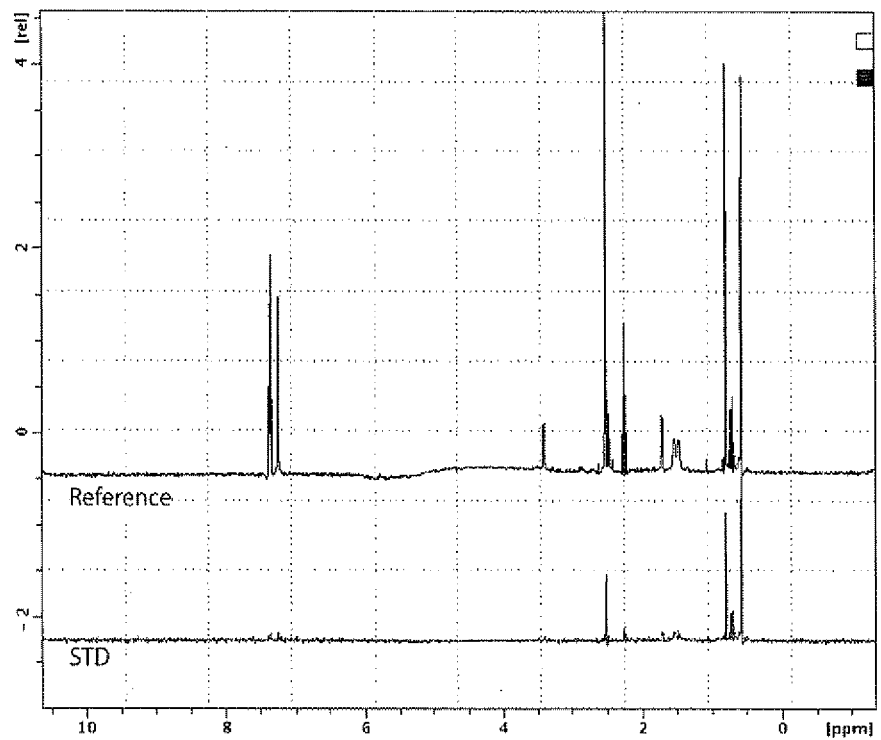
FIG. 6 shows the STD (saturation transfer difference) of compound NCR6 (1-benzoyl-3,5-dimethylpiperidine) (compound/mSin3B: 400 μM/10 μM).
Figure 7:
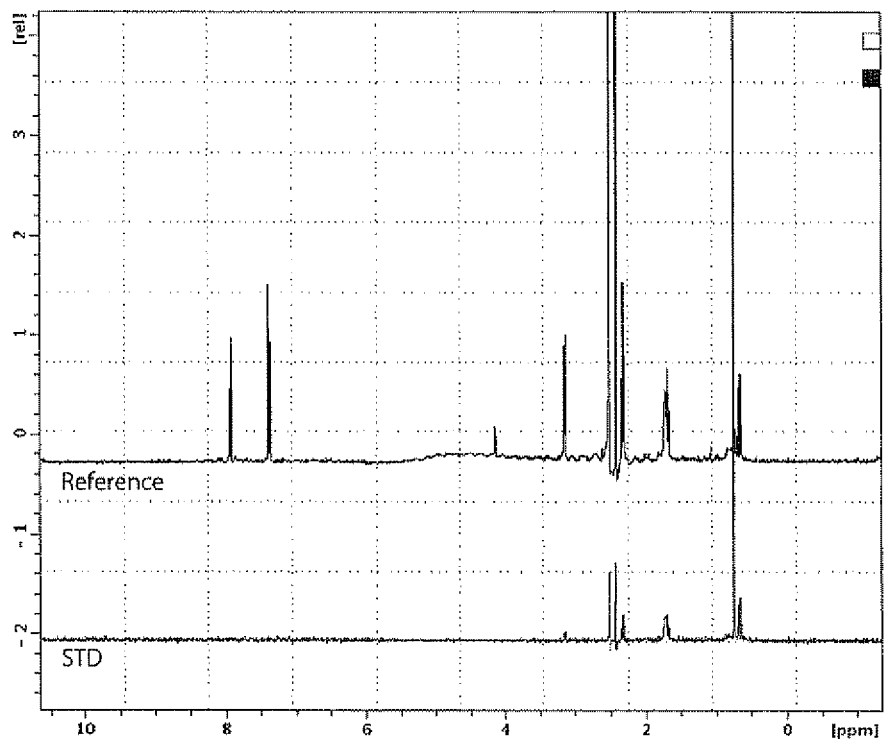
FIG. 7 shows the STD (saturation transfer difference) of compound NCR7 (3,5-dimethyl-1-(3-methyl-4-nitrobenzyl) piperidine) (compound/mSin3B: 400 μM/10 μM).
Figure 8:
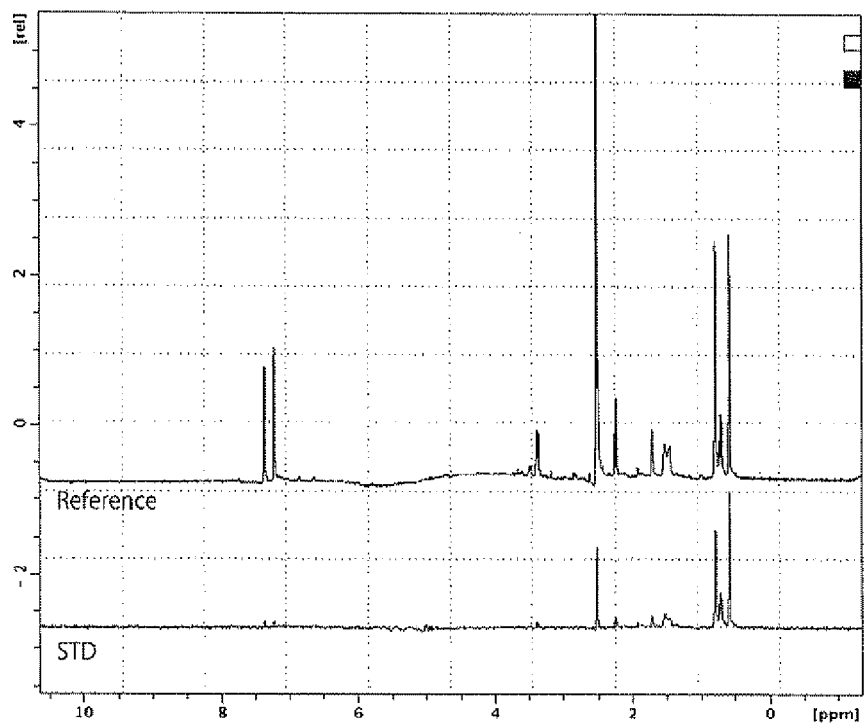
FIG. 8 shows the STD (saturation transfer difference) of compound NCR11 (3,5-dimethyl-1-(4-chlorobenzoyl)piperidine) (compound/mSin3B: 400 μM/10 μM).
Figure 9:
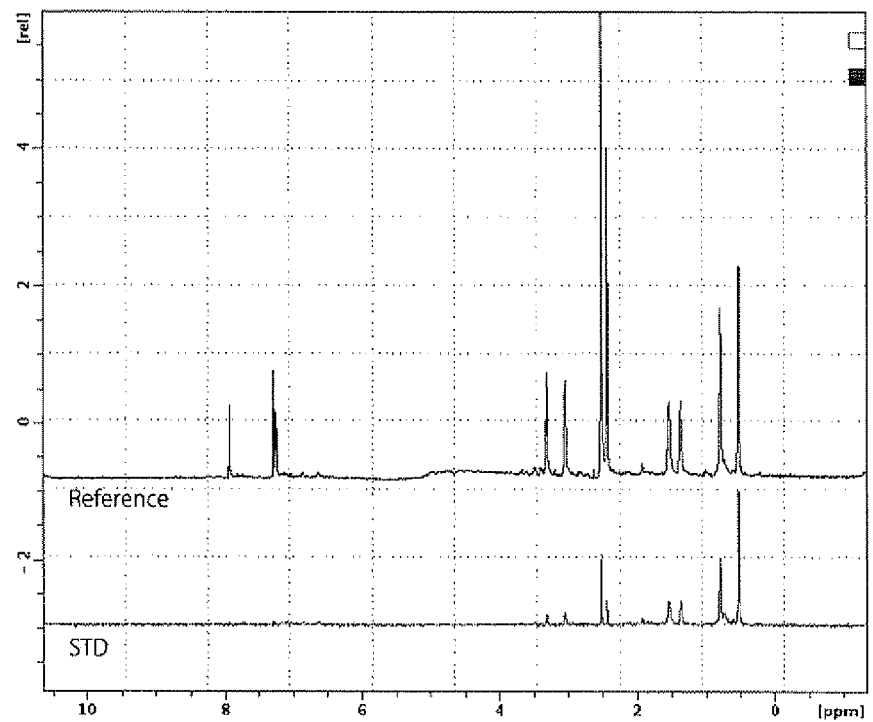
FIG. 9 shows the STD (saturation transfer difference) of compound NCR13 (3-methyl-4-nitro-N,N-dipropylbenzamide) (compound/mSin3B: 400 μM/10 μM).
Figure 10:
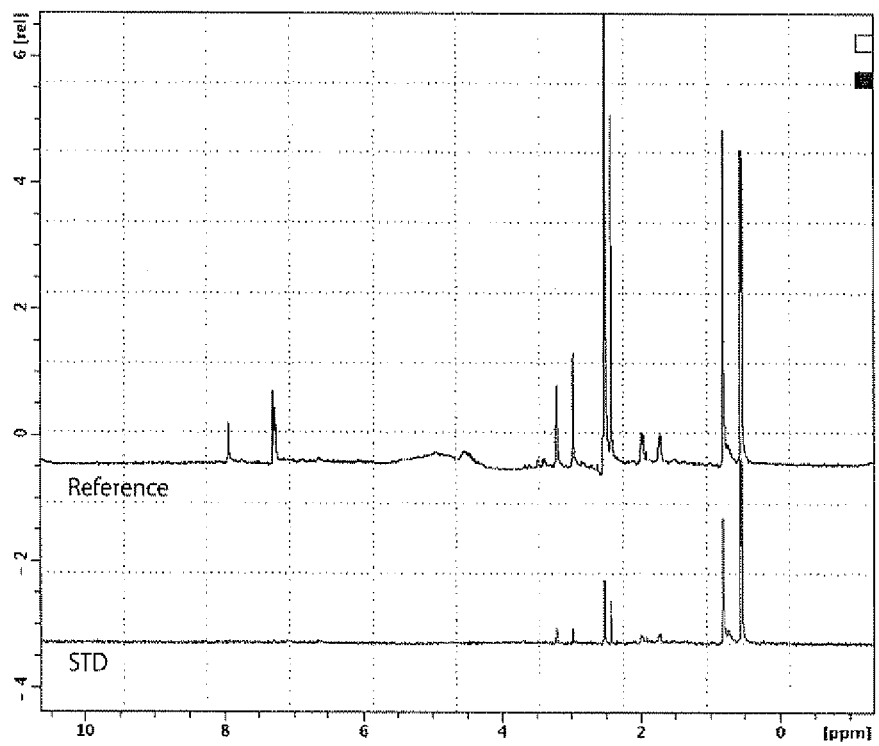
FIG. 10 shows the STD (saturation transfer difference) of compound NCR14 (N,N-diisobutyl-3-methyl-4-nitrobenzamide) (compound/mSin3B: 400 μM/10 μM).
Figure 11:
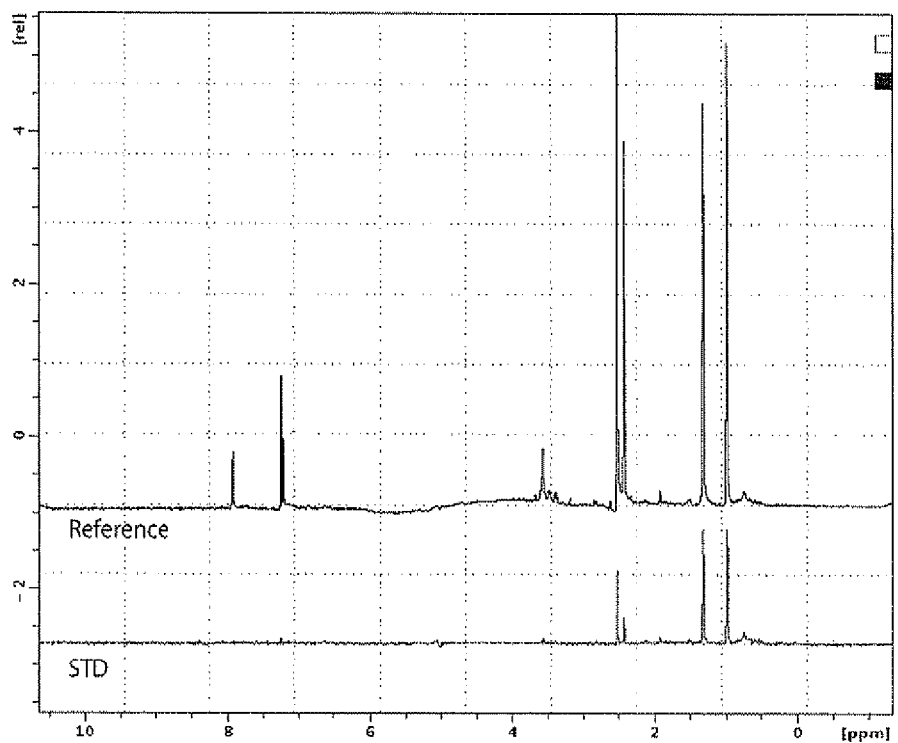
FIG. 11 shows the STD (saturation transfer difference) of compound NCR15 (N,N-diisopropyl-3-methyl-4-nitrobenzamide) (compound/mSin3B: 400 μM/10 μM).

Hereinbelow, modes for carrying out the present invention will be described in more detail.

The present invention provides a pharmaceutical composition comprising a substance capable of binding to the PAH1 domain of mSin3B. Specific examples of the substance capable of binding to the PAH1 domain of mSin3B include, but are not limited to, compounds represented by the following formula (I), pharmacologically acceptable salts thereof, and pharmacologically acceptable esters thereof.

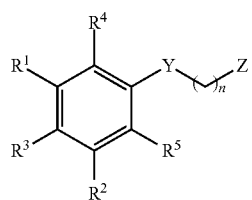

(I)

wherein n represents 0 or 1; $R^1$, $R^2$, $R^3$, $R^4$ and $R^5$ each independently represent a hydrogen atom, a hydrocarbon group or a functional group; Y represents a single bond, a carbonyl group, —CONH—, —NHCO— or a sulfonyl group; and Z represents a nitrogen-containing heterocyclic group which may have a substituent, an amino group which may have a hydrocarbon group or an aromatic hydrocarbon group, or a nitrogen and oxygen-containing heterocyclic group which may have a substituent.

As the hydrocarbon group of $R^1$, $R^2$, $R^4$ and $R^5$ specific examples include, but are not limited to, alkyl groups (preferably, $C_1$-$C_6$ straight-chained or branched alkyl groups, more preferably, methyl group, ethyl group, normal propyl group, isopropyl group, etc.).

As the functional group of $R^1$, $R^2$, $R^4$ and $R^5$, specific examples include, but are not limited to, alkoxy groups (preferably, $C_1$-$C_6$ straight-chained or branched alkoxy groups, more preferably, methoxy group, ethoxy group, etc.), sulfonyl group which may have a substituent, nitro group, halogen groups (fluoro group, chloro group, bromo group, iodo group, etc.), and sulfamoyl group which may have a substituent. As the substituents on sulfonyl group and sulfamoyl group, specific examples include, but are not limited to, those substituents listed in Tables provided herein later.

As the hydrocarbon group of $R^3$, specific examples include, but are not limited to, aromatic hydrocarbon groups (preferably, $C_1$-$C_6$ aromatic hydrocarbon groups, more preferably, phenyl, naphthyl, anthryl, phenanthryl, acenaphthylenyl, biphenylyl, indenyl, etc.), alkyl groups which may have a substituent (preferably, $C_1$-$C_6$ straight-chained or branched alkyl groups, more preferably, methyl group, ethyl group, normal propyl group, isopropyl group, normal butyl group, isobutyl group, s-butyl group, t-butyl group, etc.), and alkenyl groups which may have a substituent (preferably, $C_2$-$C_6$ straight-chained or branched alkenyl groups, more preferably, vinyl group and 1-isopropenyl group). As the substituent on alkyl groups and alkenyl groups, specific examples include, but are not limited to, those substituents listed in Tables provided herein later.

As the functional group of $R^3$, specific examples include, but are not limited to, nitro group, difluoromethoxy group, amide groups which may have a substituent, halogen groups (fluoro group, chloro group, bromo group, iodo group, etc.), alkoxy group which may have a substituent (preferably, $C_1$-$C_6$ straight-chained or branched alkoxy groups, more preferably, methoxy group, ethoxy group, propoxy group, isopropoxy group, butoxy group, isobutoxy group, s-butoxy group, t-butoxy group, pentyloxy group, hexyloxy group, etc.), acetoxy group, cyano group, sulfonyl group which may have a substituent, sulfamoyl group which may have a substituent, amino groups which may have a substituent, piperidyl group which may have a substituent, phenoxy group, hydroxy group, acyl groups, triazolyl group, imidazolyl group, alkoxycarbonyl groups (wherein the alkoxy group is preferably a $C_1$-$C_6$ straight-chained or branched alkoxy group, more preferably, methoxy group or ethoxy group), tetrazolyl group, pyrazolyl group which may have a substituent, piperidylcarbonyl group which may have a substituent, pyrrolidinyl group, alkylsulfanyl groups which may have a substituent (wherein the alkyl group is preferably a $C_1$-$C_6$ straight-chained or branched alkyl groups, more preferably, methyl group, ethyl group, normal propyl group, isopropyl group, normal butyl group, isobutyl group, s-butyl group, t-butyl group, etc.), oxadiazolyl group which may have a substituent, and heterocyclic groups which may have a substituent (wherein the heterocyclic group is preferably a 5-10 membered heterocyclic group containing 1-3 heteroatoms (e.g., sulfur atom, oxygen atom, nitrogen atom, etc.), more preferably 3H-quinazoline-4-one, 2,4,5-trihydroisothiazole-1,1,3-trione, benzoimidazole and the like). As the substituent in amide groups, alkoxy groups, sulfonyl group, sulfamoyl group, amino groups, piperidyl group, pyrazolyl group, piperidylcarbonyl group, alkylsulfanyl groups, oxadiazolyl group and heterocyclic groups, and as the acyl group, specific examples include, but are not limited to, those listed in Tables provided herein later.

As the "substituent" in the "nitrogen-containing heterocyclic group which may have a substituent" in Z, specific examples include, but are not limited to, saturated chain hydrocarbon groups (e.g., $C_1$-$C_6$ alkyl groups such as methyl, ethyl, propyl, isopropyl, butyl, isobutyl, s-butyl, t-butyl, pentyl, isopentyl, neopentyl, t-pentyl, 1-methylbutyl and hexyl), unsaturated chain hydrocarbon groups (e.g., $C_2$-$C_6$ alkenyl groups such as vinyl, allyl, 1-propenyl, isopropenyl, 1-butenyl, 2-butenyl and 3-methylallyl; and $C_2$-$C_6$ alkynyl groups such as ethynyl and 2-propynyl), alicyclic hydrocarbon groups (such as cyclohexyl, 1-cyclohexenyl and cyclohexylidene), and aromatic hydrocarbon groups (such as benzyl, tolyl and xylyl). The number of such substituent may be one or more.

As the "nitrogen-containing heterocyclic group" in the "nitrogen-containing heterocyclic group which may have a substituent" in Z, specific examples include, but are not limited to, nitrogen-containing 3-8 membered rings such as aziridine, azetidine, pyrrolidine, piperidine, hexamethyleneimine and heptamethyleneimine.

As the "hydrocarbon group" in the "amino group which may have a hydrocarbon group or an aromatic hydrocarbon group" in Z, specific examples include, but are not limited to, saturated chain hydrocarbon groups (e.g., $C_1$-$C_6$ alkyl groups such as methyl, ethyl, propyl, isopropyl, butyl, isobutyl, s-butyl, t-butyl, pentyl, isopentyl, neopentyl, t-pentyl, 1-methylbutyl and hexyl), unsaturated chain hydrocarbon groups (e.g., $C_2$-$C_6$ alkenyl groups such as vinyl, allyl, 1-propenyl, isopropenyl, 1-butenyl, 2-butenyl and 3-methylallyl; and $C_2$-$C_6$ alkynyl groups such as ethynyl and 2-propynyl), and alicyclic hydrocarbon groups (such as cyclohexyl, 1-cyclohexenyl and cyclohexylidene). As the aromatic hydrocarbon group, such as benzyl, tolyl, xylyl and the like may be given. The amino group may have one or more hydrocarbon groups and/or aromatic hydrocarbon groups.

As the "substituent" in the "nitrogen and oxygen-containing heterocyclic group which may have a substituent" in Z, specific examples include, but are not limited to, saturated chain hydrocarbon groups (e.g., $C_1$-$C_6$ alkyl groups such as methyl, ethyl, propyl, isopropyl, butyl, isobutyl, s-butyl, t-butyl, pentyl, isopentyl, neopentyl, t-pentyl, 1-methylbutyl and hexyl), unsaturated chain hydrocarbon groups (e.g., $C_2$-$C_6$ alkenyl groups such as vinyl, allyl, 1-propenyl, isopropenyl, 1-butenyl, 2-butenyl and 3-methylallyl; and $C_2$-$C_6$ alkynyl groups such as ethynyl and 2-propynyl), alicyclic hydrocarbon groups (such as cyclohexyl, 1-cyclohexenyl and cyclohexylidene), and aromatic hydrocarbon groups (such as benzyl, tolyl and xylyl). The number of such substituent may be one or more.

As the "nitrogen and oxygen-containing heterocyclic group" in the "nitrogen and oxygen-containing heterocyclic group which may have a substituent" in Z, specific examples include, but are not limited to, morpholine.

Specific examples of the compound represented by formula (I) include, but are not limited to, 3,5-dimethylpiperidyl 3-methyl-4-nitrophenyl ketone, 1-[4-(difluoromethoxy)phenyl]-2-(3,5-dimethylpiperidyl)ethan-1-one, 3,5-dimethylpiperidyl 4-chloro-3-nitrophenyl ketone, 3,5-dimethylpiperidyl 4-fluorophenyl ketone, (2-(2,6-dimethylmorpholin-4-yl)-N-(2-chloro-4-fluorophenyl)acetamide and 3,5-dimethyl-1-(3-methyl-4-nitrobenzyl)piperidine). The structures of 3,5-dimethylpiperidyl 3-methyl-4-nitrophenyl ketone (compound 155), 1-[4-(difluoromethoxy)phenyl]-2-(3,5-dimethylpiperidyl)ethan-1-one (compound A28), 3,5-dimethylpiperidyl 4-chloro-3-nitrophenyl ketone (compound 5), 3,5-dimethylpiperidyl 4-fluorophenyl ketone (compound 15), 2-(2,6-dimethylmorpholin-4-yl)-N-(2-chloro-4-fluorophenyl)acetamide (compound 23) and 3,5-dimethyl-1-(3-methyl-4-nitrobenzyl)piperidine (compound NCR7) are described below.

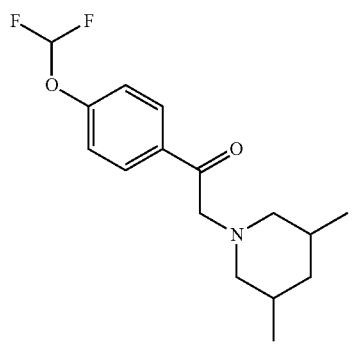
A28

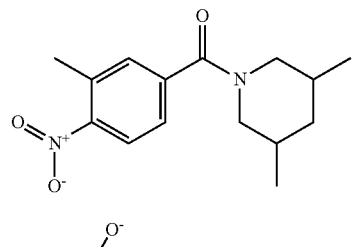
155

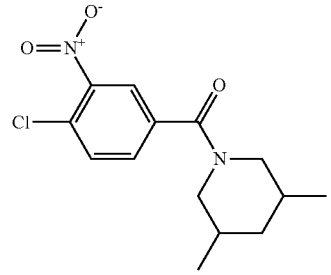
5

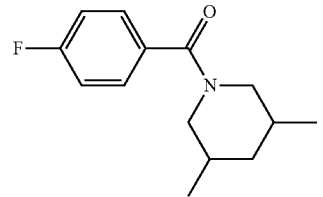
15

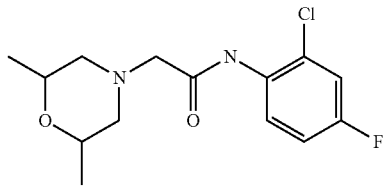
23

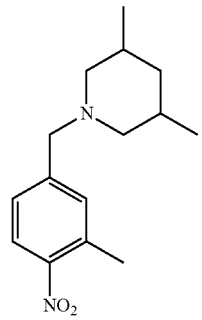
NCR-7

3,5-Dimethylpiperidyl 3-methyl-4-nitrophenyl ketone may be purchased from SPECS (Netherland), Asinex Gold (Russia) or ASDI (U.S.A.).

1-[4-(Difluoromethoxy)phenyl]-2-(3,5-dimethylpiperidyl)ethan-1-one may be purchased from Enamine (Ukraine).

Compound 5 may be purchased from Vitas-M Laboratory, Ltd. (Russia).

Compound 15 may be purchased from Vitas-M Laboratory, Ltd. (Russia).

Compound 23 may be purchased from Enamine (Ukraine).

Compound NCR-7 may be prepared according to the method described in Preparation Example 21.

It should be noted that the compound represented by formula (I) may be a compound represented by the following formula (Ia).

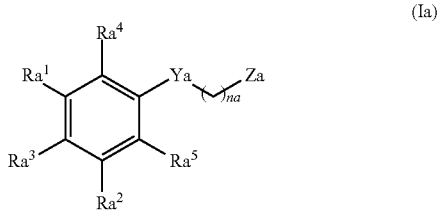

(Ia)

wherein $n_a$ represents 0 or 1; $R_a^1$, $R_a^2$, $R_a^3$, $R_a^4$ and $R_a^5$ each independently represent a hydrogen atom, a hydrocarbon group or a functional group; $Y_a$ represents a single bond, a carbonyl group, —CONH—, —NHCO— or a sulfonyl group; and $Z_a$ represents a nitrogen-containing heterocyclic group which may have a substituent, an amino group which may have a hydrocarbon group or an aromatic hydrocarbon group, or a nitrogen and oxygen-containing heterocyclic group which may have a substituent.

As the hydrocarbon group of $R_a^1$, $R_a^2$, $R_a^4$, and $R_a^5$, specific examples include, but are not limited to, alkyl groups (preferably, $C_1$-$C_6$ straight-chained or branched alkyl groups, more preferably, methyl group, ethyl group, normal propyl group, isopropyl group, etc.).

As the functional group of $R_a^1$, $R_a^2$, $R_a^4$, and $R_a^5$, specific examples include, but are not limited to, alkoxy groups (preferably, $C_1$-$C_6$ straight-chained or branched alkoxy groups, more preferably, methoxy group, ethoxy group, etc.), sulfonyl group which may have a substituent, nitro group, halogen groups (fluoro group, chloro group, bromo group, iodo group, etc.), and sulfamoyl group which may have a substituent. As the substituents in sulfonyl group and sulfamoyl group, specific examples include, but are not limited to, those substituents listed in Tables provided herein later.

As the hydrocarbon group of $R_a^3$, specific examples include, but are not limited to, aromatic hydrocarbon groups (preferably, $C_6$-$C_{14}$ aromatic hydrocarbon groups, more preferably, phenyl, naphthyl, anthryl, phenanthryl, acenaphthylenyl, biphenylyl, indenyl, etc.), alkyl groups which may have a substituent (preferably, $C_1$-$C_6$ straight-chained or branched alkyl groups, more preferably, methyl group, ethyl group, normal propyl group, isopropyl group, normal butyl group, isobutyl group, s-butyl group, t-butyl group, etc.), and alkenyl groups which may have a substituent (preferably, $C_2$-$C_6$ straight-chained or branched alkenyl groups, more preferably, vinyl group and 1-isopropenyl group). As the substituent in alkyl groups and alkenyl groups, specific examples include, but are not limited to, those substituents listed in Tables provided herein later.

As the functional group of $R_a^3$, specific examples include, but are not limited to, nitro group, difluoromethoxy group, amide groups which may have a substituent, halogen groups (fluoro group, chloro group, bromo group, iodo group, etc.), alkoxy group which may have a substituent (preferably, $C_1$-$C_6$ straight-chained or branched alkoxy groups, more preferably, methoxy group, ethoxy group, propoxy group, isopropoxy group, butoxy group, isobutoxy group, s-butoxy group, t-butoxy group, pentyloxy group, hexyloxy group, etc.), acetoxy group, cyano group, sulfonyl group which may have a substituent, sulfamoyl group which may have a substituent, amino groups which may have a substituent, piperidyl group which may have a substituent, phenoxy group, hydroxy group, acyl groups, triazolyl group, imidazolyl group, alkoxycarbonyl groups (wherein the alkoxy group is preferably a $C_1$-$C_6$ straight-chained or branched alkoxy group, more preferably, methoxy group or ethoxy group), tetrazolyl group, pyrazolyl group which may have a substituent, piperidylcarbonyl group which may have a substituent, pyrrolidinyl group, alkylsulfanyl groups which may have a substituent (wherein the alkyl group is preferably a $C_1$-$C_6$ straight-chained or branched alkyl groups, more preferably, methyl group, ethyl group, normal propyl group, isopropyl group, normal butyl group, isobutyl group, s-butyl group, t-butyl group, etc.), oxadiazolyl group which may have a substituent, and heterocyclic groups which may have a substituent (wherein the heterocyclic group is preferably a 5-10 membered heterocyclic group containing 1-3 heteroatoms (e.g., sulfur atom, oxygen atom, nitrogen atom, etc.), more preferably 3H-quinazoline-4-one, 2,4,5-trihydroisothiazole-1,1,3-trione, benzoimidazole and the like). As the substituent in amide groups, alkoxy groups, sulfonyl group, sulfamoyl group, amino groups, piperidyl group, pyrazolyl group, piperidylcarbonyl group, alkylsulfanyl groups, oxadiazolyl group and heterocyclic groups; and the acyl group, specific examples include, but are not limited to, those listed in Tables provided herein later.

As the "substituent" in the "nitrogen-containing heterocyclic group which may have a substituent" in $Z_a$, specific examples include, but are not limited to, saturated chain hydrocarbon groups (e.g., $C_1$-$C_6$ alkyl groups such as methyl, ethyl, propyl, isopropyl, butyl, isobutyl, s-butyl, t-butyl, pentyl, isopentyl, neopentyl, t-pentyl, 1-methylbutyl and hexyl), unsaturated chain hydrocarbon groups (e.g., $C_2$-$C_6$ alkenyl groups such as vinyl, allyl, 1-propenyl, isopropenyl, 1-butenyl, 2-butenyl and 3-methylallyl; and $C_2$-$C_6$ alkynyl groups such as ethynyl and 2-propynyl), alicyclic hydrocarbon groups (such as cyclohexyl, 1-cyclohexenyl and cyclohexylidene), and aromatic hydrocarbon groups (such as benzyl, tolyl and xylyl). The number of such substituent may be one or more.

As the "nitrogen-containing heterocyclic group" in the "nitrogen-containing heterocyclic group which may have a substituent" in $Z_a$, specific examples include, but are not limited to, nitrogen-containing 3-8 membered rings such as aziridine, azetidine, pyrrolidine, piperidine, hexamethyleneimine and heptamethyleneimine.

As the "hydrocarbon group" in the "amino group which may have a hydrocarbon group or an aromatic hydrocarbon group" in $Z_a$, specific examples include, but are not limited to, saturated chain hydrocarbon groups (e.g., $C_1$-$C_6$ alkyl groups such as methyl, ethyl, propyl, isopropyl, butyl, isobutyl, s-butyl, t-butyl, pentyl, isopentyl, neopentyl, t-pentyl, 1-methylbutyl and hexyl), unsaturated chain hydrocarbon groups (e.g., $C_2$-$C_6$ alkenyl groups such as vinyl, allyl, 1-propenyl, isopropenyl, 1-butenyl, 2-butenyl and 3-methylallyl; and $C_2$-$C_6$ alkynyl groups such as ethynyl and 2-propynyl), and alicyclic hydrocarbon groups (such as cyclohexyl, 1-cyclohexenyl and cyclohexylidene). As the aromatic hydrocarbon group, such as benzyl, tolyl, xylyl and the like may be given. The amino group may have one or more hydrocarbon groups and/or aromatic hydrocarbon groups.

As the "substituent" in the "nitrogen and oxygen-containing heterocyclic group which may have a substituent" in $Z_a$, specific examples include, but are not limited to, saturated chain hydrocarbon groups (e.g., $C_1$-$C_6$ alkyl groups such as methyl, ethyl, propyl, isopropyl, butyl, isobutyl, s-butyl, t-butyl, pentyl, isopentyl, neopentyl, t-pentyl, 1-methylbutyl and hexyl), unsaturated chain hydrocarbon groups (e.g., $C_2$-$C_6$ alkenyl groups such as vinyl, allyl, 1-propenyl, isopropenyl, 1-butenyl, 2-butenyl and 3-methylallyl; and $C_2$-$C_6$ alkynyl groups such as ethynyl and 2-propynyl), alicyclic hydrocarbon groups (such as cyclohexyl, 1-cyclohexenyl and cyclohexylidene), and aromatic hydrocarbon groups (such as benzyl, tolyl and xylyl). The number of such substituent may be one or more.

As the "nitrogen and oxygen-containing heterocyclic group" in the "nitrogen and oxygen-containing heterocyclic group which may have a substituent" in $Z_a$, specific examples include, but are not limited to, morpholine.

Those compounds represented by formula (Ia) may be prepared according to any of the methods disclosed in Schemes 1 to 4 in Preparation Examples provided later, or according to the method with necessary modifications.

The present invention also provides compounds represented by formula (Ia), pharmacologically acceptable salts thereof or pharmacologically acceptable ester thereof.

As specific examples of the compound represented by formula (Ia), those compounds represented by any of the following formulas may be given.

NCR-1

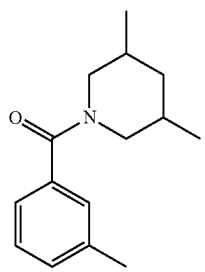

NCR-2

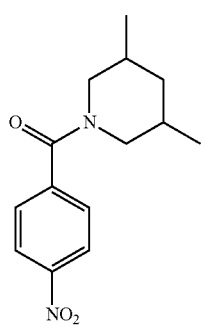

NCR-3

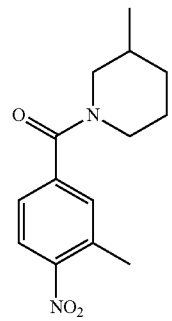

NCR-4

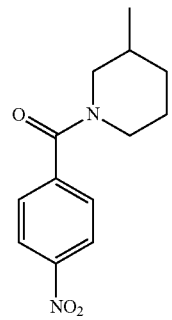

NCR-5

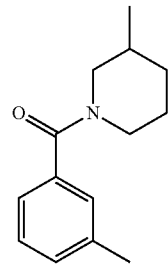

NCR-6

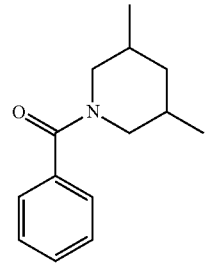

NCR-7

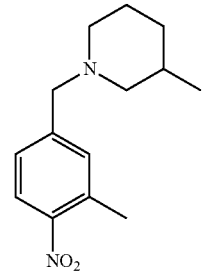

NCR-8
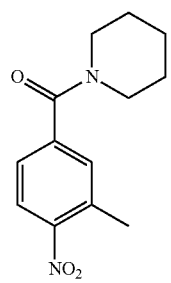
NCR-9
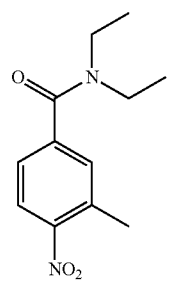
NCR-10
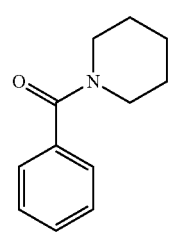
NCR-11
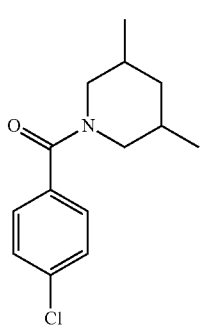
NCR-12
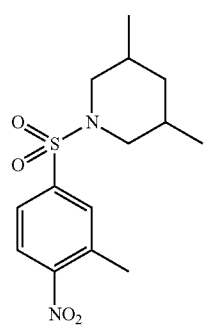
NCR-13
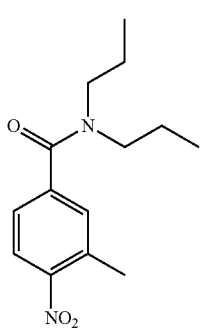
NCR-14
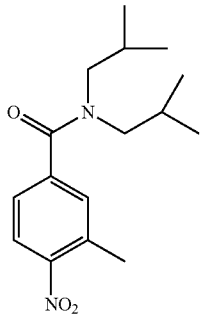
NCR-15
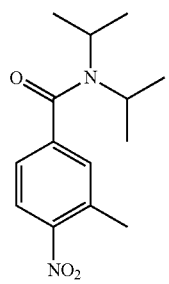
NCR-16
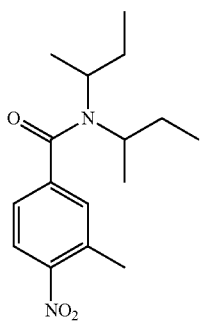
NCR-17
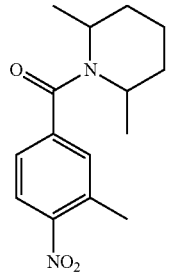

-continued

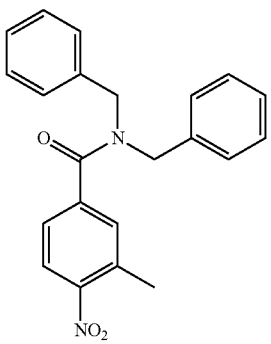

NCR-18

NCR-19

NCR-20

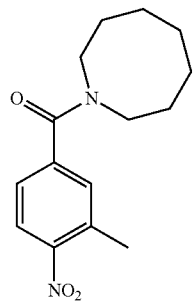

NCR-21

NCR-22

Commercially available compounds which are represented by formula (I) (excluding 3,5-dimethylpiperidyl 3-methyl-4-nitrophenyl ketone and 1-[4-(difluoromethoxy)phenyl]-2-(3,5-dimethylpiperidyl)ethan-1-one) are listed in the Tables below.

TABLE 1

Compound Sample
(Fit for the basic structure)

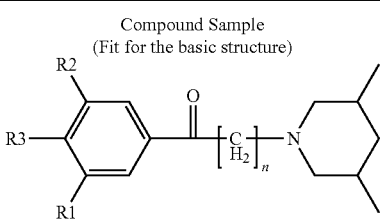

| Sample No | Supplier (Country) | ID Number | Name | n | $R^1$ | $R^2$ |
|---|---|---|---|---|---|---|
| 1 | Zelinsky (ART-CHEM) (Germany) | UZI/1846284 | N-{4-[(3,5-dimethylpiperidyl)carbonyl]phenyl} butanamide | 0 | H | H |
| 1 | Vitas-M (Russia) | STK167991 | N-{4-[(3,5-dimethylpiperidyl)carbonyl]phenyl} butanamide | 0 | H | H |
| 2 | Zelinsky (ART-CHEM) (Germany) | UZI/6203309 | 3,5-dimethylpiperidyl 4-chlorophenyl ketone | 0 | H | H |
| 2 | Vitas-M (Russia) | STK064998 | 3,5-dimethylpiperidyl 4-chlorophenyl ketone | 0 | H | H |
| 3 | Zelinsky (ART-CHEM) (Germany) | UZI/7104337 | 3,5-dimethylpiperidyl 4-ethoxyphenyl ketone | 0 | H | H |
| 3 | Vitas-M (Russia) | STK089384 | 3,5-dimethylpiperidyl 4-ethoxyphenyl ketone | 0 | H | H |

TABLE 1-continued

Compound Sample (Fit for the basic structure)

Structure: R2, R3, R1 substituted phenyl connected via C(=O)-(CH2)n-N(3,5-dimethylpiperidyl)

| | Supplier (Country) | ID Number | Name | n | R1 | R2 |
|---|---|---|---|---|---|---|
| 4 | Zelinsky (ART-CHEM) (Germany) | UZI/8010939 | 3,5-dimethylpiperidyl 4-phenylphenyl ketone | 0 | H | H |
| 4 | Vitas-M (Russia) | STK128213 | 3,5-dimethylpiperidyl 4-phenylphenyl ketone | 0 | H | H |

| Sample No | R³ | Chemical Formula | Molecular Weight |
|---|---|---|---|
| 1 | NHCO(CH$_2$)$_2$CH$_3$ | C$_{18}$H$_{26}$N$_2$O$_2$ | 302.41 |
| 1 | NHCO(CH$_2$)$_2$CH$_3$ | C$_{18}$H$_{26}$N$_2$O$_2$ | 302.41 |
| 2 | Cl | C$_{14}$H$_{18}$ClNO | 251.75 |
| 2 | Cl | C$_{14}$H$_{18}$ClNO | 251.75 |
| 3 | OCH$_2$CH$_3$ | C$_{16}$H$_{23}$NO$_2$ | 261.36 |
| 3 | OCH$_2$CH$_3$ | C$_{16}$H$_{23}$NO$_2$ | 261.36 |
| 4 | C$_6$H$_5$ | C$_{20}$H$_{23}$NO | 293.4 |
| 4 | C$_6$H$_5$ | C$_{20}$H$_{23}$NO | 293.4 |

TABLE 2

Compound Sample (Fit for the basic structure)

| Sample No | Supplier (Country) | ID Number | Name | n | R1 | R2 |
|---|---|---|---|---|---|---|
| 5 | ENAMINE (Ukraine) | T6039603 | 3,5-dimethylpiperidyl 4-methoxy-3-nitrophenyl ketone | 0 | H | NO$_2$ |
| 5 | Vitas-M (Russia) | STK099651 | 3,5-dimethylpiperidyl 4-methoxy-3-nitrophenyl ketone | 0 | H | NO$_2$ |
| 6 | Zelinsky (ART-CHEM) (Germany) | UZI/8022038 | 3,4-dimethylphenyl 3,5-dimethylpiperidyl ketone | 0 | H | CH$_3$ |
| 7 | Zelinsky (ART-CHEM) (Germany) | UZI/8037813 | 3,5-dimethylpiperidyl 4-methoxyphenyl ketone | 0 | H | H |
| 7 | Vitas-M (Russia) | STK008245 | 3,5-dimethylpiperidyl 4-methoxyphenyl ketone | 0 | H | H |
| 8 | Zelinsky (ART-CHEM) (Germany) | UZI/8062904 | 3,4-dichlorophenyl 3,5-dimethylpiperidyl ketone | 0 | H | Cl |
| 8 | Vitas-M (Russia) | STK019928 | 3,4-dichlorophenyl 3,5-dimethylpiperidyl ketone | 0 | H | Cl |
| 9 | Zelinsky (ART-CHEM) (Germany) | UZI/8075653 | 3,5-dimethylpiperidyl 4-fluorophenyl ketone | 0 | H | H |
| 9 | Vitas-M (Russia) | STK036338 | 3,5-dimethylpiperidyl 4-fluorophenyl ketone | 0 | H | H |

| Sample No | R³ | Chemical Formula | Molecular Weight |
|---|---|---|---|
| 5 | OCH$_3$ | C$_{15}$H$_{20}$N$_2$O$_4$ | 292.33 |
| 5 | OCH$_3$ | C$_{15}$H$_{20}$N$_2$O$_4$ | 292.33 |
| 6 | CH$_3$ | C$_{16}$H$_{23}$NO | 245.36 |

TABLE 2-continued

Compound Sample
(Fit for the basic structure)

| | | | |
|---|---|---|---|
| 7 | OCH$_3$ | C$_{15}$H$_{21}$NO$_2$ | 247.33 |
| 7 | OCH$_3$ | C$_{15}$H$_{21}$NO$_2$ | 247.33 |
| 8 | Cl | C$_{14}$H$_{17}$Cl$_2$NO | 286.2 |
| 8 | Cl | C$_{14}$H$_{17}$Cl$_2$NO | 286.2 |
| 9 | F | C$_{14}$H$_{18}$FNO | 235.3 |
| 9 | F | C$_{14}$H$_{18}$FNO | 235.3 |

TABLE 3

Compound Sample
(Fit for the basic structure)

| Sample No | Supplier (Country) | ID Number | Name | n | R$^1$ | R$^2$ |
|---|---|---|---|---|---|---|
| 10 | Zelinsky (ART-CHEM) (Germany) | UZI/8077610 | 3,5-dimethylpiperidyl 4-chloro-3-nitrophenyl ketone | 0 | H | NO$_2$ |
| 10 | Vitas-M (Russia) | STK072980 | 3,5-dimethylpiperidyl 4-chloro-3-nitrophenyl ketone | 0 | H | NO$_2$ |
| 11 | Vitas-M (Russia) | STK039793 | 3,5-dimethylpiperidyl 4-methylphenyl ketone | 0 | H | H |
| 12 | Vitas-M (Russia) | STK038754 | 3,5-dimethylpiperidyl 4-bromophenyl ketone | 0 | H | H |
| 12 | AsinexGold (Russia) | BAS 00623311 | 3,5-dimethylpiperidyl 4-bromophenyl ketone | 0 | H | H |
| 13 | Zelinsky (ART-CHEM) (Germany) | UZI/8109564 | N-{4-[(3,5dimethylpiperidyl)carbonyl]phenyl}acetamide | 0 | H | H |
| 13 | Vitas-M (Russia) | STK001156 | N-{4-[(3,5-dimethylpiperidyl)carbonyl]phenyl}acetamide | 0 | H | H |
| 14 | TimTec (USA) | ST008578 | 4-[(3,5-dimethylpiperidyl)carbonyl]phenyl acetate | 0 | H | H |

| Sample No | R$^3$ | Chemical Formula | Molecular Weight |
|---|---|---|---|
| 10 | Cl | C$_{14}$H$_{17}$ClN$_2$O$_3$ | 296.75 |
| 10 | Cl | C$_{14}$H$_{17}$ClN$_2$O$_3$ | 296.75 |
| 11 | CH$_3$ | C$_{15}$H$_{21}$NO | 231.33 |
| 12 | Br | C$_{14}$H$_{18}$BrNO | 296.2 |
| 12 | Br | C$_{14}$H$_{18}$BrNO | 296.2 |
| 13 | NHCOCH$_3$ | C$_{16}$H$_{22}$N$_2$O$_2$ | 274.36 |
| 13 | NHCOCH$_3$ | C$_{16}$H$_{22}$N$_2$O$_2$ | 274.36 |
| 14 | OCOCH$_3$ | C$_{16}$H$_{21}$NO$_3$ | 275.34 |

TABLE 4

Compound Sample (Fit for the basic structure)

$$\text{R3}\underset{\underset{R1}{|}}{\overset{\overset{R2}{|}}{\diagdown}}\text{C}_6\text{H}_2-\text{C}(=O)-(CH_2)_n-N(\text{3,5-dimethylpiperidyl})$$

| Sample No | Supplier (Country) | ID Number | Name | n | $R^1$ | $R^2$ |
|---|---|---|---|---|---|---|
| 15 | ENAMINE (Ukraine) | T6039629 | 3,5-dimethylpiperidyl 4-nitrophenyl ketone | 0 | H | H |
| 15 | Vitas-M (Russia) | STK057760 | 3,5-dimethylpiperidyl 4-nitrophenyl ketone | 0 | H | H |
| 16 | Zelinsky (ART-CHEM) (Germany) | UZI/8144985 | 3,5-dimethylpiperidyl 4-methyl-3-nitrophenyl ketone | 0 | H | $NO_2$ |
| 16 | Vitas-M (Russia) | STK100255 | 3,5-dimethylpiperidyl 4-methyl-3-nitrophenyl ketone | 0 | H | $NO_2$ |
| 17 | Zelinsky (ART-CHEM) (Germany) | UZI/8147502 | 4-(tert-butyl)phenyl 3,5-dimethylpiperidyl ketone | 0 | H | H |
| 17 | Vitas-M (Russia) | STK081887 | 4-(tert-butyl)phenyl 3,5-dimethylpiperidyl ketone | 0 | H | H |
| 18 | Zelinsky (ART-CHEM) (Germany) | UZI/8160409 | 3,5-dimethylpiperidyl 3,4,5-trimethoxyphenyl ketone | 0 | $OCH_3$ | $OCH_3$ |
| 18 | AsinexGold (Russia) | BAS 01130446 | 3,5-dimethylpiperidyl 3,4,5-trimethoxyphenyl ketone | 0 | $OCH_3$ | $OCH_3$ |

| Sample No | $R^3$ | Chemical Formula | Molecular Weight |
|---|---|---|---|
| 15 | $NO_2$ | $C_{14}H_{18}N_2O_3$ | 262.3 |
| 15 | $NO_2$ | $C_{14}H_{18}N_2O_3$ | 262.3 |
| 16 | $CH_3$ | $C_{15}H_{20}N_2O_3$ | 276.33 |
| 16 | $CH_3$ | $C_{15}H_{20}N_2O_3$ | 276.33 |
| 17 | $C(CH_3)_3$ | $C_{18}H_{27}NO$ | 273.41 |
| 17 | $C(CH_3)_3$ | $C_{18}H_{27}NO$ | 273.41 |
| 18 | $OCH_3$ | $C_{17}H_{25}NO_4$ | 307.38 |
| 18 | $OCH_3$ | $C_{17}H_{25}NO_4$ | 307.38 |

40

TABLE 5

Compound Sample (Fit for the basic structure)

$$\text{R3}\underset{\underset{R1}{|}}{\overset{\overset{R2}{|}}{\diagdown}}\text{C}_6\text{H}_2-\text{C}(=O)-(CH_2)_n-N(\text{3,5-dimethylpiperidyl})$$

| Sample No | Supplier (Country) | ID Number | Name | n | $R^1$ | $R^2$ |
|---|---|---|---|---|---|---|
| 19 | SPECS (Netherlands) | AF-399/41895463 | 3,5-dimethylpiperidyl 4-hexyloxyphenyl ketone | 0 | H | H |
| 19 | Princeton (USA) | OSSK_288718 | 3,5-dimethylpiperidyl 4-hexyloxyphenyl ketone | 0 | H | H |
| 19 | ASDI (USA) | 950015532 | 3,5-dimethylpiperidyl 4-hexyloxyphenyl ketone | 0 | H | H |
| 20 | Zelinsky (ART-CHEM) (Germany) | UZI/2314952 | N-{4-[(3,5-dimethylpiperidyl)carbonyl]phenyl}propanamide | 0 | H | H |
| 20 | Vitas-M (Russia) | STK204680 | N-{4-[(3,5-dimethylpiperidyl)carbonyl]phenyl}propanamide | 0 | H | H |
| 21 | Vitas-M (Russia) | STK131260 | N-{4-[(3,5dimethylpiperidyl)carbonyl]phenyl}-2-methylpropanamide | 0 | H | H |

TABLE 5-continued

Compound Sample
(Fit for the basic structure)

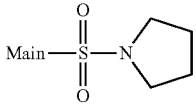

| | | | | | | |
|---|---|---|---|---|---|---|
| 21 | Princeton (USA) | OSSK_802625 | N-{4-[(3,5-dimethylpiperidyl)carbonyl]phenyl}-2-methylpropanamide | 0 | H | H |

| Sample No | $R^3$ | Chemical Formula | Molecular Weight |
|---|---|---|---|
| 19 | $O(CH_2)_5CH_3$ | $C_{20}H_{31}NO_2$ | 317.47 |
| 19 | $O(CH_2)_5CH_3$ | $C_{20}H_{31}NO_2$ | 317.47 |
| 19 | $O(CH_2)_5CH_3$ | $C_{20}H_{31}NO_2$ | 317.47 |
| 20 | $NHCOCH_2CH_3$ | $C_{17}H_{24}N_2O_2$ | 288.38 |
| 20 | $NHCOCH_2CH_3$ | $C_{17}H_{24}N_2O_2$ | 288.38 |
| 21 | $NHCOCH(CH_3)_2$ | $C_{18}H_{26}N_2O_2$ | 302.41 |
| 21 | $NHCOCH(CH_3)_2$ | $C_{18}H_{26}N_2O_2$ | 302.41 |

TABLE 6

Compound Sample
(Fit for the basic structure)

| Sample No | Supplier (Country) | ID Number | Name | n | $R^1$ | $R^2$ |
|---|---|---|---|---|---|---|
| 22 | AsinexGold (Russia) | BAS 00783988 | 3,4-dimethoxyphenyl 3,5-dimethylpiperidyl ketone | 0 | H | $OCH_3$ |
| 22 | SPECS (Netherlands) | AK-968/11658636 | 3,4-dimethoxyphenyl 3,5-dimethylpiperidyl ketone | 0 | H | $OCH_3$ |
| 22 | ASDI (USA) | 250005641 | 3,4-dimethoxyphenyl 3,5-dimethylpiperidyl ketone | 0 | H | $OCH_3$ |
| 23 | Chem T&I (Russia) | NSB 0011060 | 3,5-dimethylpiperidyl 4-(methylethyl)phenyl ketone | 0 | H | H |
| 24 | Chem T&I (Russia) | NSB 0014060 | 3,5-dimethylpiperidyl 3,4,5-triethoxyphenyl ketone | 0 | $OCH_2CH_3$ | $OCH_2CH_3$ |
| 25 | LifeChemicals (Ukraine) | F0412-0136 | 4-[(3,5-dimethylpiperidyl)carbonyl]benzenecarbonitrile | 0 | H | H |
| 26 | ENAMINE (Ukraine) | T0517-3789 | 3,5-dimethylpiperidyl 4-(trifluoromethyl)phenyl ketone | 0 | H | H |
| 27 | ENAMINE (Ukraine) | T6086857 | 3,5-dimethylpiperidyl 4-(pyrrolidinylsulfonyl)phenyl ketone | 0 | H | H |

| Sample No | $R^3$ | Chemical Formula | Molecular Weight |
|---|---|---|---|
| 22 | $OCH_3$ | $C_{16}H_{23}NO_3$ | 277.36 |
| 22 | $OCH_3$ | $C_{16}H_{23}NO_3$ | 277.36 |
| 22 | $OCH_3$ | $C_{16}H_{23}NO_3$ | 277.36 |
| 23 | $CH(CH_3)_2$ | $C_{17}H_{25}NO$ | 259.39 |
| 24 | $OCH_2CH_3$ | $C_{20}H_{31}NO_4$ | 349.46 |
| 25 | CN | $C_{15}H_{18}N_2O$ | 242.32 |
| 26 | $CF_3$ | $C_{15}H_{18}F_3NO$ | 285.3 |
| 27 | Main—S(=O)(=O)—N(pyrrolidine) | $C_{18}H_{26}N_2O_3S$ | 350.48 |

TABLE 7

Compound Sample
(Fit for the basic structure)

| Sample No | Supplier (Country) | ID Number | Name | n | R¹ | R² |
|---|---|---|---|---|---|---|
| 27 | UOS (Ukraine) | PB327301926 | 3,5-dimethylpiperidyl 4-(pyrrolidinylsulfonyl)phenyl ketone | 0 | H | H |
| 28 | LifeChemicals (Ukraine) | F0412-0130 | 4-[(dimethylamino)sulfonyl]phenyl 3,5-dimethylpiperidyl ketone | 0 | H | H |
| 29 | ENAMINE (Ukraine) | EN400-09530 | 4-(aminomethyl)phenyl 3,5-dimethylpiperidyl ketone | 0 | H | H |
| 30 | ENAMINE (Ukraine) | T5677980 | 3,5-dimethylpiperidyl 3-nitro-4-piperidylphenyl ketone | 0 | H | $NO_2$ |
| 31 | ENAMINE (Ukraine) | T5715818 | 3,5-dimethylpiperidyl 4-(4-methylpiperidyl)-3-nitrophenyl ketone | 0 | H | $NO_2$ |
| 32 | ENAMINE (Ukraine) | T5875122 | 3,5-dimethylpiperidyl 4-phenoxyphenyl ketone | 0 | H | H |
| 33 | Princeton (USA) | OSSK_810095 | 3,5-dimethylpiperidyl 4-[(4-chloropyrazolyl)methyl]phenyl ketone | 0 | H | H |
| 34 | ENAMINE (Ukraine) | T6184998 | 3,5-dimethylpiperidyl 3-chloro-4-hydroxyphenyl ketone | 0 | H | Cl |
| 35 | Vitas-M (Russia) | STK296851 | N-{4-[(3,5-dimethylpiperidyl)carbonyl]phenyl}benzamide | 0 | H | H |
| 35 | Princeton (USA) | OSSK_926474 | N-{4-[(3,5-dimethylpiperidyl)carbonyl]phenyl}benzamide | 0 | H | H |

| Sample No | R³ | Chemical Formula | Molecular Weight |
|---|---|---|---|
| 27 | Main—S(=O)(=O)—N(pyrrolidinyl) | $C_{18}H_{26}N_2O_3S$ | 350.48 |
| 28 | $SO_2N(CH_3)_2$ | $C_{16}H_{24}N_2O_3S$ | 324.44 |
| 29 | $CH_2NH_2$ | $C_{15}H_{22}N_2O$ | 246.35 |
| 30 | 4-methylpiperidyl-N—Main | $C_{19}H_{27}N_3O_3$ | 345.44 |
| 31 | piperidyl-N—Main | $C_{20}H_{29}N_3O_3$ | 359.46 |
| 32 | phenyl-O—Main | $C_{20}H_{23}NO_2$ | 309.4 |
| 33 | 4-chloropyrazolyl-CH₂—Main | $C_{18}H_{22}ClN_3O$ | 331.84 |
| 34 | OH | $C_{14}H_{18}ClNO_2$ | 267.75 |

TABLE 7-continued

Compound Sample
(Fit for the basic structure)

| Sample No | Structure | Chemical Formula | Molecular Weight |
|---|---|---|---|
| 35 | benzamide-N-Main | $C_{21}H_{24}N_2O_2$ | 336.43 |
| 35 | benzamide-N-Main | $C_{21}H_{24}N_2O_2$ | 336.43 |

TABLE 8

Compound Sample
(Fit for the basic structure)

| Sample No | Supplier (Country) | ID Number | Name | n | $R^1$ | $R^2$ |
|---|---|---|---|---|---|---|
| 36 | Chem T&I (Russia) | SER/0141547 | N-{4-[(3,5-dimethylpiperidyl)carbonyl]phenyl}(4-methylphenyl)carboxamide | 0 | H | H |
| 37 | Chem T&I (Russia) | SER/0141838 | N-{4-[(3,5-dimethylpiperidyl)carbonyl]phenyl}-2-furylcarboxamide | 0 | H | H |
| 38 | ENAMINE (Ukraine) | T5989827 | 3,5-dimethylpiperidyl 3-methoxy-4-(phenylmethoxy)phenyl ketone | 0 | $OCH_3$ | H |
| 39 | ENAMINE (Ukraine) | T6124051 | 3,5-dimethylpiperidyl 4-(phenylcarbonyl)phenyl ketone | 0 | H | H |
| 40 | Princeton (USA) | OSSK_931623 | 3,5-dimethylpiperidyl 4-[(prop-2-enylamino)sulfonyl]phenyl ketone | 0 | H | H |
| 41 | Princeton (USA) | OSSL_069057 | 3,5-dimethylpiperidyl 4-(pyrazolylmethyl)phenyl ketone | 0 | H | H |
| 42 | ENAMINE (Ukraine) | T6146953 | 3,5-dimethylpiperidyl 4-(1,2,4-triazolyl)phenyl ketone | 0 | H | H |
| 43 | ENAMINE (Ukraine) | T6151807 | 3,5-dimethylpiperidyl 4-Imidazolylphenyl ketone | 0 | H | H |
| 44 | ENAMINE (Ukraine) | T6154154 | methyl 4-[(3,5-dimethylpiperidyl)carbonyl]benzoate | 0 | H | H |

| Sample No | $R^3$ | Chemical Formula | Molecular Weight |
|---|---|---|---|
| 36 | 4-methylphenyl-C(O)-N-Main | $C_{22}H_{26}N_2O_2$ | 350.45 |

TABLE 8-continued

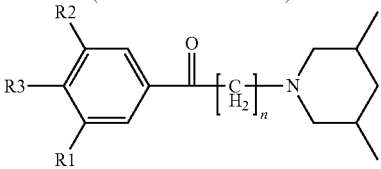

Compound Sample (Fit for the basic structure)

| 37 | 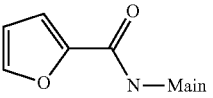 | C₁₉H₂₂N₂O₃ | 326.39 |
|---|---|---|---|
| 38 | 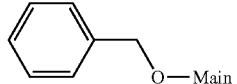 | C₂₂H₂₇NO₃ | 353.45 |
| 39 | 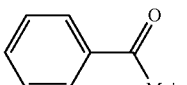 | C₂₁H₂₃NO₂ | 321.41 |
| 40 | SO₂NHCH₂CHCH₂ | C₁₇H₂₄N₂O₃S | 336.45 |
| 41 | 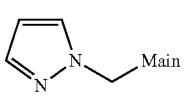 | C₁₈H₂₃N₃O | 297.39 |
| 42 | 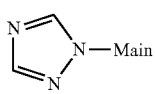 | C₁₆H₂₀N₄O | 284.36 |
| 43 | 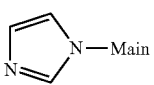 | C₁₇H₂₁N₃O | 283.37 |
| 44 | COOCH₃ | C₁₆H₂₁NO₃ | 275.34 |

TABLE 9

Compound Sample (Fit for the basic structure)

| Sample No | Supplier (Country) | ID Number | Name | n | R¹ | R² |
|---|---|---|---|---|---|---|
| 45 | ENAMINE (Ukraine) | T6244948 | amino-N-{4-[(3,5-dimethylpiperidyl)carbonyl]phenyl}amide | 0 | H | H |
| 46 | ENAMINE (Ukraine) | T6248261 | 3,5-dimethylpiperidyl 4-{2-[(methylsulfonyl)amino]ethyl}phenyl ketone | 0 | H | H |
| 47 | OTAVA (Ukraine) | 1159464 | 3,5-dimethylpiperidyl 4-(1,2,3,4-tetraazolyl)phenyl ketone | 0 | H | H |
| 48 | UOS (Ukraine) | PB184210594 | 3,5-dimethylpiperidyl 3-chloro-4,5-dimethoxyphenyl ketone | 0 | OCH₃ | Cl |
| 49 | UOS (Ukraine) | PB184211566 | N-{4-[(3,5-dimethylpiperidyl)carbonyl]phenyl}cyclopropylcarboxamide | 0 | H | H |
| 50 | UOS (Ukraine) | PB184211716 | 3,5-dimethylpiperidyl 4-(methylsulfonyl)phenyl ketone | 0 | H | H |

TABLE 9-continued

Compound Sample (Fit for the basic structure)

| 51 | UOS (Ukraine) | PB184213202 | 4,5-dimethyl-3-[(methylamino)sulfonyl]phenyl 3,5-dimethylpiperidyl ketone | 0 | SO$_2$NHCH$_3$ | CH$_3$ |
| 52 | UOS (Ukraine) | PB184213204 | 3-[(dimethylamino)sulfonyl]-4,5-dimethylphenyl 3,5-dimethylpiperidyl ketone | 0 | CH$_3$ | SO$_2$N(CH$_3$)$_2$ |
| 53 | UOS (Ukraine) | PB184213358 | 3,5-dimethylpiperidyl 4-pyrazolylphenyl ketone | 0 | H | H |

| Sample No | R$^3$ | Chemical Formula | Molecular Weight |
|---|---|---|---|
| 45 | NHCONH$_2$ | C$_{15}$H$_{21}$N$_3$O$_2$ | 275.35 |
| 46 | CH$_2$CH$_2$NHSO$_2$CH$_3$ | C$_{17}$H$_{26}$N$_2$O$_3$S | 338.46 |
| 47 | tetrazolyl—Main | C$_{15}$H$_{19}$N$_5$O | 285.34 |
| 48 | OCH$_3$ | C$_{16}$H$_{22}$ClNO$_3$ | 311.8 |
| 49 | cyclopropanecarbonyl-N—Main | C$_{18}$H$_{24}$N$_2$O$_2$ | 300.4 |
| 50 | SO$_2$CH$_3$ | C$_{15}$H$_{21}$NO$_3$S | 295.4 |
| 51 | CH$_3$ | C$_{17}$H$_{26}$N$_2$O$_3$S | 338.46 |
| 52 | CH$_3$ | C$_{18}$H$_{28}$N$_2$O$_3$S | 352.49 |
| 53 | pyrazolyl-N—Main | C$_{17}$H$_{21}$N$_3$O | 283.37 |

TABLE 10

Compound Sample (Fit for the basic structure)

| Sample No | Supplier (Country) | ID Number | Name | n | R$^1$ | R$^2$ |
|---|---|---|---|---|---|---|
| 54 | UOS (Ukraine) | PB184214520 | 3,5-dimethylpiperidyl 4-bromo-3,5-dimethoxyphenyl ketone | 0 | OCH$_3$ | OCH$_3$ |
| 55 (add1) | Zelinsky (ART-CHEM) (Germany) | UZI/8148542 | 3,5-dimethylpiperidyl 4-[(3,5-dimethylpiperidyl)carbonyl]phenyl ketone | 0 | H | H |
| 56 (add2) | AsinexGold (Russia) | BAS 03276131 | 3,5-dimethylpiperidyl 4-(phenylsulfonyl)phenyl ketone | 0 | H | H |
| 56 (add2) | TimTec (USA) | ST5271268 | 3,5-dimethylpiperidyl 4-(phenylsulfonyl)phenyl ketone | 0 | H | H |

TABLE 10-continued

Compound Sample
(Fit for the basic structure)

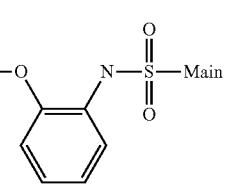

| | | | | | | |
|---|---|---|---|---|---|---|
| 57 (add3) | Asinex Platinum (Russia) | ASN 06365831 | 3,5-dimethylpiperidyl 4-{[4-(5-methylbenzotriazolyl)piperidyl]sulfonyl} phenyl ketone | 0 | H | H |
| 58 (add4) | ENAMINE (Ukraine) | T0505-2963 | 3,5-dimethylpiperidyl 3-nitro-4-pyrrolidinyl phenyl ketone | 0 | H | $NO_2$ |
| 59 (add5) | ENAMINE (Ukraine) | T0505-3770 | 3,5-dimethylpiperidyl 4-chloro-3-{[(2-methoxyphenyl)amino]sulfonyl} phenyl ketone | 0 | 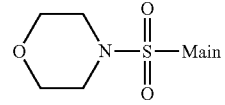 | H |
| 60 (add6) | ENAMINE (Ukraine) | T0505-7165 | 3,5-dimethylpiperidyl 4-bromo-3-(morpholin-4-ylsulfonyl) phenyl ketone | 0 | H | 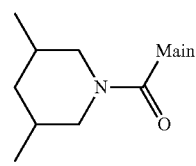 |

| Sample No | $R^3$ | Chemical Formula | Molecular Weight |
|---|---|---|---|
| 54 | Br | $C_{16}H_{22}BrNO_3$ | 356.25 |
| 55 (add1) | 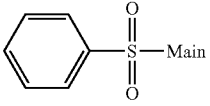 | $C_{22}H_{32}N_2O_2$ | 356.5 |
| 56 (add2) | 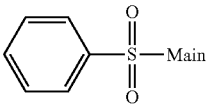 | $C_{20}H_{23}NO_3S$ | 357.47 |
| 56 (add2) | 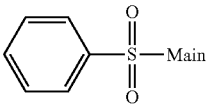 | $C_{20}H_{23}NO_3S$ | 357.47 |
| 57 (add3) | 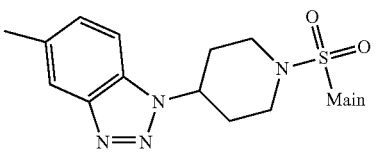 | $C_{26}H_{33}N_5O_3S$ | 495.64 |
| 58 (add4) | 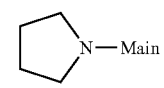 | $C_{18}H_{25}N_3O_3$ | 331.41 |
| 59 (add5) | Cl | $C_{21}H_{25}ClN_2O_4S$ | 436.95 |
| 60 (add6) | Br | $C_{18}H_{25}BrN_2O_4S$ | 445.37 |

TABLE 11

Compound Sample
(Fit for the basic structure)

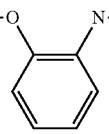

| Sample No | Supplier (Country) | ID Number | Name | n | R¹ | R² |
|---|---|---|---|---|---|---|
| 61 (add7) | ENAMINE (Ukraine) | T0505-8410 | 3,5-dimethylpiperidyl 3-{[(2-methoxyphenyl)amino]sulfonyl}-4-methylphenyl ketone | 0 |  | H |
| 62 (add8) | ENAMINE (Ukraine) | T5284681 | 5-({4-[(3,5-dimethylpiperidyl)carbonyl]phenyl}methylene)-3-(4-methylphenyl)-2-thioxo-1,3-diazolidin-4-one | 0 | H | H |
| 63 (add9) | LifeChemicals (Ukraine) | F0473-0330 | 3,5-dimethylpiperidyl 4-(2-1,2,3,4-tetrahydroisoquinolylsulfonyl)phenyl ketone | 0 | H | H |
| 64 (add10) | LifeChemicals (Ukraine) | F0715-0116 | 3,5-dimethylpiperidyl 4-[(diprop-2-enylamino)sulfonyl]phenyl ketone | 0 | H | H |
| 65 (add11) | ENAMINE (Ukraine) | T5891289 | 3,5-dimethylpiperidyl 4-[({[3-(trifluoromethyl)phenyl]sulfonyl}amino)methyl]phenyl ketone | 0 | H | H |
| 65 (add11) | UOS (Ukraine) | PB275100560 | 3,5-dimethylpiperidyl 4-[({[3-(trifluoromethyl)phenyl]sulfonyl}amino)methyl]phenyl ketone | 0 | H | H |
| 66 (add12) | ENAMINE (Ukraine) | T5891312 | 4-{[(2,5-dimethylphenyl)sulfonyl]amino}phenyl 3,5-dimethylpiperidyl ketone | 0 | H | H |
| 66 (add12) | UOS (Ukraine) | PB275099928 | 4-{[(2,5-dimethylphenyl)sulfonyl]amino}phenyl 3,5-dimethylpiperidyl ketone | 0 | H | H |

| Sample No | R³ | Chemical Formula | Molecular Weight |
|---|---|---|---|
| 61 (add7) | CH₃ | $C_{22}H_{28}N_2O_4S$ | 416.53 |
| 62 (add8) | 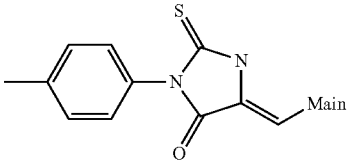 | $C_{25}H_{27}N_3O_2S$ | 433.57 |
| 63 (add9) | 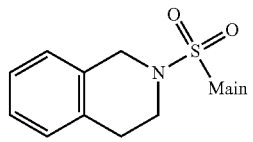 | $C_{23}H_{28}N_2O_3S$ | 412.55 |
| 64 (add10) | 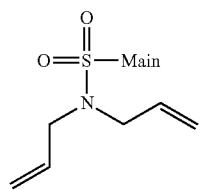 | $C_{20}H_{28}N_2O_3S$ | 376.51 |

TABLE 11-continued

Compound Sample (Fit for the basic structure)

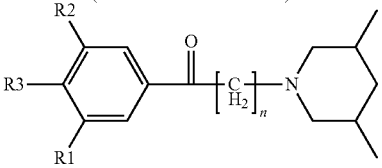

| | | | |
|---|---|---|---|
| 65 (add11) | 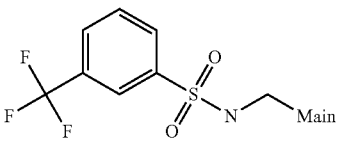 | $C_{22}H_{25}F_3N_2O_3S$ | 454.51 |
| 65 (add11) | 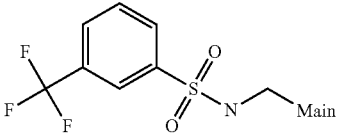 | $C_{22}H_{25}F_3N_2O_3S$ | 454.51 |
| 66 (add12) | 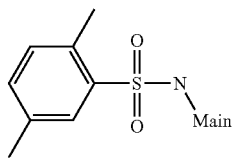 | $C_{22}H_{28}N_2O_3S$ | 400.53 |
| 66 (add12) | 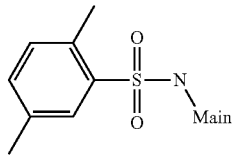 | $C_{22}H_{28}N_2O_3S$ | 400.53 |

TABLE 12

Compound Sample (Fit for the basic structure)

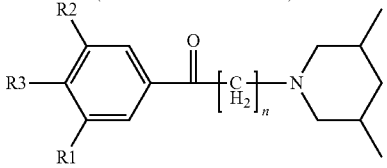

| Sample No | Supplier (Country) | ID Number | Name | n | R¹ | R² |
|---|---|---|---|---|---|---|
| 67 (add13) | ENAMINE (Ukraine) | T6178780 | 4-[(3,5-dimethylisoxazol-4-yl)methoxy]phenyl 3,5-dimethylpiperidyl ketone | 0 | H | H |
| 68 (add14) | ENAMINE (Ukraine) | T5889890 | 3,5-dimethylpiperidyl 4-{[(3-methoxyphenyl)sulfonyl]amino}phenyl ketone | 0 | H | H |
| 68 (add14) | UOS (Ukraine) | PB275102432 | 3,5-dimethylpiperidyl 4-{[(3-methoxyphenyl)sulfonyl]amino}phenyl ketone | 0 | H | H |
| 69 (add15) | ENAMINE (Ukraine) | T5891044 | 4-({[(2,5-dimethylphenyl)sulfonyl]amino}methyl)phenyl 3,5-dimethylpiperidyl ketone | 0 | H | H |
| 69 (add15) | UOS (Ukraine) | PB275100774 | 4-({[(2,5-dimethylphenyl)sulfonyl]amino}methyl)phenyl 3,5-dimethylpiperidyl ketone | 0 | H | H |

TABLE 12-continued

Compound Sample
(Fit for the basic structure)

[Structure: R2, R3, R1-substituted phenyl with C(=O)-[CH2]n-N(3,5-dimethylpiperidyl)]

| | | | | | | |
|---|---|---|---|---|---|---|
| 70 (add16) | ENAMINE T5621791 (Ukraine) | N-{4-[(3,5-dimethylpiperidyl)carbonyl]phenyl}-2-(4-oxo-2-pyrrolidinyl (1,3-thiazolin-5-yl))acetamide | | 0 | H | H |
| 71 (add17) | ENAMINE T5852810 (Ukraine) | 3,5-dimethylpiperidyl 4-[(4-methylpiperidyl)sulfonyl] phenyl ketone | | 0 | H | H |
| 72 (add18) | ENAMINE T5885590 (Ukraine) | 3,5-dimethylpiperidyl 4-[(ethylphenylamino)sulfonyl] phenyl ketone | | 0 | H | H |

| Sample No | R³ | Chemical Formula | Molecular Weight |
|---|---|---|---|
| 67 (add13) | [3,5-dimethylisoxazol-4-yl-methyleneoxy-Main] | $C_{20}H_{26}N_2O_3$ | 342.43 |
| 68 (add14) | [3-methoxyphenylsulfonyl-N-Main] | $C_{21}H_{26}N_2O_4S$ | 402.51 |
| 68 (add14) | [3-methoxyphenylsulfonyl-N-Main] | $C_{21}H_{26}N_2O_4S$ | 402.51 |
| 69 (add15) | [2,5-dimethylphenylsulfonyl-N-CH2-Main] | $C_{23}H_{30}N_2O_3S$ | 414.56 |
| 69 (add15) | [2,5-dimethylphenylsulfonyl-N-CH2-Main] | $C_{23}H_{30}N_2O_3S$ | 414.56 |
| 70 (add16) | [2-(pyrrolidin-1-yl)-4-oxo-thiazolin-5-yl-acetamido-Main] | $C_{23}H_{30}N_4O_3S$ | 442.57 |

TABLE 12-continued

| | Compound Sample (Fit for the basic structure) 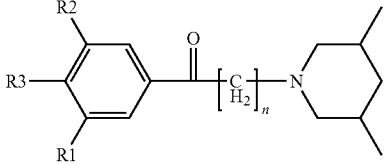 | | |
|---|---|---|---|
| 71 (add17) | 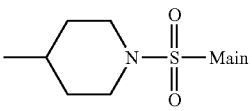 | C$_{20}$H$_{30}$N$_2$O$_3$S | 378.53 |
| 72 (add18) | 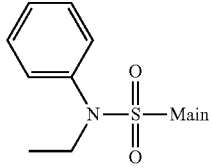 | C$_{22}$H$_{28}$N$_2$O$_3$S | 400.53 |

TABLE 13

Compound Sample (Fit for the basic structure)

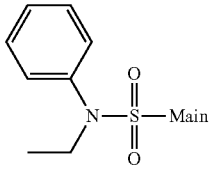

| Sample No | Supplier (Country) | ID Number | Name | n | R$^1$ | R$^2$ |
|---|---|---|---|---|---|---|
| 72 (add18) | UOS (Ukraine) | PB258783634 | 3,5-dimethylpiperidyl 4-[(ethylphenylamino)sulfonyl]phenyl ketone | 0 | H | H |
| 73 (add19) | Princeton (USA) | OSSK_810181 | 3,5-dimethylpiperidyl 4-[(4-bromopyrazolyl)methyl]phenyl ketone | 0 | H | H |
| 74 (add20) | Princeton (USA) | OSSK_810279 | 3,5-dimethylpiperidyl 4-[(4-bromo-3,5-dimethylpyrazolyl)methyl]phenyl ketone | 0 | H | H |
| 75 (add21) | Princeton (USA) | OSSK_824836 | 2-{4-[((3S,5R)-3,5-dimethylpiperidyl)carbonyl]phenyl}-2,4,5-trihydroisothiazole-1,1,3-trione | 0 | H | H |
| 76 (add22) | Princeton (USA) | OSSK_824897 | 2-{4-[((3S,5R)-3,5-dimethylpiperidyl)carbonyl]phenyl}-4-methyl-2,4,5-trihydroisothiazole-1,1,3-trione | 0 | H | H |
| 77 (add23) | Princeton (USA) | OSSK_824958 | 2-{4-[((3S,5R)-3,5-dimethylpiperidyl)carbonyl]phenyl)-4,4-dimethyl-2,4,5-trihydroisothiazole-1,1,3-trione | 0 | H | H |
| 78 (add24) | ENAMINE (Ukraine) | T5891124 | 4-[({[4-(tert-butyl)phenyl]sulfonyl}amino)methyl]phenyl 3,5-dimethylpiperidyl ketone | 0 | H | H |

| Sample No | R$^3$ | Chemical Formula | Molecular Weight |
|---|---|---|---|
| 72 (add18) | 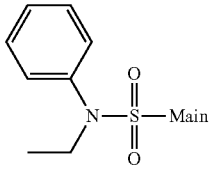 | C$_{22}$H$_{28}$N$_2$O$_3$S | 400.53 |

TABLE 13-continued
Compound Sample
(Fit for the basic structure)
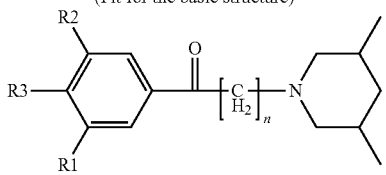
| | | | |
|---|---|---|---|
| 73 (add19) | 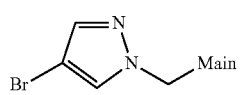 | C₁₈H₂₂BrN₃O | 376.29 |
| 74 (add20) | 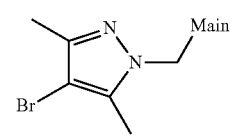 | C₂₀H₂₆BrN₃O | 404.34 |
| 75 (add21) | 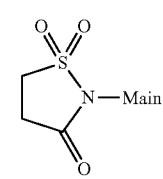 | C₁₇H₂₂N₂O₄S | 350.43 |
| 76 (add22) | 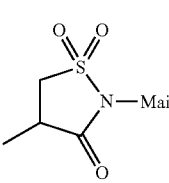 | C₁₈H₂₄N₂O₄S | 364.46 |
| 77 (add23) | 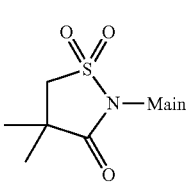 | C₁₉H₂₆N₂O₄S | 378.49 |
| 78 (add24) | 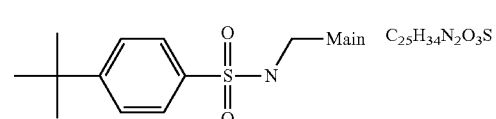 | C₂₅H₃₄N₂O₃S | 442.61 |
TABLE 14
Compound Sample
(Fit for the basic structure)
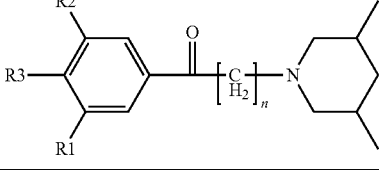
| Sample No | Supplier (Country) | ID Number | Name | n | R¹ | R² |
|---|---|---|---|---|---|---|
| 78 (add24) | UOS (Ukraine) | PB275102704 | 4-[({[4-(tert-butyl)phenyl]sulfonyl}amino)methyl]phenyl 3,5-dimethylpiperidyl ketone | 0 | H | H |

TABLE 14-continued

Compound Sample (Fit for the basic structure)

[Structure: R2, R3, R1 substituted benzene with C(=O)-(CH2)n-N(3,5-dimethylpiperidyl)]

| Sample No | Source | ID | Name | n | R1 | R2 |
|---|---|---|---|---|---|---|
| 79 (add25) | ENAMINE (Ukraine) | T5984447 | 4-{[(2,3-dimethylphenyl)amino]sulfonyl}phenyl 3,5-dimethylpiperidyl ketone | 0 | H | H |
| 80 (add26) | ENAMINE (Ukraine) | T5991171 | 3,5-dimethylpiperidyl 4-methyl-3-{[(4-methylphenyl)amino]sulfonyl}phenyl ketone | 0 | H | [4-methylphenyl-N(H)-S(=O)2-Main] |
| 81 (add27) | ENAMINE (Ukraine) | T5992247 | 3,5-dimethylpiperidyl 4-{[(4-methylphenyl)amino]sulfonyl}phenyl ketone | 0 | H | H |
| 81 (add27) | UOS (Ukraine) | PB291309174 | 3,5-dimethylpiperidyl 4-{[(4-methylphenyl)amino]sulfonyl}phenyl ketone | 0 | H | H |
| 82 (add28) | ENAMINE (Ukraine) | T5993116 | 3,5-dimethylpiperidyl 4-{[(4-fluorophenyl)amino]sulfonyl}phenyl ketone | 0 | H | H |
| 83 (add29) | ENAMINE (Ukraine) | T5996172 | 3,5-dimethylpiperidyl 4-[(2-methyl(1,3-thiazol-4-yl))methylthio]phenyl ketone | 0 | H | H |
| 84 (add30) | ENAMINE (Ukraine) | T5997889 | 4-[(2H,3H-benzo[3,4-e]1,4-dioxin-6-ylsulfonyl)amino]phenyl 3,5-dimethylpiperidyl ketone | 0 | H | H |
| 85 (add31) | ENAMINE (Ukraine) | T6053107 | 3,5-dimethylpiperidyl 4-[(6-methyl(4-hydroimidazo[1,2-a]pyridin-2-yl))methoxy]phenyl ketone | 0 | H | H |

| Sample No | R3 | Chemical Formula | Molecular Weight |
|---|---|---|---|
| 78 (add24) | [4-tert-butylphenyl-S(=O)2-N(H)-CH2-Main] | C25H34N2O3S | 442.61 |
| 79 (add25) | [2,3-dimethylphenyl-N(H)-S(=O)2-Main] | C22H28N2O3S | 400.53 |
| 80 (add26) | CH3 | C22H28N2O3S | 400.53 |
| 81 (add27) | [4-methylphenyl-N(H)-S(=O)2-Main] | C21H26N2O3S | 386.51 |

TABLE 14-continued

Compound Sample (Fit for the basic structure)

| No | Structure | Formula | MW |
|---|---|---|---|
| 81 (add27) | 4-methylphenyl-N-sulfonyl-Main | C₂₁H₂₆N₂O₃S | 386.51 |
| 82 (add28) | 4-fluorophenyl-N-sulfonyl-Main | C₂₀H₂₃FN₂O₃S | 390.47 |
| 83 (add29) | 2-methylthiazol-4-yl-methyl-S-Main | C₁₉H₂₄N₂OS₂ | 360.54 |
| 84 (add30) | 2,3-dihydrobenzo[b][1,4]dioxin-6-yl-sulfonyl-N-Main | C₂₂H₂₆N₂O₅S | 430.52 |
| 85 (add31) | 6-methylimidazo[1,2-a]pyridin-2-yl-methoxy-Main | C₂₃H₂₇N₃O₂ | 377.48 |

TABLE 15

Compound Sample (Fit for the basic structure)

| Sample No | Supplier (Country) | ID Number | Name | n | R¹ | R² |
|---|---|---|---|---|---|---|
| 86 (add32) | ENAMINE (Ukraine) | T6055225 | 3,5-dimethylpiperidyl 4-[(5-methyl(1,2,4-oxadiazol-3-yl))methoxy]phenyl ketone | 0 | H | H |
| 87 (add33) | ENAMINE (Ukraine) | T6232627 | 3,5-dimethylpiperidyl 4-(1,2,3,4-tetrahydroquinolylsulfonyl)phenyl ketone | 0 | H | H |
| 88 (add34) | ENAMINE (Ukraine) | T6101662 | 3,5-dimethylpiperidyl 4-{[(4-ethoxyphenyl)amino]sulfonyl}phenyl ketone | 0 | H | H |
| 88 (add34) | UOS (Ukraine) | PB184214142 | 3,5-dimethylpiperidyl 4-{[(4-ethoxyphenyl)amino]sulfonyl}phenyl ketone | 0 | H | H |
| 89 (add35) | ENAMINE (Ukraine) | T6114600 | 3,5-dimethylpiperidyl 4-{[(4-fluorophenyl)sulfonyl]amino}phenyl ketone | 0 | H | H |

TABLE 15-continued

Compound Sample
(Fit for the basic structure)

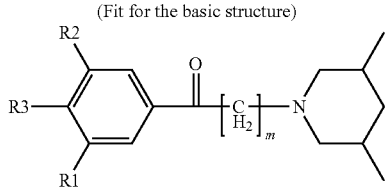

| Sample No | | | | | m | R1 | R2 |
|---|---|---|---|---|---|---|---|
| 90 (add36) | Princeton (USA) | OSSL__069022 | 3,5-dimethylpiperidyl 4-[(4-chloro-3,5-dimethylpyrazolyl)methyl] phenyl ketone | | 0 | H | H |
| 91 (add37) | Zelinsky (ART-CHEM) (Germany) | UZI/2518327 | 3,5-dimethylpiperidyl 4-(5-phenyl(1,3,4-oxadiazol-2-yl)) phenyl ketone | | 0 | H | H |

| Sample No | $R^3$ | Chemical Fomula | Molecular Weight |
|---|---|---|---|
| 86 (add32) | | $C_{18}H_{23}N_3O_3$ | 329.39 |
| 87 (add33) | | $C_{23}H_{28}N_2O_3S$ | 412.55 |
| 88 (add34) | | $C_{22}H_{28}N_2O_4S$ | 416.53 |
| 88 (add34) | | $C_{22}H_{28}N_2O_4S$ | 416.53 |
| 89 (add35) | | $C_{20}H_{23}FN_2O_3S$ | 390.47 |
| 90 (add36) | | $C_{20}H_{26}ClN_3O$ | 359.89 |
| 91 (add37) | | $C_{22}H_{23}N_3O_2$ | 361.44 |

TABLE 16

Compound Sample
(Fit for the basic structure)

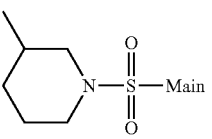

| Sample No | Supplier (Country) | ID Number | Name | n | R¹ | R² |
|---|---|---|---|---|---|---|
| 92 (add38) | ENAMINE (Ukraine) | T6131058 | 3,5-dimethylpiperidyl 4-{[(2-methoxyethyl)amino]sulfonyl}phenyl ketone | 0 | H | H |
| 93 (add39) | ENAMINE (Ukraine) | T6132785 | 4-(benzimidazol-2-ylthiomethyl)phenyl 3,5-dimethylpiperidyl ketone | 0 | H | H |
| 93 (add39) | UOS (Ukraine) | PB184210580 | 4-(benzimidazol-2-ylthiomethyl)phenyl 3,5-dimethylpiperidyl ketone | 0 | H | H |
| 94 (add40) | ENAMINE (Ukraine) | T6142049 | 3,5-dimethylpiperidyl 4-chloro-3-[(3-methylpiperidyl)sulfonyl]phenyl ketone | 0 | 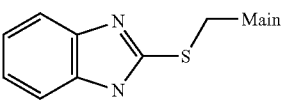 | H |
| 95 (add41) | ENAMINE (Ukraine) | T6151070 | 3,5-dimethylpiperidyl 4-[(phenylsulfonyl)amino]phenyl ketone | 0 | H | H |
| 96 (add42) | ENAMINE (Ukraine) | T6154735 | 3-{4-[(3,5-dimethylpiperidyl)carbonyl]phenyl}-2-methyl-3-hydroquinazolin-4-one | 0 | H | H |
| 97 (add43) | ENAMINE (Ukraine) | T6182050 | 4-({4-[(3,5-dimethylpiperidyl)carbonyl]phenyl}sulfonyl)piperazin-2-one | 0 | H | H |
| 98 (add44) | ENAMINE (Ukraine) | T6186857 | N-{4-[(3,5-dimethylpiperidyl)carbonyl]phenyl}-2-thienylcarboxamide | 0 | H | H |

| Sample No | R³ | Chemical Fomula | Molecular Weight |
|---|---|---|---|
| 92 (add38) | SO₂NHCH₂CH₂OCH₃ | $C_{17}H_{26}N_2O_4S$ | 354.46 |
| 93 (add39) | 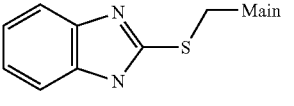 | $C_{22}H_{25}N_3OS$ | 379.52 |
| 93 (add39) | 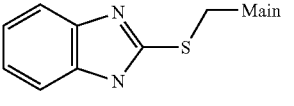 | $C_{22}H_{25}N_3OS$ | 379.52 |
| 94 (add40) | Cl | $C_{20}H_{29}ClN_2O_3S$ | 412.97 |
| 95 (add41) | 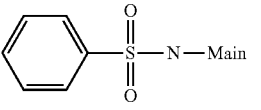 | $C_{20}H_{24}N_2O_3S$ | 372.48 |
| 96 (add42) | 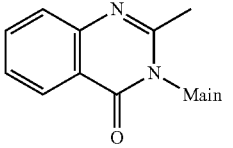 | $C_{23}H_{25}N_3O_2$ | 375.46 |

TABLE 16-continued

Compound Sample
(Fit for the basic structure)

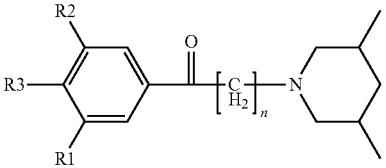

| 97 (add43) | 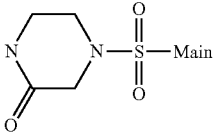 | C$_{18}$H$_{25}$N$_{3}$O$_{4}$S | 379.47 |
| 98 (add44) | 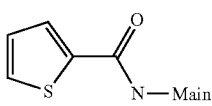 | C$_{19}$H$_{22}$N$_{2}$O$_{2}$S | 342.46 |

TABLE 17

Compound Sample
(Fit for the basic structure)

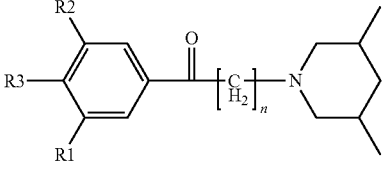

| Sample No | Supplier (Country) | ID Number | Name | n | R$^1$ | R$^2$ |
|---|---|---|---|---|---|---|
| 98 (add44) | UOS (Ukraine) | PB184213386 | N-{4-[(3,5-dimethylpiperidyl)carbonyl]phenyl}-2-thienylcarboxamide | 0 | H | H |
| 99 (add45) | ENAMINE (Ukraine) | T6190262 | 3,5-dimethylpiperidyl 4-methyl-3-(piperidylsulfonyl)phenyl ketone | 0 | H | 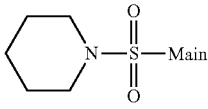 |
| 100 (add46) | ENAMINE (Ukraine) | T5768807 | 3,5-dimethylpiperidyl 4-(piperidylsulfonyl)phenyl ketone | 0 | H | H |
| 100 (add46) | UOS (Ukraine) | PB234963720 | 3,5-dimethylpiperidyl 4-(piperidylsulfonyl)phenylketone | 0 | H | H |
| 101 (add47) | LifeChemicals (Ukraine) | F0440-0309 | 3,5-dimethylpiperidyl 4-[(3,5-dimethylpiperidyl)sulfonyl]phenyl ketone | 0 | H | H |
| 102 (add48) | UOS (Ukraine) | PB184212112 | 3,5-dimethylpiperidyl 4-(4-chloro-3,5-dimethylpyrazolyl)phenyl ketone | 0 | H | H |
| 103 (add49) | UOS (Ukraine) | PB184212166 | 3,5-dimethylpiperidyl 4-chloro-3-(piperidylsulfonyl)phenyl ketone | 0 | H | 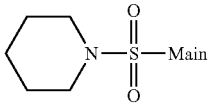 |
| 104 (add50) | UOS (Ukraine) | PB184213526 | 4-benzimidazolylphenyl 3,5-dimethylpiperidyl ketone | 0 | H | H |

TABLE 17-continued
Compound Sample
(Fit for the basic structure)
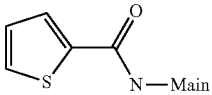
| Sample No | R³ | Chemical Fomula | Molecular Weight |
|---|---|---|---|
| 98 (add44) | 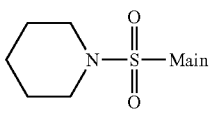 | $C_{19}H_{22}N_2O_2S$ | 342.46 |
| 99 (add45) | CH₃ | $C_{20}H_{30}N_2O_3S$ | 378.53 |
| 100 (add46) | 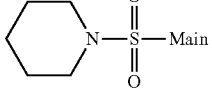 | $C_{19}H_{28}N_2O_3S$ | 364.5 |
| 100 (add46) | 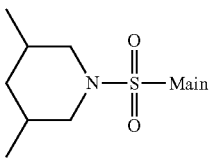 | $C_{19}H_{28}N_2O_3S$ | 364.5 |
| 101 (add47) | 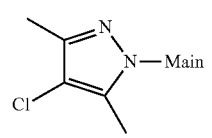 | $C_{21}H_{32}N_2O_3S$ | 392.56 |
| 102 (add46) | 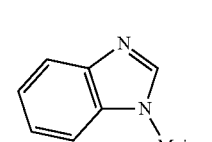 | $C_{19}H_{24}ClN_3O$ | 345.87 |
| 103 (add49) | Cl | $C_{19}H_{27}ClN_2O_3S$ | 398.95 |
| 104 (add50) |  | $C_{21}H_{23}N_3O$ | 333.43 |

TABLE 18

Compound Sample
(Fit for the basic structure)

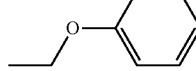

| Sample No | Supplier (Country) | ID Number | Name | n | R¹ | R² |
|---|---|---|---|---|---|---|
| 105 (add51) | UOS (Ukraine) | PB184214076 | 3,5-dimethylpiperidyl 4-chloro-3-{[(4-ethoxyphenyl)amino]sulfonyl}phenyl ketone | 0 | 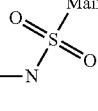 Main | H |
| 106 (add52) | UOS (Ukraine) | PB184215230 | 3,5-dimethylpiperidyl 4-{[(4-fluoro-3-methylphenyl)sulfonyl]amino}phenyl ketone | 0 | H | H |

| Sample No | R³ | Chemical Fomula | Molecular Weight |
|---|---|---|---|
| 105 (add51) | Cl | $C_{22}H_{27}ClN_2O_4S$ | 450.98 |
| 106 (add52) | 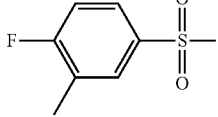 Main | $C_{21}H_{25}FN_2O_3S$ | 404.5 |

TABLE 19

1

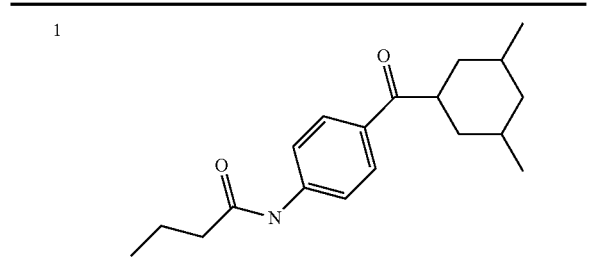

2

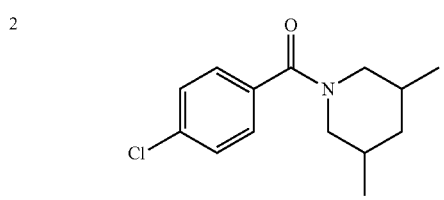

3

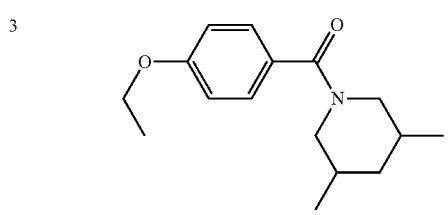

TABLE 19-continued

4

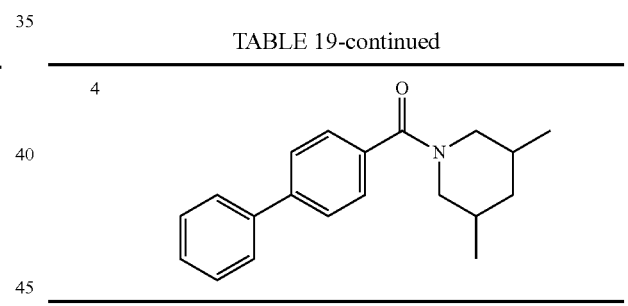

TABLE 20

5

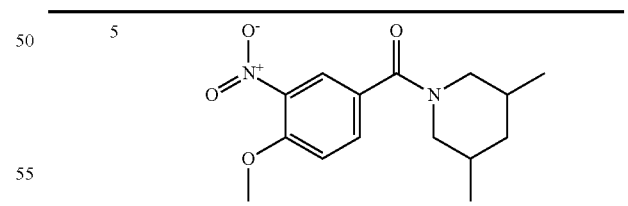

6

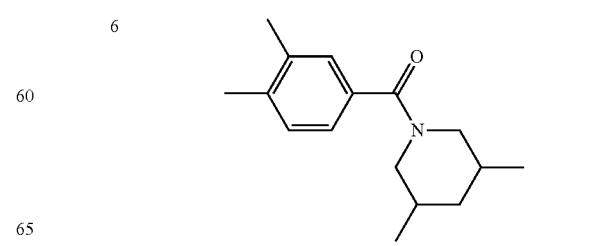

TABLE 20-continued
7 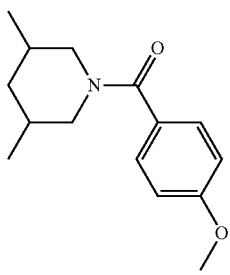 [SMILES: COc1ccc(C(=O)N2CC(C)CC(C)C2)cc1]
8 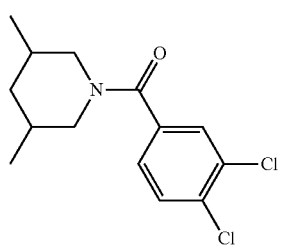 [SMILES: CC1CC(C)CN(C(=O)c2ccc(Cl)c(Cl)c2)C1]
TABLE 21
9 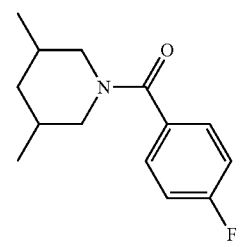 [SMILES: CC1CC(C)CN(C(=O)c2ccc(F)cc2)C1]
10 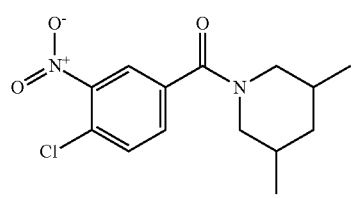 [SMILES: CC1CC(C)CN(C(=O)c2ccc(Cl)c([N+](=O)[O-])c2)C1]
11 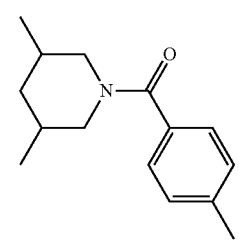 [SMILES: Cc1ccc(C(=O)N2CC(C)CC(C)C2)cc1]
12 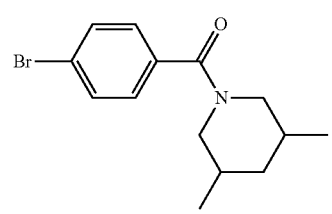 [SMILES: CC1CC(C)CN(C(=O)c2ccc(Br)cc2)C1]
TABLE 22
13 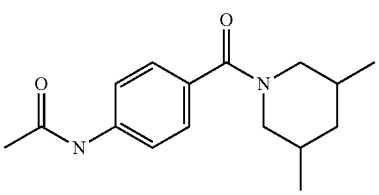 [SMILES: CC(=O)Nc1ccc(C(=O)N2CC(C)CC(C)C2)cc1]
14 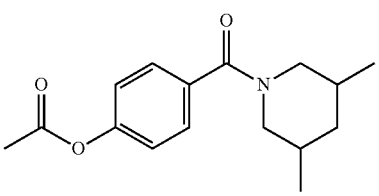 [SMILES: CC(=O)Oc1ccc(C(=O)N2CC(C)CC(C)C2)cc1]
15 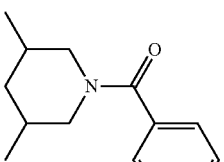
16 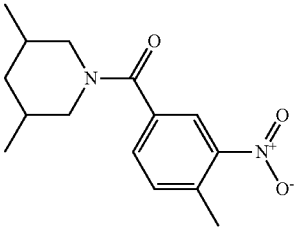 [SMILES: Cc1ccc(C(=O)N2CC(C)CC(C)C2)cc1[N+](=O)[O-]]
TABLE 23
17 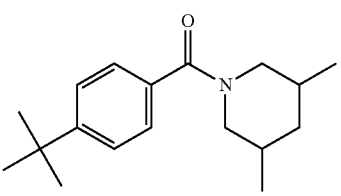 [SMILES: CC1CC(C)CN(C(=O)c2ccc(C(C)(C)C)cc2)C1]
18 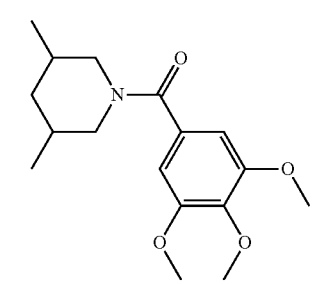 [SMILES: COc1cc(C(=O)N2CC(C)CC(C)C2)cc(OC)c1OC]

TABLE 23-continued
19 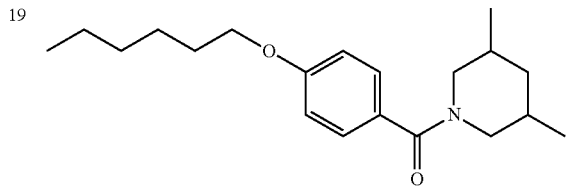
20 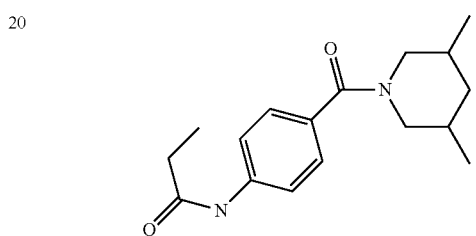
TABLE 24
21 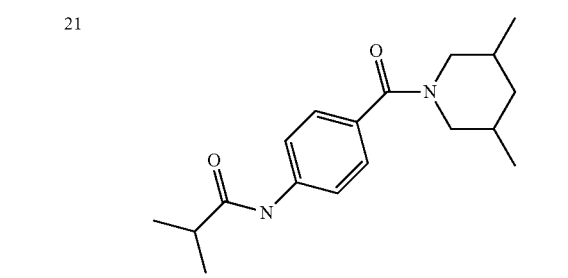
22 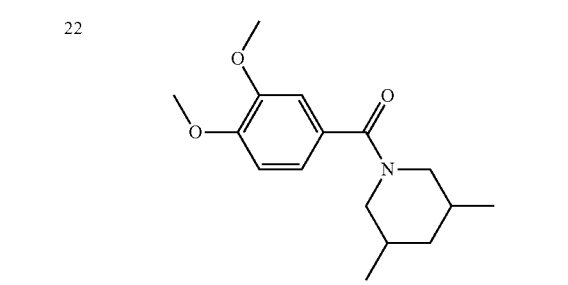
23 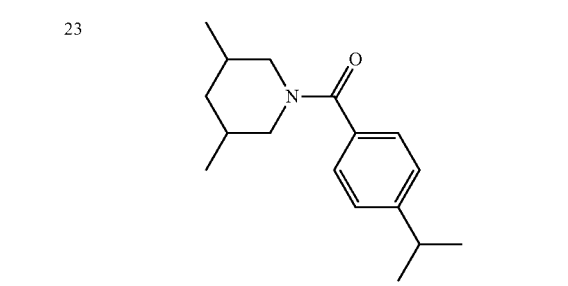
TABLE 24-continued
24 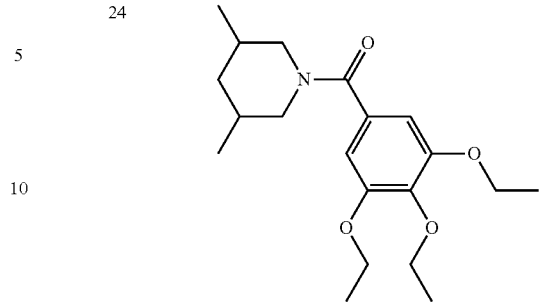
25 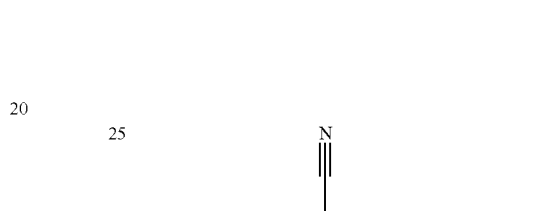
26 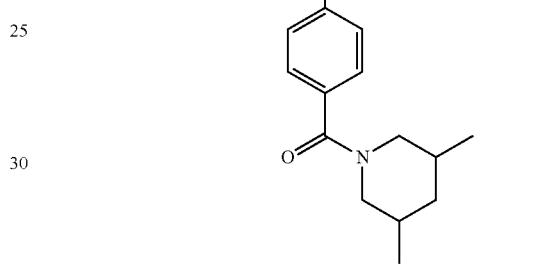
TABLE 25
27 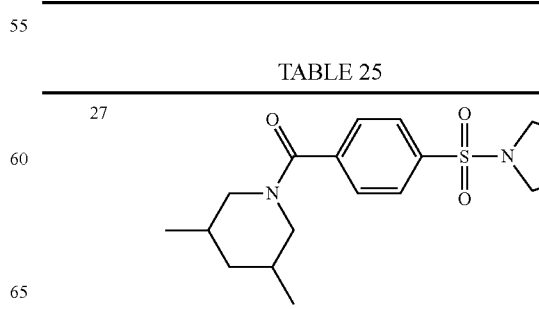

TABLE 25-continued
| 28 | 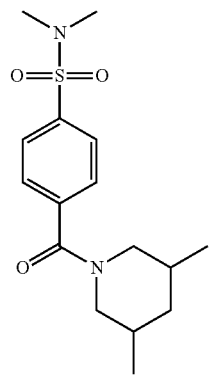 |
|---|---|
| 29 | 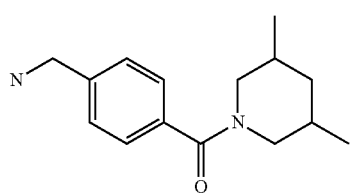 [SMILES: CC1CC(C)CN(C(=O)c2ccc(CN)cc2)C1] |
| 30 | 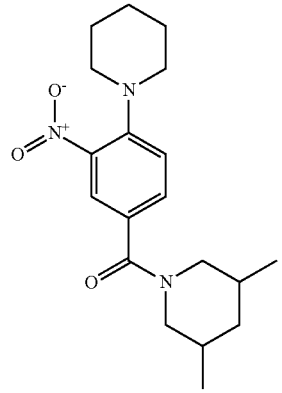 [SMILES: CC1CC(C)CN(C(=O)c2ccc(N3CCCCC3)c([N+](=O)[O-])c2)C1] |
TABLE 26
| 31 | 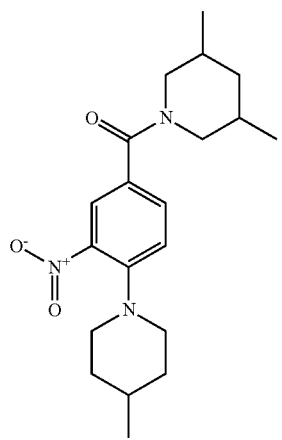 [SMILES: CC1CCN(c2ccc(C(=O)N3CC(C)CC(C)C3)cc2[N+](=O)[O-])CC1] |
|---|---|
| 32 | 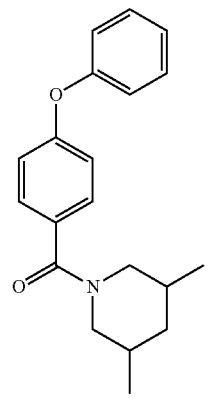 [SMILES: CC1CC(C)CN(C(=O)c2ccc(Oc3ccccc3)cc2)C1] |
TABLE 26-continued
| 33 | |
|---|---|
| 34 | 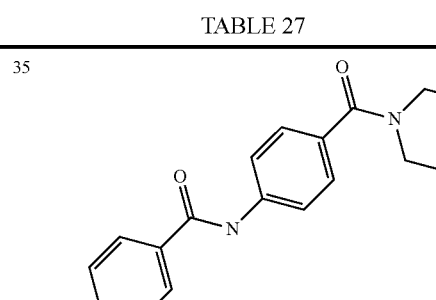 |
TABLE 27
| 35 | 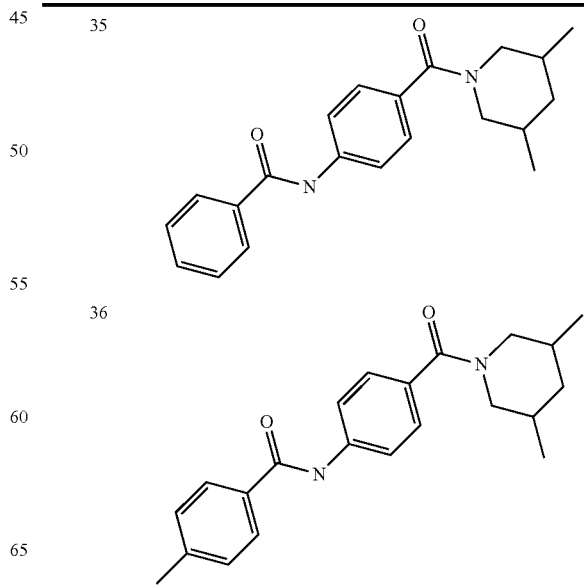 |
|---|---|
| 36 | |

TABLE 27-continued
37 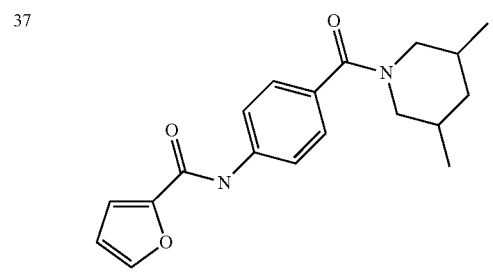
38 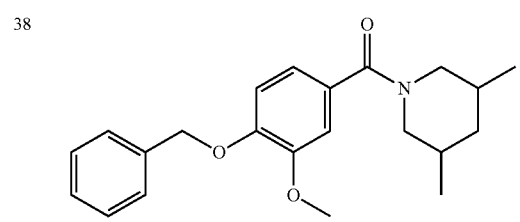
39 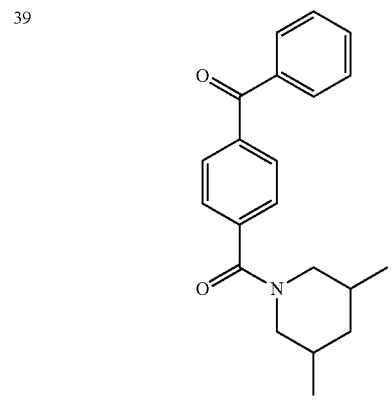
40 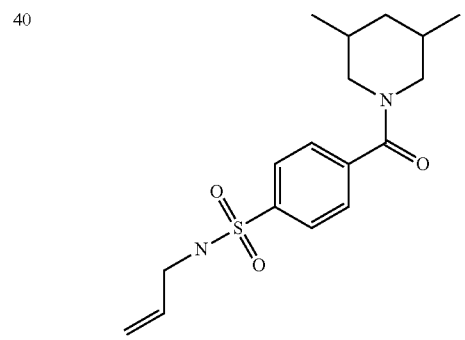
TABLE 28
41 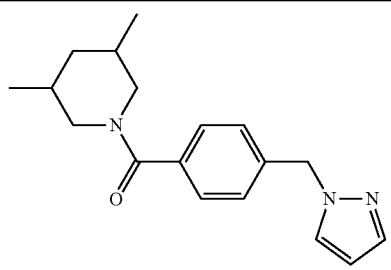
TABLE 28-continued
42 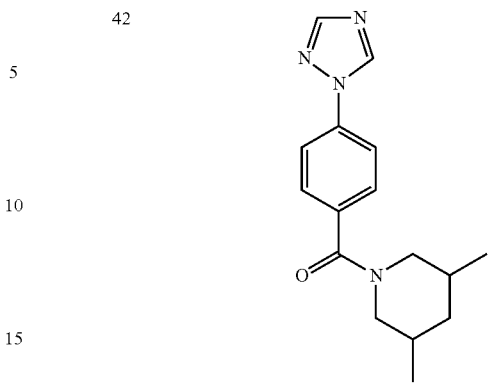
43 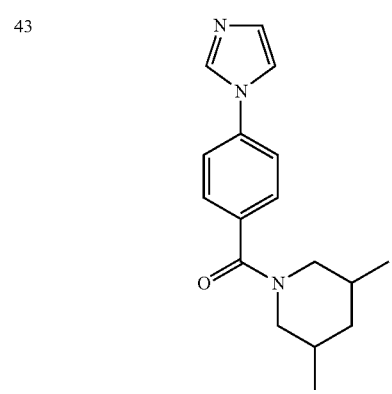
44 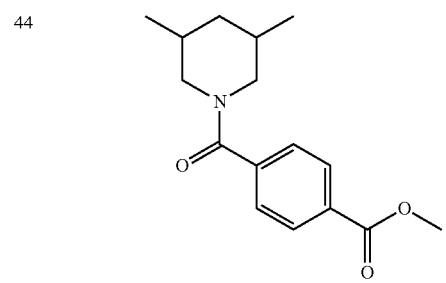
45 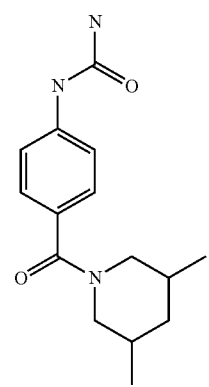 [SMILES: CC1CC(C)CN(C(=O)c2ccc(NC(N)=O)cc2)C1]

TABLE 29
46 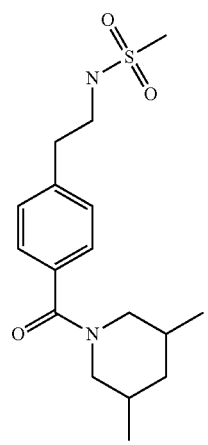 [SMILES: CC1CC(C)CN(C(=O)c2ccc(CCNS(C)(=O)=O)cc2)C1]
47 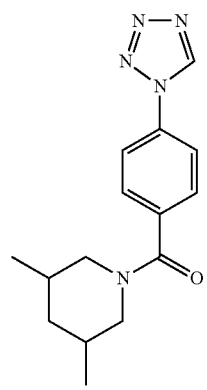 [SMILES: CC1CC(C)CN(C(=O)c2ccc(-n3cnnn3)cc2)C1]
48 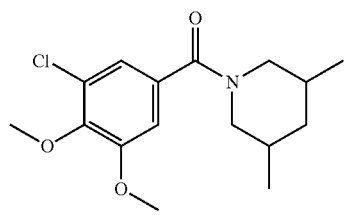
49 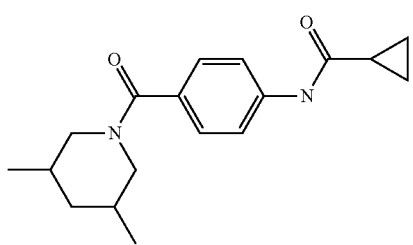 [SMILES: CC1CC(C)CN(C(=O)c2ccc(NC(=O)C3CC3)cc2)C1]
TABLE 30
50 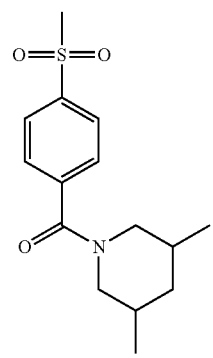 [SMILES: CC1CC(C)CN(C(=O)c2ccc(S(C)(=O)=O)cc2)C1]
51 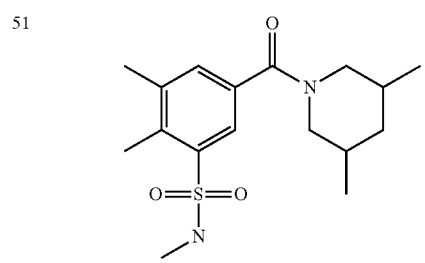
52 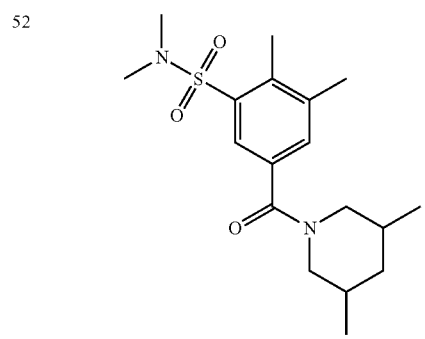
53 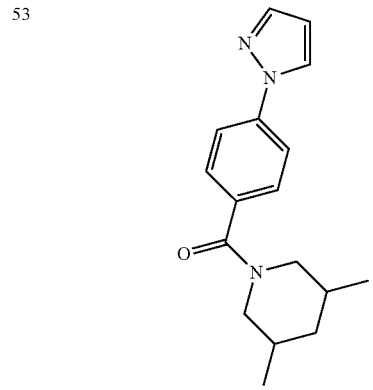
TABLE 31
54 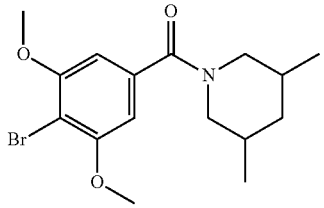 [SMILES: COc1cc(C(=O)N2CC(C)CC(C)C2)cc(OC)c1Br]

| TABLE 31-continued | |
|---|---|
| 55 (add 1) | 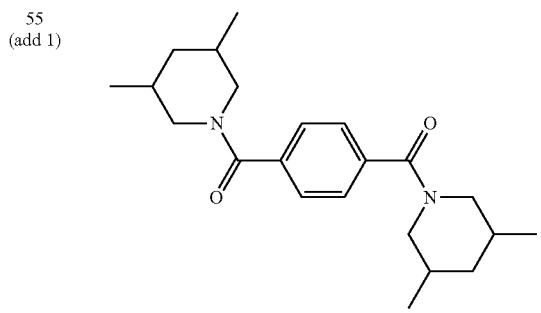 |
| 56 (add 2) | 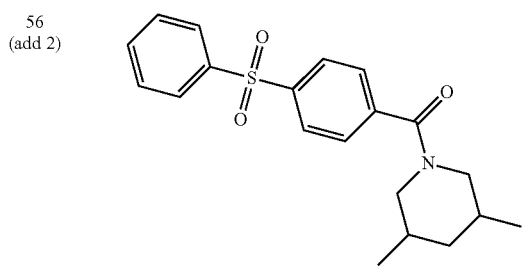 |
| 57 (add 3) | 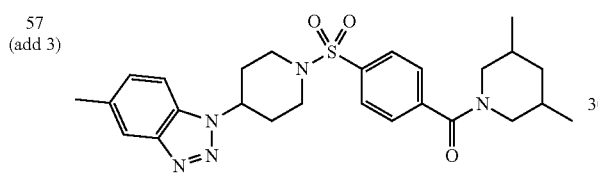 |
| TABLE 32 | |
|---|---|
| 58 (add 4) | 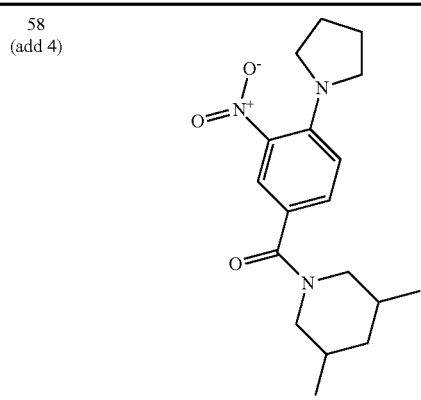 |
| 59 (add 5) | 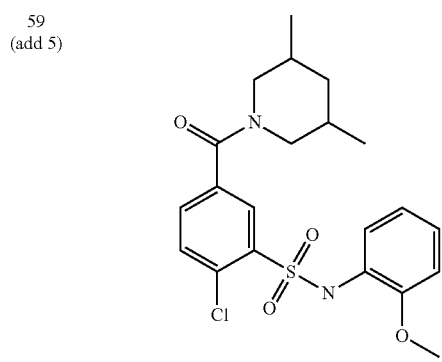 |
| TABLE 32-continued | |
|---|---|
| 60 (add 6) | 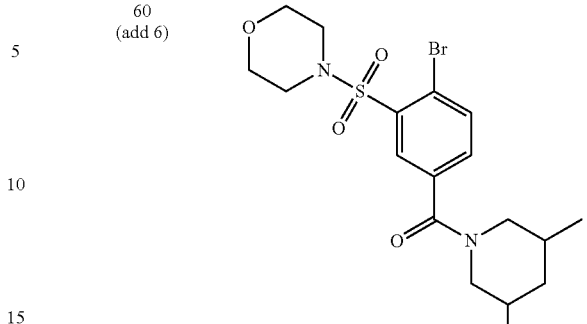 |
| 61 (add 7) | 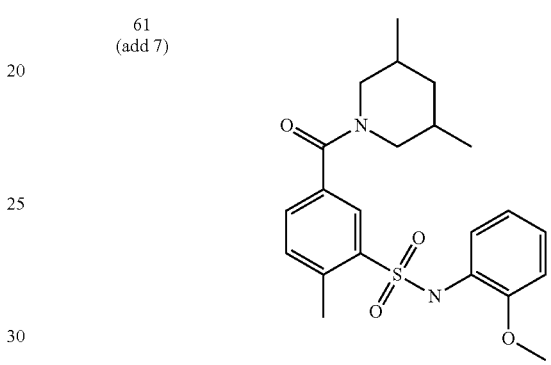 |
| TABLE 33 | |
|---|---|
| 62 (add 8) | 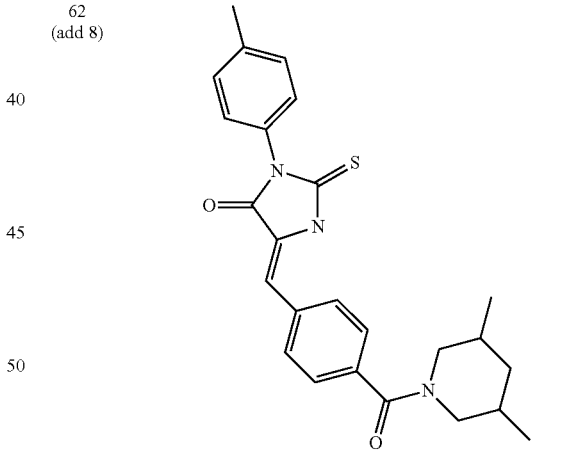 |
| 63 (add 9) | 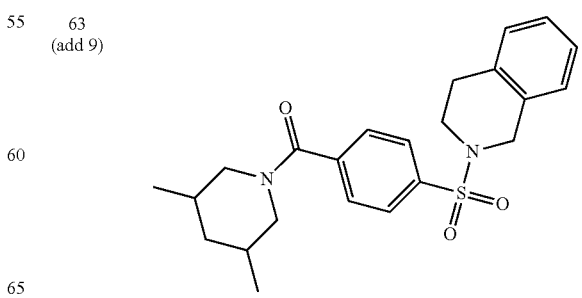 |

TABLE 33-continued
64 (add 10)
65 (add 11)
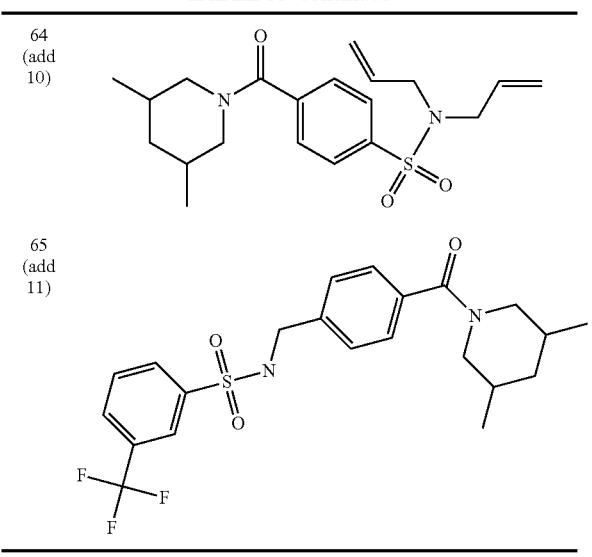
TABLE 34
66 (add 12)
67 (add 13)
68 (add 14)
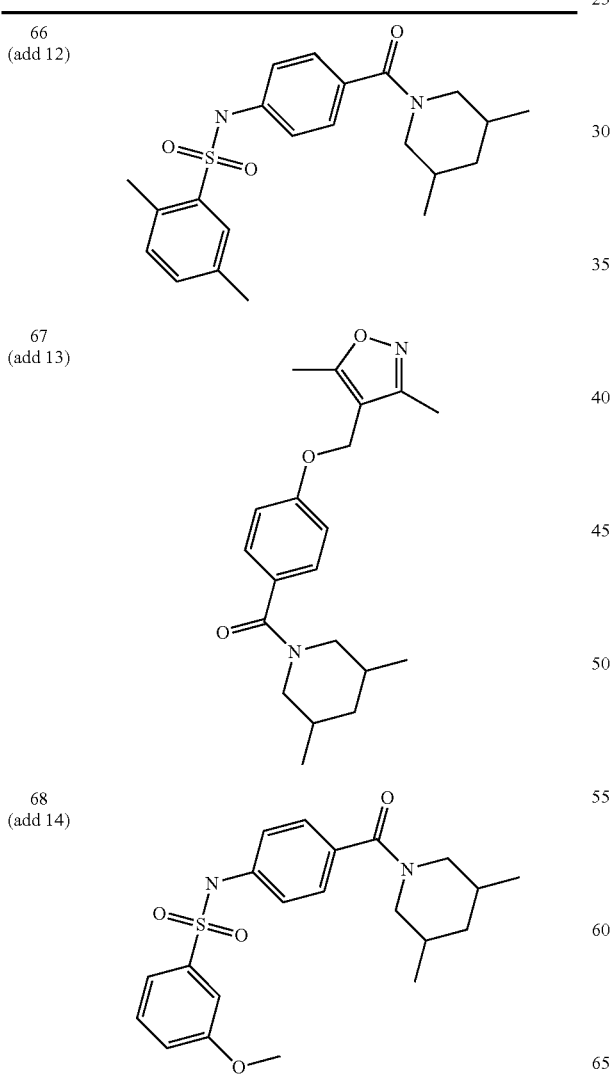
TABLE 34-continued
69 (add 15)
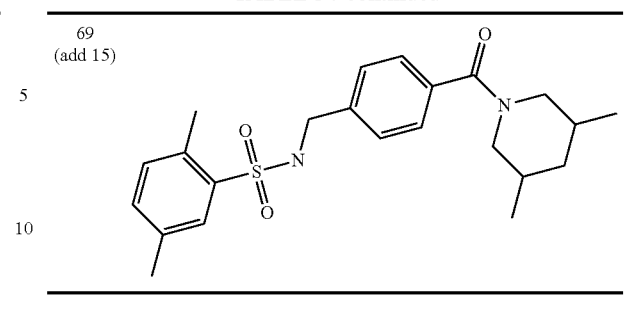
TABLE 35
70 (add 16)
71 (add 17)
72 (add 18)
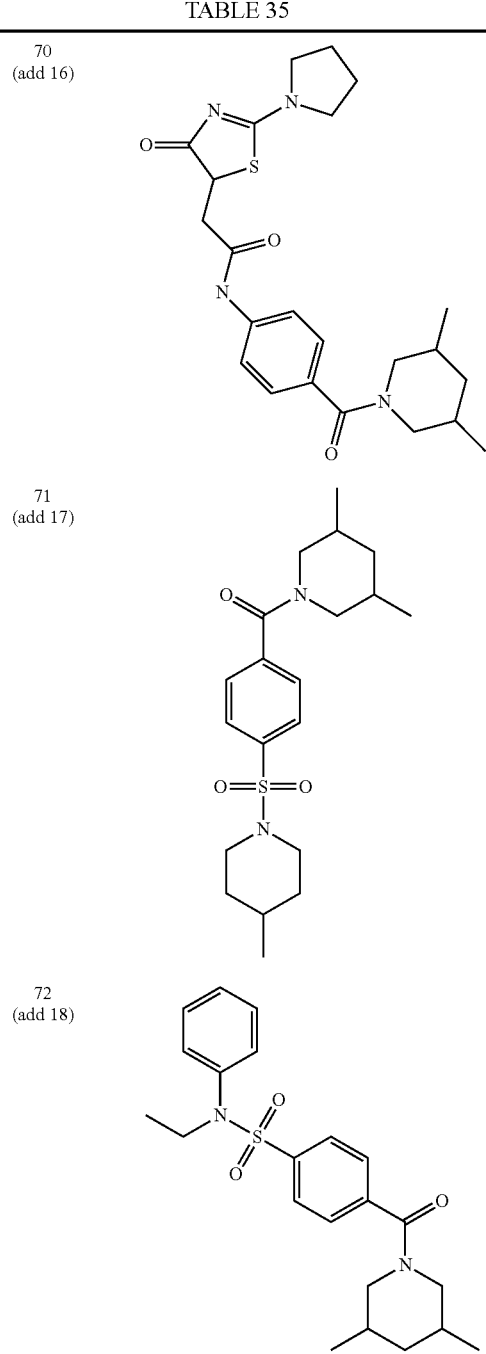

TABLE 35-continued
73
(add 19)
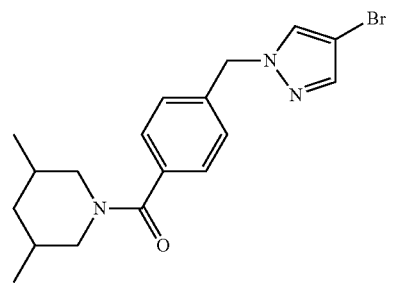 [SMILES: CC1CC(C)CN(C(=O)c2ccc(Cn3cc(Br)cn3)cc2)C1]
TABLE 36
74
(add 20)
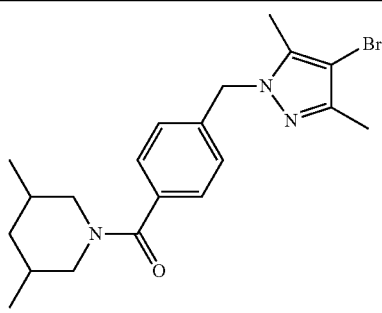
75
(add 21)
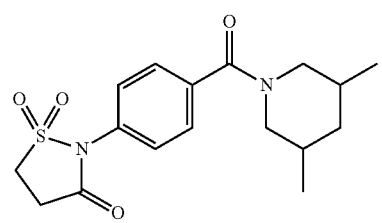 [SMILES: CC1CC(C)CN(C(=O)c2ccc(N3C(=O)CCS3(=O)=O)cc2)C1]
76
(add 22)
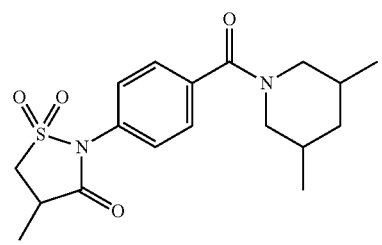 [SMILES: CC1CC(C)CN(C(=O)c2ccc(N3C(=O)C(C)CS3(=O)=O)cc2)C1]
77
(add 23)
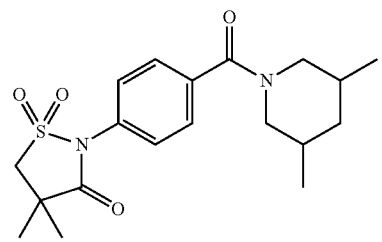 [SMILES: CC1CC(C)CN(C(=O)c2ccc(N3C(=O)C(C)(C)CS3(=O)=O)cc2)C1]
78
(add 24)
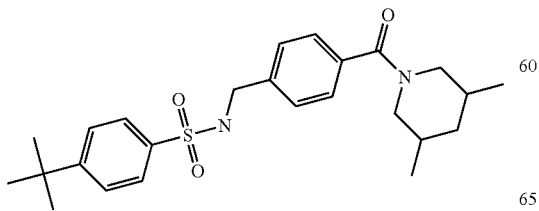
TABLE 37
79
(add 25)
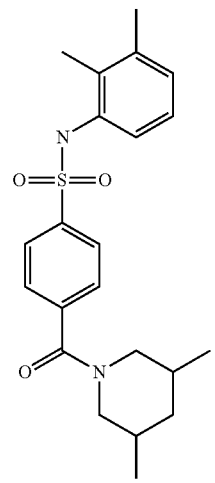 [SMILES: Cc1cccc(NS(=O)(=O)c2ccc(C(=O)N3CC(C)CC(C)C3)cc2)c1C]
80
(add 26)
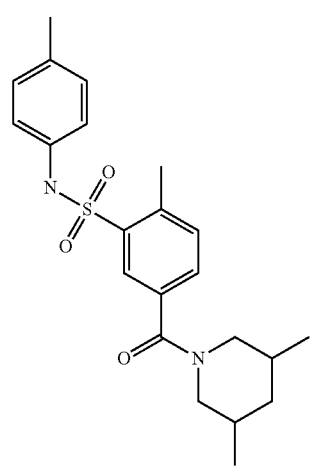 [SMILES: Cc1ccc(NS(=O)(=O)c2cc(C(=O)N3CC(C)CC(C)C3)ccc2C)cc1]
81
(add 27)
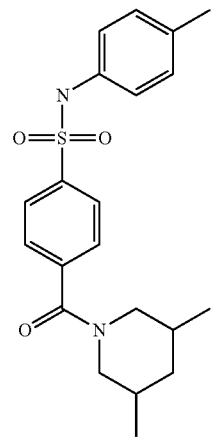 [SMILES: Cc1ccc(NS(=O)(=O)c2ccc(C(=O)N3CC(C)CC(C)C3)cc2)cc1]

TABLE 37-continued
82
(add 28)
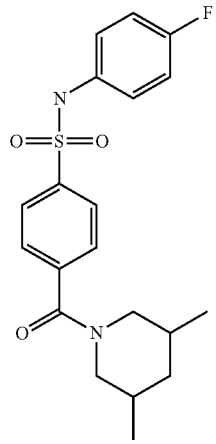 [SMILES: CC1CC(C)CN(C(=O)c2ccc(S(=O)(=O)Nc3ccc(F)cc3)cc2)C1]
83
(add 29)
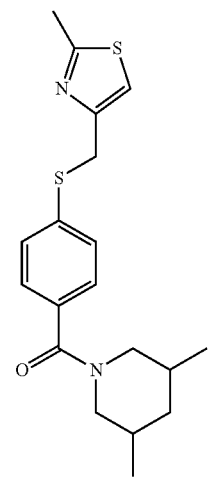 [SMILES: Cc1nc(CSc2ccc(C(=O)N3CC(C)CC(C)C3)cc2)cs1]
84
(add 30)
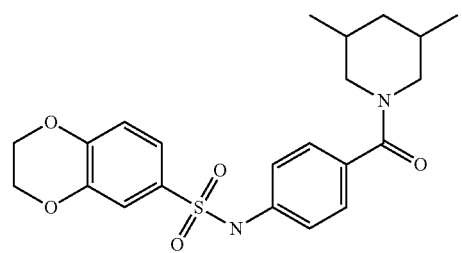 [SMILES: CC1CC(C)CN(C(=O)c2ccc(NS(=O)(=O)c3ccc4c(c3)OCCO4)cc2)C1]
TABLE 38
85
(add 31)
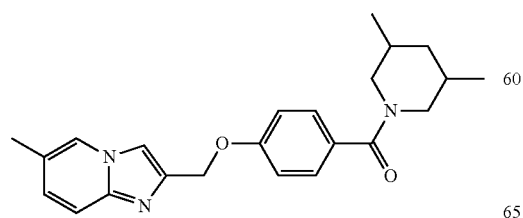
TABLE 38-continued
86
(add 32)
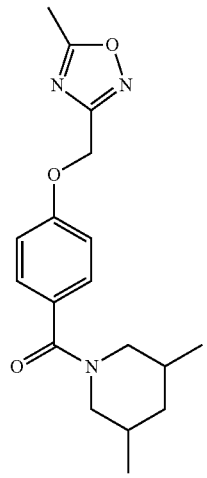 [SMILES: Cc1nc(COc2ccc(C(=O)N3CC(C)CC(C)C3)cc2)no1]
87
(add 33)
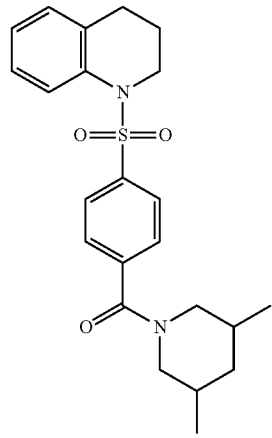 [SMILES: CC1CC(C)CN(C(=O)c2ccc(S(=O)(=O)N3CCCc4ccccc43)cc2)C1]
88
(add 34)
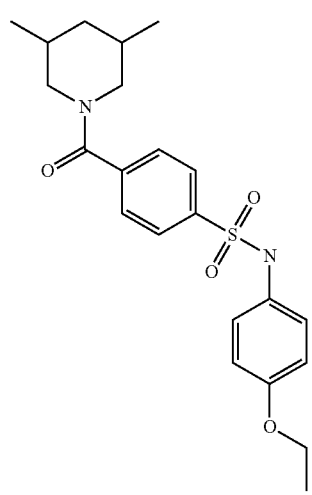 [SMILES: CCOc1ccc(NS(=O)(=O)c2ccc(C(=O)N3CC(C)CC(C)C3)cc2)cc1]

| 83 | 84 |
|---|---|
| TABLE 39 | TABLE 40 |
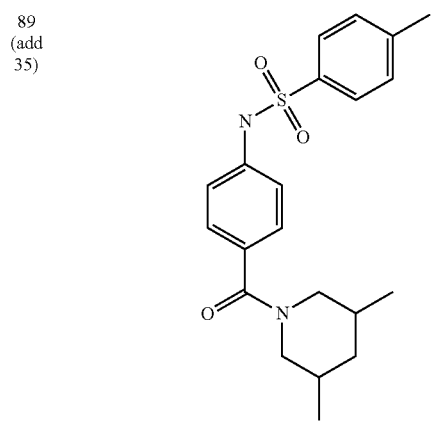
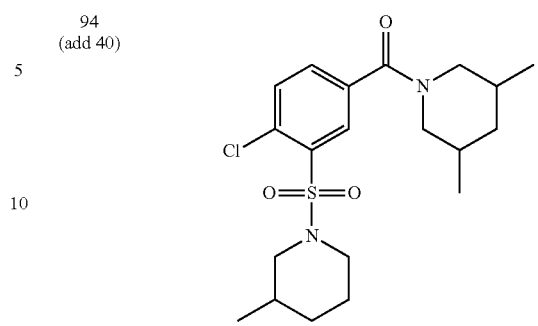
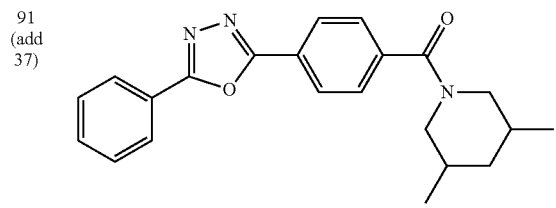

TABLE 41
98
(add 44)
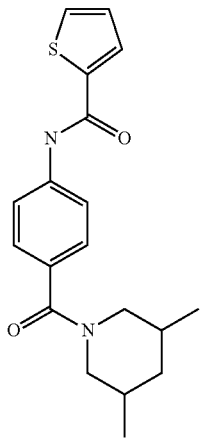 [SMILES: CC1CC(C)CN(C(=O)c2ccc(NC(=O)c3cccs3)cc2)C1]
99
(add 45)
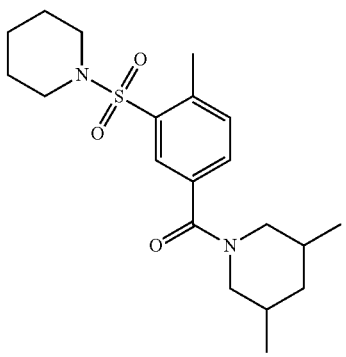 [SMILES: Cc1ccc(C(=O)N2CC(C)CC(C)C2)cc1S(=O)(=O)N1CCCCC1]
100
(add 46)
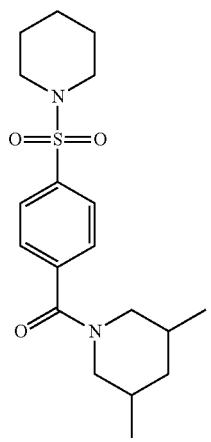 [SMILES: CC1CC(C)CN(C(=O)c2ccc(S(=O)(=O)N3CCCCC3)cc2)C1]
101
(add 47)
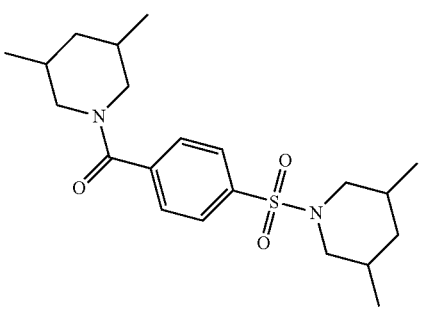
TABLE 42
102
(add 48)
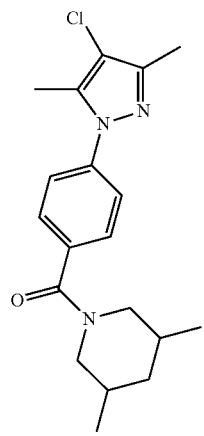 [SMILES: Cc1nn(-c2ccc(C(=O)N3CC(C)CC(C)C3)cc2)c(C)c1Cl]
103
(add 49)
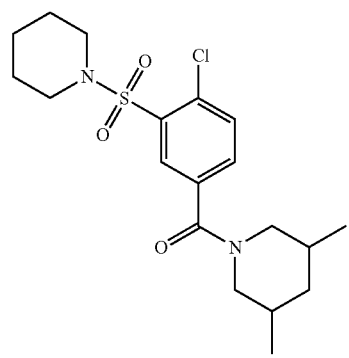 [SMILES: CC1CC(C)CN(C(=O)c2ccc(Cl)c(S(=O)(=O)N3CCCCC3)c2)C1]
104
(add 50)
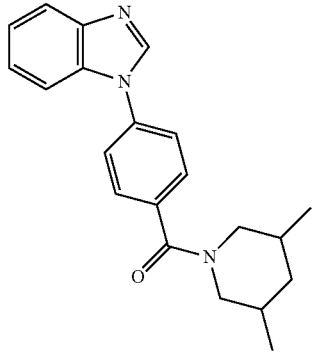 [SMILES: CC1CC(C)CN(C(=O)c2ccc(-n3cnc4ccccc43)cc2)C1]
105
(add 51)
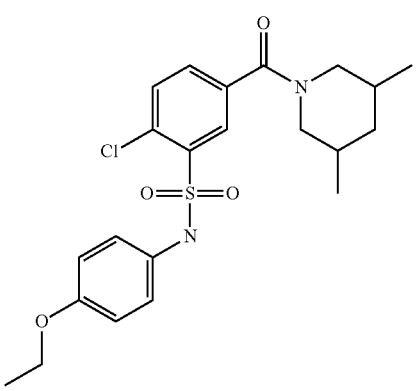 [SMILES: CCOc1ccc(NS(=O)(=O)c2cc(C(=O)N3CC(C)CC(C)C3)ccc2Cl)cc1]

TABLE 42-continued 106
(add 52)

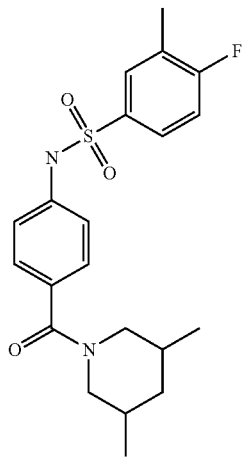 [SMILES: Cc1cc(S(=O)(=O)Nc2ccc(C(=O)N3CC(C)CC(C)C3)cc2)ccc1F]

Specific examples of the pharmacologically acceptable salt of the compound represented by formula (I) (including formula (Ia)) include, but are not limited to, alkaline metal salts such as sodium salt, potassium salt or lithium salt; alkaline earth metal salts such as calcium salt or magnesium salt; organic amine salts such as cyclohexylamine salt, trimethylamine salt or diethanolamine salt; basic amino acid salts such as arginine salt or lysine salt; and ammonium salts.

It is possible to convert the compound represented by formula (I) (including formula (Ia)) to a pharmacologically acceptable ester according to conventional methods. The types of the "pharmacologically acceptable ester" are not particularly limited. Any type of ester may be used as long as it has the same pharmaceutical applicability as the compound represented by formula (I) and is pharmacologically acceptable.

When the compound represented by formula (I) (including formula (Ia)) has asymmetric carbon(s) within its molecule, racemic compounds and optically active compounds thereof are also included in the present invention.

Compounds represented by formula (I) (including formula (Ia)), pharmacologically acceptable salts thereof or pharmacologically acceptable esters thereof may occur as various solvates, e.g., solvates formed with water, methanol, ethanol, dimethylformamide, ethyl acetate or the like. Pharmaceutical compositions comprising such solvates are also included in the present invention.

Compounds represented by formula (I) (including formula (Ia)), pharmacologically acceptable salts thereof or pharmacologically acceptable esters thereof bind to mSin3B that specifically binds to neural restrictive silencer factor (NRSF). Therefore, they may be used as a prophylactic and/or a therapeutic for diseases associated with abnormal expression of neural restrictive silencer factor NRSF/REST or abnormal expression of genes targeted by NRSF/REST. Examples of diseases associated with abnormal expression of neural restrictive silencer factor NRSF/REST or abnormal expression of genes targeted by NRSF/REST include neurodegenerative diseases (such as Down's syndrome, Alzheimer's disease, Huntington's disease and Parkinson's disease), cancer (such as medulloblastoma), atopic dermatitis, diabetes, cardiomyopathy, neuropathic pain and so forth.

It has been described above that abnormal expression of NRSF/REST or genes targeted by NRSF/REST is involved in Down's syndrome, Alzheimer's disease, Huntington's disease, medulloblastoma and neuropathic pain.

It has been reported that gene expression of an enzyme tyrosine hydroxylase which provides a rate limiting step in the synthetic pathway of dopamine (which is believed to be depleted in Parkinson's disease patients' brains) is regulated by NRSF/REST (Regulation of human tyrosine hydroxylase gene by neuron-restrictive silencer factor. Kim S M, Yang J W, Park M J, Lee J K, Kim S U, Lee Y S, Lee M A. BBRC 346, 426 (2006); Neuroscience Research, 65-236)).

A report has been made that NRSF/REST is a repressor of the expression of neuropilin-1 that is a receptor for semaphorin 3A (Sema3A) (Neuron restrictive silencer factor NRSF/REST is a transcriptional repressor of neuropilin-1 and diminishes the ability of semaphorin 3A to inhibit keratinocyte migration. Kurschat P, Bielenberg D, Rossignol-Tallandier M, Stahl A, Klagsbrun M. J Biol Chem. 2006 Feb. 3; 281(5):2721-9. Epub 2005 Dec. 5.). It has been reported that activation of Sema3A signals is effective in alleviating symptoms of atopic dermatitis; this suggests that NRSF/REST can be a novel target molecule for treating atopic dermatitis.

It has been reported that NRSF/REST is involved in the regulation of expression of connexin36 (essential for insulin secretion) (Critical role of the transcriptional repressor neuron-restrictive silencer factor in the specific control of connexin36 in insulin-producing cell lines. Martin D, Tawadros T, Meylan L, Abderrahmani A, Condorelli D F, Waeber G, Haefliger J A. J Biol Chem. 2003 Dec. 26; 278(52):53082-9. Epub 2003 Oct. 16.). This suggests that NRSF/REST can be a novel target molecule for treating diabetes.

It has been reported that mice expressing a dominant-negative mutant of NRSF/REST in their hearts exhibit dilated cardiomyopathy and highly likely to undergo arrhythmias or sudden death (NRSF regulates the fetal cardiac gene program and maintains normal cardiac structure and function. K. Kuwahara, Y. Saito, M. Takano, Y. Arai, S. Yasuno, Y. Nakagawa, N. Takahashi, Y. Adachi, G. Takemura, M. Horie, Y. Miyamaoto, T. Morisaki, S. kuratomi, A. Noma, H. Fujiwara, Y. Yoshimasa, H. Kinoshita, R. Kawakami, I. Kishimoto, M. Nakanishi, S. Usami, Y. Saito, M. Harada, K. Nakao, The EMBO Journal, 22, 6310-6321 (2003)). This suggests that NRSF/REST can be a novel target molecule for treating cardiomyopathy.

A substance capable of binding to the PAH1 domain of mSin3B (e.g., compounds represented by formula (I) (including formula (Ia)), pharmacologically acceptable salts thereof or pharmacologically acceptable esters thereof) may be administered to a human or an animal in the form of a pharmaceutical preparation (e.g., injection, capsules, tablets, powder, granules, etc.) formulated by conventional methods. For example, such a pharmaceutical preparation may be administered orally at a daily dose of approximately 0.1-1000 mg/kg (body weight), preferably at a daily dose of approximately 1-500 mg/kg (body weight), as converted to the amount of the active ingredient. This dose may be administered once or may be divided into several times. However, the dose and the number of times of administration may be appropriately altered depending on the symptoms and age of the patient, the method of administration route, and so forth. When the substance is formulated into an injection, a carrier such as physiological saline may be used. When the substance is formulated into capsules, tablets, powder or granules, excipients such as starch, lactose, sucrose or calcium carbonate; binders such as starch paste, gum arabic, gelatin, sodium alginate, carboxymethylcellulose or hydroxypropylcellulose; lubricants such as magnesium stearate or talc; and disintegrants such as starch, agar, crystalline cellulose, calcium carbonate, sodium hydrogencarbonate or sodium alginate may be used. The content of the active ingredient in pharmaceutical preparations may be varied between 1 to 99% by weight. For example, when the pharmaceutical preparation takes the form of tablets, capsules, granules or powder, the content of the active ingredient is preferably 5-80% by weight; when the pharmaceutical preparation takes the form of injection, the content of the active ingredient is preferably 1-10% by weight.

EXAMPLES

Hereinbelow, the present invention will be described with reference to the following Examples. However, the present invention is not limited to these Examples.

In Preparation Examples 1 to 22, the derivatives of 3,5-dimethyl-1-(3-methyl-4-nitrobenzoyl)piperidine shown below were synthesized.

NCR-1
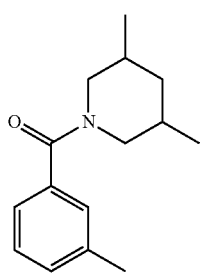

NCR-2
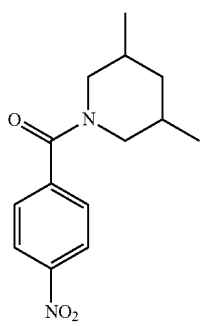

NCR-3
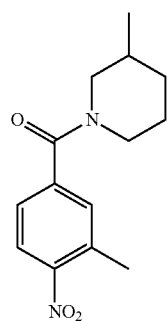

NCR-4
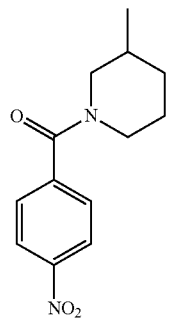

NCR-5
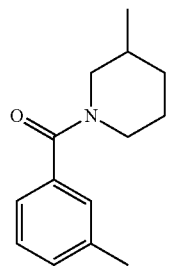

NCR-6
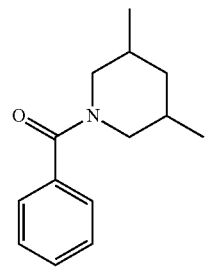

NCR-7
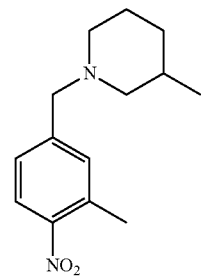

NCR-8
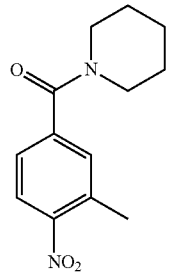

NCR-9
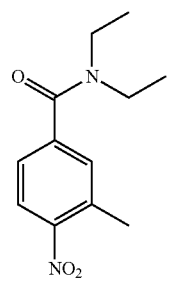
NCR-10
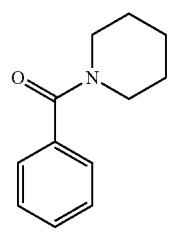
NCR-11
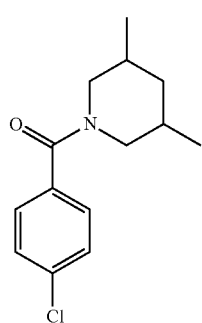
NCR-12
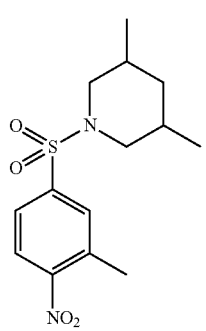
NCR-13
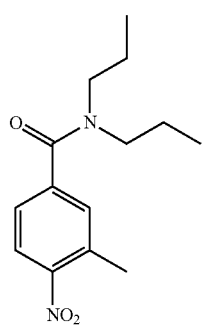
NCR-14
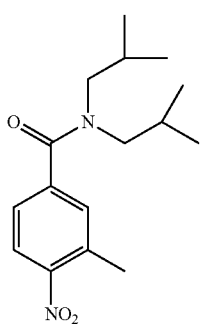
NCR-15
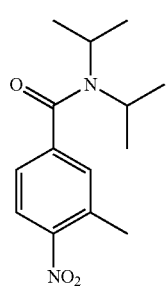
NCR-16
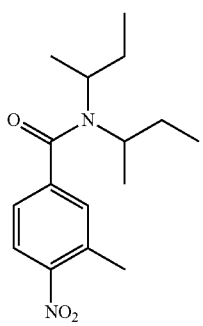
NCR-17
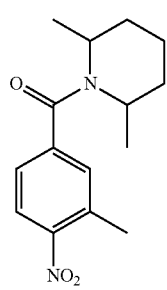
NCR-18
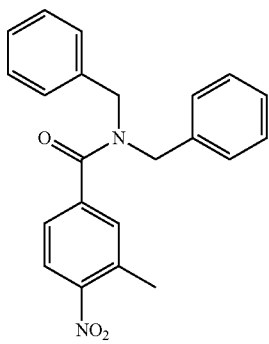

-continued
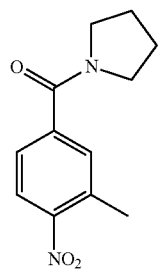
NCR-19
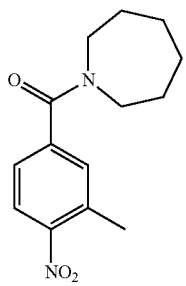
NCR-20
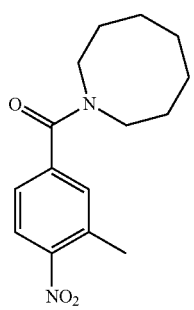
NCR-21
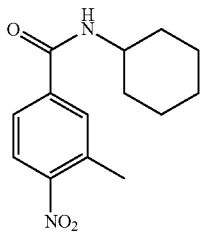
NCR-22
Methods of synthesis are summarized in Schemes 1 to 4 described below.
Scheme 1
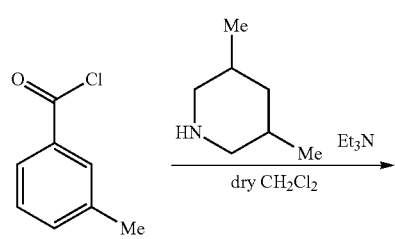
-continued
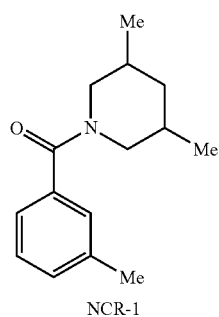
NCR-1
Scheme 2
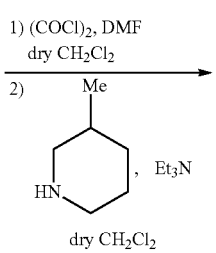
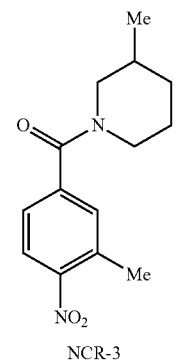
NCR-3
Scheme 3
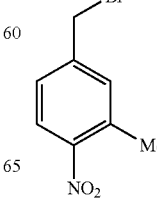
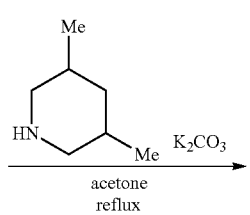

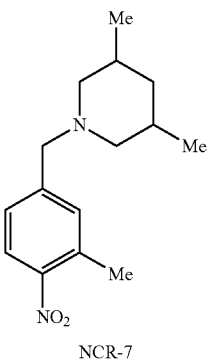

NCR-7

Scheme 4

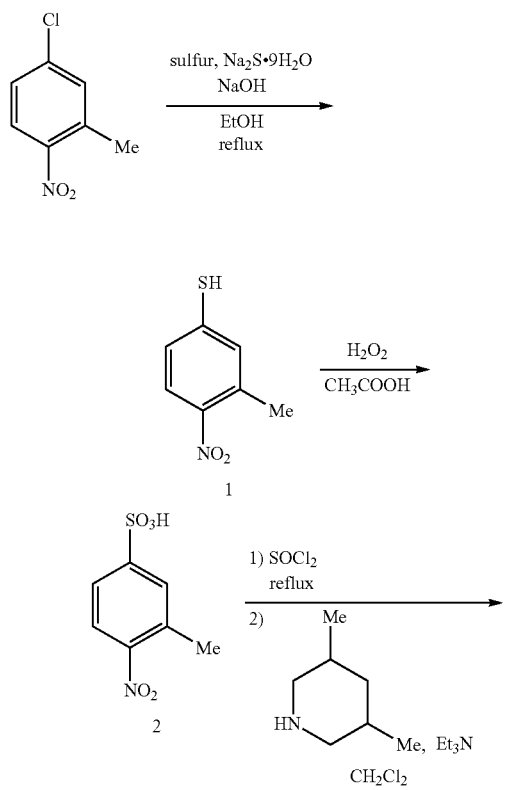

NCR-12

Preparation Example 1

Scheme 1

Preparation of
3,5-Dimethyl-1-(3-Methylbenzoyl)piperidine
(NCR-1)

3,5-Dimethylpiperidine (0.73 g) and triethylamine (2.25 ml) were dissolved in dichloromethane (20 ml). A solution of 3-methylbenzoylchloride (1.00 g) in dichloromethane (10 ml) was added dropwise at the freezing point. After stirring for 30 minutes at 0° C., the reaction solution was poured into water (100 ml) and extracted with chloroform (50 ml). The organic layer was washed with saturated brine (100 ml), dried over anhydrous sodium sulfate and, after filtration, concentrated under reduced pressure. The residue was purified by silica gel flash column chromatography (developing solvent: n-hexane/ethyl acetate=4:1) to obtain the subject compound (NCR-1 cis form:trans form=9:1) (0.95 g, yield 63%) as a colorless oil. $^1$H-NMR (CDCl$_3$, 500 MHz, δ; ppm) 0.76-1.86 (10H, m), 2.15-2.23 (0.9H, m), 2.36 (3H, s), 2.44-2.49 (0.9H, m), 3.08 (0.1H, m), 3.20 (0.1H, m), 3.32-3.34 (0.1H, m), 3.63-3.65 (0.9H, m), 7.14 (1H, d, J=7.3 Hz), 7.19 (1H, d, J=7.3 Hz), 7.20 (1H, s), 7.26 (1H, t, J=7.6 Hz); MS (EI) m/z: 231 (M$^+$).

Preparation Example 2

Scheme 1

Preparation of
3,5-Dimethyl-1-(4-Nitrobenzoyl)piperidine (NCR-2)

The subject compound (NCR-2 cis form:trans form=9:1) (yield 92%) was obtained in the same manner as in Preparation Example 1 except that 4-nitrobenzoylchloride was used instead of 3-methylbenzoylchloride. Crude crystals of NCR-2 (1.31 g) were re-crystallized from n-hexane-chloroform to obtain white crystals (0.78 g).

mp 120-125° C.; $^1$H-NMR (CDCl$_3$, 500 MHz, δ; ppm) 0.77-1.71 (10H, m), 2.20-2.51 (0.9H, m), 2.51-2.56 (0.9H, m), 2.99 (0.1H, m), 3.22 (0.1H, m), 3.27-3.29 (0.1H, m), 3.42-3.45 (0.9H, m), 3.89-3.91 (0.1H, m), 4.66-4.68 (0.9H, m), 7.54 (2H, d, J=8.7 Hz), 8.27 (2H, d, J=8.7 Hz); MS (EI) m/z: 262 (M$^+$); Anal. Calcd. for C$_{14}$H$_{18}$N$_2$O$_3$: C, 64.10; H, 6.92; N, 10.68. Found: C, 65.51; H, 7.17; N, 10.97.

Preparation Example 3

Scheme 1

Preparation of
3-Methyl-1-(4-Nitrobenzoyl)piperidine (NCR-4)

The subject compound (NCR-4) (yield 89%) was obtained in the same manner as in Preparation Example 1 except that 3-methylpiperidine was used instead of 3,5-dimethylpiperidine and that 4-nitrobenzoylchloride was used instead of 3-methylbenzoylchloride. Crude crystals of NCR-4 (1.19 g) were re-crystallized from n-hexane-chloroform to obtain brown crystals (0.83 g).

mp 70.2-71.3° C.; $^1$H-NMR (CDCl$_3$, 500 MHz, δ; ppm) 0.79 (1.5H, d, J=6.5 Hz), 0.97 (1.5H, d, J=6.5 Hz), 1.17-1.89 (5H, m), 2.47 (0.5H, m), 2.67 (0.5H, m), 2.84 (0.5H, m), 2.96 (0.5H, m), 3.42 (0.5H, m), 3.49 (0.5H, m), 4.51 (1H, m), 7.54 (2H, d, J=8.8 Hz), 8.25 (2H, d, J=8.5 Hz); MS (EI) m/z: 248

(M+); Anal. Calcd. for $C_{13}H_{16}N_2O_3$: C, 62.89; H, 6.50; N, 11.28. Found: C, 62.78; H, 6.42; N, 11.28.

Preparation Example 4

Scheme 1

Preparation of 3-Methyl-1-(3-Methylbenzoyl)piperidine (NCR-5)

The subject compound (NCR-4) (yield 75%) was obtained as a colorless, oily material, in the same manner as in Preparation Example 1 except that 3-methylpiperidine was used instead of 3,5-dimethylpiperidine.

$^1$H-NMR (CDCl$_3$, 500 MHz, δ; ppm) 0.77 (1.5H, s), 0.94 (1.5H, s), 1.11-1.85 (51H, m), 2.34 (3H, m), 2.41 (0.5H, m), 2.61 (0.5H, m), 2.78 (0.5H, m), 2.90 (0.5H, m), 3.57-3.65 (1H, m), 4.51 (1H, m), 7.13 (1H, d, J=7.4 Hz), 7.17-7.18 (2H, m), 7.24 (1H, t, J=7.8 Hz); MS (EI) m/z: 217 (M+).

Preparation Example 5

Scheme 1

Preparation of 1-(Benzoyl)-3,5-Dimethyl piperidine (NCR-6)

The subject compound (NCR-6 cis form:trans form=9:1) (yield 76%) was obtained in the same manner as in Preparation Example 1 except that benzoylchloride was used instead of 3-methylbenzoylchloride. Crude crystals of NCR-6 (1.18 g) were re-crystallized from n-hexane-chloroform to obtain white crystals (0.48 g).

mp 107.2-108.7° C.; $^1$H-NMR (CDCl3, 500 MHz, δ; ppm) 0.76-0.96 (6H, m), 1.47-1.87 (4H, m), 2.17-2.22 (0.9H, m), 2.45-2.50 (0.9H, m), 3.07 (0.1H, m), 3.21 (0.1H, m), 3.32-3.34 (0.1H, m), 3.61-3.63 (0.9H, m), 3.88 (0.1H, m), 4.68-4.70 (0.9H, m), 7.36-7.41 (5H, m); MS (EI) m/z: 217 (M+); Anal. Calcd. for $C_{14}H_{19}NO$: C, 77.38; H, 8.81; N, 6.45. Found: C, 77.03; H, 8.72; N, 6.59.

Preparation Example 6

Scheme 1

Preparation of 1-Benzoylpiperidine (NCR-10)

The subject compound (NCR-10) (yield 76%) was obtained as a colorless oil in the same manner as in Preparation Example 1 except that piperidine was used instead of 3,5-dimethylpiperidine and that benzoylchloride was used instead of 3-methylbenzoylchloride.

$^1$H-NMR (CDCl3, 500 MHz, δ; ppm) 1.41 (2H, s), 1.57 (4H, s), 3.24 (2H, s), 3.62 (2H, s), 7.29 (5H, s); MS (EI) m/z: 189 (M+), Preparation Example 7

Scheme 1

Preparation of 3,5-Dimethyl-1-(4-Chlorobenzoyl)piperidine (NCR-11)

The subject compound (NCR-11 cis form:trans form=9:1) (yield 77%) was obtained in the same manner as in Preparation Example 1 except that 4-chlorobenzoylchloride was used instead of 3-methylbenzoylchloride. Crude crystals of NCR-11 (1.11 g) were re-crystallized from n-hexane-chloroform to obtain white crystals (0.53 g).

mp 113.5-115.4° C.; $^1$H-NMR (CDCl3, 500 MHz, δ; ppm) 0.74-0.93 (7H, m), 1.45-1.96 (3H, m), 2.14-2.19 (0.9H, m), 2.45-2.50 (0.9H, m), 3.03 (0.1H, m), 3.17 (0.1H, m), 3.28 (0.1H, m), 3.54-3.56 (0.9H, m), 3.83 (0.1H, m), 4.62-4.64 (0.9H, m), 7.28-7.32 (2H, m), 7.33-7.36 (2H, m); MS (EI) m/z: 251 (M+); Anal. Calcd. for $C_{14}H_{18}NO$: C, 66.79; H, 7.21; N, 5.56. Found: C, 66.42; H, 6.96; N, 5.80.

Preparation Example 8

Scheme 2

Preparation of 3-Methyl-1-(3-Methyl-4-Nitrobenzoyl)piperidine (NCR-3)

3-Methyl-4-nitrobenzoic acid (1.00 g) and N,N-dimethylformamide (catalytic amount) were dissolved in dichloromethane (20 ml). Oxalyl chloride (0.94 ml) was added, and the resultant mixture was stirred at 0° C. for 1 hour and 30 minutes. The reaction solution was concentrated under reduced pressure, dissolved in dichloromethane (10 ml) and added dropwise to a solution of 3-methylpiperidine (1.10 g) and triethylamine (1.90 ml) in dichloromethane (20 ml) at the freezing point. After stirring for 20 hours at 0° C., the reaction solution was poured to water (100 ml) and extracted with chloroform (50 ml). The organic layer was washed with saturated brine (100 ml), dried over anhydrous sodium sulfate and, after filtration, concentrated under reduced pressure. The residue was purified by silica gel flash column chromatography (developing solvent: n-hexane/ethyl acetate=2:1) to obtain the subject compound (NCR-3) (1.37 g, yield 94%). Crude crystals of NCR-3 (1.37 g) were re-crystallized from n-hexane-chloroform to obtain white crystals (0.88 g).

mp 82.0-82.8° C.; $^1$H-NMR (CDCl3, 500 MHz, δ; ppm) 0.72 (1.5H, d, J=6.5 Hz), 0.89 (1.5H, d, J=6.5 Hz), 1.08-1.80 (5H, m), 2.34-2.39 (0.5H, m), 2.53 (3H, s), 2.55-2.60 (0.5H, m), 2.72-2.76 (0.5H, m), 2.84-2.89 (0.5H, m), 3.35-3.38 (0.5H, m), 3.42-3.45 (0.5H, m), 4.42-4.44 (1H, m), 7.22 (1H, d, J=8.3 Hz), 7.26 (1H, s), 7.90 (1H, d, J=8.3 Hz); MS (EI) m/z: 262 (M+); Anal. Calcd. for $C_{14}H_{18}N_2O_3$: C, 64.10; H, 6.92; N, 10.68. Found: C, 65.23; H, 7.13; N, 10.96.

Preparation Example 9

Scheme 2

Preparation of 1-(3-Methyl-4-Nitrobenzoyl)piperidine (NCR-8)

The subject compound (NCR-8) (yield 89%) was obtained in the same manner as in Preparation Example 8 except that piperidine was used instead of 3-methylpiperidine. Crude crystals of NCR-8 (1.22 g) were re-crystallized from n-hexane-chloroform to obtain white crystals (0.98 g).

mp 71.7-72.2° C.; $^1$H-NMR (CDCl$_3$, 500 MHz; ppm) 1.52 (2H, s), 1.69 (4H, s), 2.61 (3H, s), 3.29 (2H, s), 3.71 (2H, s), 7.33 (1H, d, J=8.3 Hz), 7.36 (1H, s), 7.99 (1H, d, J=8.4 Hz); MS (EI) m/z: 248 (M+); Anal. Calcd. for $C_{13}H_{16}N_2O_3$: C, 62.89; H, 6.50; N, 11.28. Found: C, 62.29; H, 6.40; N, 11.17.

Preparation Example 10

Scheme 2

Preparation of N,N-Diethyl-3 Methyl-4-Nitrobenzamide (NCR-9)

The subject compound (NCR-9) (yield 71%) was obtained in the same manner as in Preparation Example 8 except that diethylamine was used instead of 3-methylpiperidine. Crude crystals of NCR-9 (0.93 g) were re-crystallized with n-hexane-chloroform to obtain brown crystals (0.63 g).

mp 74.5-76.0° C.; $^1$H-NMR (CDCl3, 500 MHz, δ; ppm) 1.13 (3H, m), 1.26 (3H, m), 2.63 (3H, s), 3.24 (2H, m), 3.36 (2H, m), 7.34-7.37 (2H, m), 8.01 (1H, d, J=8.0 Hz); MS (EI) m/z: 236 (M$^+$); Anal. Calcd. for $C_{12}H_{16}N_2O_3$: C, 61.00; H, 6.83; N, 11.86. Found: C, 60.72; H, 6.94; N, 11.83.

Preparation Example 11

Scheme 2

Preparation of 3-Methyl-4-Nitro-N,N-Dipropylbenzamide (NCR-13)

The subject compound (NCR-13) (yield 90%) was obtained as a yellow oil in the same manner as in Preparation Example 8 except that dipropylamine was used instead of 3-methylpiperidine.

$^1$H-NMR (CDCl3, 500 MHz, δ; ppm) 0.58-0.61 (3H, m), 0.79-0.82 (3H, m), 1.35-1.39 (2H, m), 1.42-1.57 (2H, s), 2.45 (3H, s), 2.97-3.00 (2H, m), 3.29-3.32 (2H, m), 7.17 (1H, d, J=8.4 Hz), 7.19 (1H, s), 7.83 (1H, d, J=8.3 Hz); MS (EI) m/z: 264 (MI).

Preparation Example 12

Scheme 2

Preparation of N,N-Diisobutyl-3-Methyl-4-Nitrobenzamide (NCR-14)

The subject compound (NCR-14) (yield 99%) was obtained as a yellow oil in the same manner as in Preparation Example 8 except that diisobutylamine was used instead of 3-methylpiperidine.

$^1$H-NMR (CDCl3, 500 MHz, δ; ppm) 0.65 (6H, d, J=6.5 Hz), 0.88 (6H, d, J=7.0 Hz), 1.75-1.81 (1H, m), 2.01-2.05 (1H, m), 2.51 (3H, s), 2.96 (2H, d, J=7.5 Hz), 3.27 (2H, d, J=7.5 Hz), 7.20-7.22 (2H, m), 7.89 (1H, d, J=9.0 Hz); MS (EI) m/z: 292 (M$^+$).

Preparation Example 13

Scheme 2

Preparation of N,N-Diisopropyl-3-Methyl-4-Nitrobenzamide (NCR-15)

The subject compound (NCR-15) (yield 71%) was obtained as a yellow oil in the same manner as in Preparation Example 8 except that diisopropylamine was used instead of 3-methylpiperidine. Crude crystals of NCR-15 (0.94 g) were re-crystallized from n-hexane-chloroform to obtain white crystals (0.60 g).

mp 107.6-109.7° C.; $^1$H-NMR (CDCl3, 500 MHz, δ; ppm) 1.16 (6H, m), 1.54 (6H, m), 3.54 (1H, m), 3.71 (1H, m), 7.26 (1H, d, J=8.3 Hz), 7.28 (1H, s), 8.00 (1H, d, J=8.3 Hz); MS (EI) m/z: 264 (M$^+$); Anal. Calcd. for $C_{14}H_{20}N_2O_3$: C, 63.62; H, 7.63; N, 10.60. Found: C, 63.47; H, 7.47; N, 10.66.

Preparation Example 14

Scheme 2

Preparation of N,N-di-sec-Butyl-3-Methyl-4-Nitrobenzamide (NCR-16)

The subject compound (NCR-16) (yield 83%) was obtained as a yellow oil in the same manner as in Preparation Example 8 except that di-sec-butylamine was used instead of 3-methylpiperidine.

$^1$H-NMR (CDCl3, 500 MHz, δ; ppm) 0.83-0.86 (3H, m), 0.95-0.98 (3H, m), 1.16-1.17 (3H, m), 1.43 (1H, m), 1.50-1.53 (3H, m), 1.58-1.60 (1H, m), 1.85-2.28 (2H, m), 2.62 (3H, s), 3.15 (1H, m), 3.46 (1H, m), 7.26-7.28 (2H, m), 7.99 (1H, d, J=8.2 Hz); MS (EI) m/z: 292 (M$^+$).

Preparation Example 15

Scheme 2

Preparation of 2,6-Dimethyl-1-(3-Methyl-4-Nitrobenzoyl)piperidine (NCR-17)

The subject compound (NCR-17) (yield 82%) was obtained in the same manner as in Preparation Example 8 except that cis-2,6-dimethylpiperidine was used instead of 3-methylpiperidine. Crude crystals of NCR-17 (1.14 g) were re-crystallized from n-hexane-chloroform to obtain white crystals (0.79 g).

mp 99.7-100.5° C.; $^1$H-NMR (CDCl3, 500 MHz, δ; ppm) 1.29 (6H, m), 1.55-1.74 (6H, m), 1.84-1.89 (2H, m), 7.30 (1H, d, J=8.3 Hz), 7.31 (1H, s), 8.01 (1H, d, J=8.3 Hz); MS (EI) m/z: 276 (M$^+$); Anal. Calcd. for $C_{15}H_{20}N_2O_3$: C, 65.20; H, 7.30; N, 10.14. Found: C, 64.97; H, 7.01; N, 10.07.

Preparation Example 16

Scheme 2

Preparation of N,N-Dibenzyl-3-Methyl-4-Nitrobenzamide (NCR-18)

The subject compound (NCR-18) (yield 75%) was obtained as white crystals in the same manner as in Preparation Example 8 except that dibenzylamine was used instead of 3-methylpiperidine and that re-crystallization with n-hexane-chloroform was carried out instead of silica gel flash column chromatography.

mp 105.8-108.7° C.; $^1$H-NMR (CDCl3, 500 MHz, δ; ppm) 2.58 (3H, s), 4.35 (2H, s), 4.72 (2H, s), 7.12 (2H, d, J=7.0 Hz), 7.29-7.43 (10H, m), 7.96 (1H, d, J=8.5 Hz); MS (EI) m/z: 360 (M$^+$); Anal. Calcd. for $C_{22}H_{20}N_2O_3$: C, 73.32; H, 5.59; N, 7.77. Found: C, 73.10; H, 5.95; N, 8.08.

Preparation Example 17

Scheme 2

Preparation of 1-(3-Methyl-4-Nitrobenzoyl)pyrrolidine (NCR-19)

The subject compound (NCR-19) (yield 96%) was obtained in the same manner as in Preparation Example 8 except that pyrrolidine was used instead of 3-methylpiperidine. Crude crystals of NCR-19 (1.13 g) were re-crystallized from n-hexane-chloroform to obtain yellow crystals (0.71 g).

mp 61.3-61.9° C.; $^1$H-NMR (CDCl3, 500 MHz, δ; ppm) 1.87-1.91 (2H, m), 1.93-1.97 (2H, m), 2.58 (3H, s), 3.35 (2H, t, J=6.7 Hz), 3.61 (2H, t, J=7.0 Hz), 7.42 (1H, d, J=8.3 Hz), 7.46 (1H, s), 7.96 (1H, d, J=8.4 Hz); MS (EI) m/z: 234 (M$^+$); Anal. Calcd. for $C_{12}H_{14}N_2O_3$: C, 61.53; H, 6.02; N, 11.96. Found: C, 61.41; H, 5.98; N, 11.92.

Preparation Example 18

Scheme 2

Preparation of 1-(3-Methyl-4-Nitrobenzyol)azepane (NCR-20)

The subject compound (NCR-20) (yield 92%) was obtained in the same manner as in Preparation Example 8 except that azepane was used instead of 3-methylpiperidine. Crude crystals of NCR-20 (1.21 g) were re-crystallized from n-hexane-chloroform to obtain yellow crystals (0.69 g).

mp 62.5-63.8° C.; $^1$H-NMR (CDCl3, 500 MHz, δ; ppm) 1.62-1.65 (6H, m), 1.82-1.85 (2H, m), 2.62 (3H, s), 3.36 (2H, t, J=5.5 Hz), 3.68 (2H, t, J=5.5 Hz), 7.36 (1H, d, J=8.2 Hz), 7.38 (1H, s), 8.00 (1H, d, J=8.3 Hz); MS (EI) m/z: 262 (M$^+$); Anal. Calcd. for $C_{14}H_{18}N_2O_3$: C, 64.10; H, 6.92; N, 10.68. Found: C, 63.84; H, 6.76; N, 10.70.

Preparation Example 19

Scheme 2

Preparation of 1-(3-Methyl-4-Nitrobenzyol)azocane (NCR-21)

The subject compound (NCR-21) (yield 64%) was obtained in the same manner as in Preparation Example 8 except that azocane was used instead of 3-methylpiperidine. Crude crystals of NCR-21 (0.89 g) were re-crystallized from n-hexane-chloroform to obtain yellow crystals (0.80 g).

mp 75.7-77.0° C.; $^1$H-NMR (CDCl3, 500 MHz, δ; ppm) 1.59 (8H, m), 1.85-1.86 (2H, m), 2.60 (3H, s), 3.26 (2H, m), 3.61 (2H, t, J=6.5 Hz), 7.30 (1H, d, J=8.5 Hz), 7.31 (1H, s), 7.98 (1H, d, J=8.3 Hz); MS (EI) m/z: 276 (M$^+$); Anal. Calcd. for $C_{15}H_{20}N_2O_3$: C, 65.20; H, 7.30; N, 10.14. Found: C, 65.09; H, 7.29; N, 10.10.

Preparation Example 20

Scheme 2

Preparation of N-Cyclohexyl-3-Methyl-4-Nitrobenzamide (NCR-22)

The subject compound (NCR-22) (yield 53%) was obtained in the same manner as in Preparation Example 8 except that cyclohexylamine was used instead of 3-methylpiperidine. Crude crystals of NCR-22 (0.70 g) were re-crystallized with n-hexane-chloroform to obtain white crystals (0.55 g).

mp 134.2-141.0° C.; $^1$H-NMR (CDCl3, 500 MHz, δ; ppm) 1.20-1.29 (3H, m), 1.40-1.48 (21H, m), 1.66-1.80 (3H, m), 2.04-2.05 (2H, m), 2.64 (3H, s), 3.96-3.99 (1H, m), 5.95 (1H, brs), 7.66 (1H, d, J=8.5 Hz), 7.73 (1H, s), 7.99 (1H, d, J=8.6 Hz); MS (EI) m/z: 262 (M$^+$); Anal. Calcd. for $C_{14}H_{18}N_2O_3$: C, 64.10; H, 6.92; N, 10.68. Found: C, 63.89; H, 6.72; N, 10.68.

Preparation Example 21

Scheme 3

Preparation of 3,5-Dimethyl-1-(3-Methyl-4-Nitrobenzyl)piperidine (NCR-7)

3-Methyl-4-nitrobenzyl bromide (1.00 g), 3,5-dimethylpiperidine (0.60 ml) and potassium carbonate (0.90 g) were dissolved in acetone (20 ml), followed by heating under reflux for 6 hours. The reaction solution was concentrated under reduced pressure, dissolved in chloroform (10 ml), poured into water (100 ml) and extracted with chloroform (50 ml). The organic layer was washed with saturated brine (100 ml), dried over anhydrous sodium sulfate and, after filtration, concentrated under reduced pressure. The residue was purified by silica gel flash column chromatography (developing solvent: n-hexane/ethyl acetate=10:1) to obtain the subject compound (NCR-7) (0.70 g, yield 61%) as a yellow oil.

$^1$H-NMR (CDCl$_3$, 500 MHz, δ; ppm) 0.80-0.82 (6H, m), 1.44-1.48 (2H, m), 1.64-1.72 (3H, m), 2.59 (3H, s), 2.71-2.74 (2H, m), 3.46 (2H, s), 7.27-7.29 (2H, m), 7.92 (1H, d, J=9.0 Hz); MS (EI) m/z: 262 (M$^+$);

Preparation Example 22

Scheme 4

Preparation of 3,5-Dimethyl-1-[(3-Methyl-4-Nitrophenyl)sulfonyl]piperidine (NCR-12)

Step 1: Preparation of 3-Methyl 4-Nitrobenzenethiol (1)

5-Chloro-2-nitrotoluene (1.00 g), sodium sulfate nonahydrate (1.01 g), sulfur (136.24 mg) and sodium hydroxide (233.12 mg) were dissolved in ethanol (20 ml) and heated under reflux for 2 hours. The reaction solution was poured into 10% hydrochloric acid (100 ml) and extracted with ethyl acetate (50 ml). The organic layer was washed with saturated brine (100 ml), dried over anhydrous sodium sulfate and, after filtration, concentrated under reduced pressure.

The residue was purified by silica gel flash column chromatography (developing solvent: n-hexane/ethyl acetate=15:1) to obtain the subject compound (1) (0.74 g, yield 75%) as brown crystals.

$^1$H-NMR (DMSO, 500 MHz, δ; ppm) 2.01 (1H, s), 2.48 (3H, s), 7.50-7.63 (2H, m), 7.99 (1H, s).

Step 2: Preparation of 3-Methyl-4-Nitrobenzenesulfonic Acid (2)

The 3-methyl 4-nitrobenzenethiol (1) (0.74 g) obtained in the preceding step was dissolved in acetic acid (10 ml). Aqueous hydrogen peroxide (5 ml) was added thereto, and the resultant mixture was stirred at room temperature for 1 hour and 30 minutes. The reaction solution was concentrated under reduced pressure, purified by silica gel flash column chromatography (developing solvent: n-hexane/ethyl acetate=20:1) to obtain the subject compound (2) (0.64 g, yield 68%) as a yellow oil.

$^1$H-NMR (DMSO, 500 MHz, δ; ppm) 2.56 (3H, s), 7.78 (1H, d, =8.1 Hz), 7.83 (1H, s), 7.96 (1H, d, J=8.4 Hz).

Step 3: Preparation of 3,5-Dimethyl-1-[(3-Methyl-4-Nitrophenyl)sulfonyl]piperidine The 3-methyl-4-nitrobenzenesulfonic acid (2) (0.64 g) obtained in Step 2 was dissolved in thionyl chloride (1.2 ml) and heated under reflux for 20 hours. The reaction solution was concentrated under reduced pressure and dissolved in dichloromethane (5 ml). This solution was added dropwise to a solution of 3,5-dimethylpiperidine (0.49 ml) and triethylamine (1.20 ml) in dichloromethane (10 ml) at the freezing point. After stirring for 3 hours and 30 minutes at room temperature, the reaction solution was poured into water (50 ml) and extracted with chloroform (20 ml). The organic layer was washed with saturated brine (50 ml), dried over anhydrous sodium sulfate and, after filtration, concentrated under reduced pressure. The residue was purified by silica gel flash column chromatography (developing solvent: n-hexane/ethyl acetate=10:1) to obtain the subject compound (NCR-12) (155.3 mg, yield 17%). Crude crystals of NCR-12 (155.3 mg) were re-crystallized from n-hexane-chloroform to obtain brown crystals (99.2 mg).

mp 132.7-138.5° C.; $^1$H-NMR (CDCl3, 500 MHz, δ; ppm) 0.88-0.89 (6H, m), 1.58-1.81 (6H, m), 3.76 (2H, d, J=6.5 Hz), 7.73 (1H, d, J=8.0 Hz), 7.75 (1H, s), 8.06 (1H, d, J=8.3 Hz); MS (EI) m/z: 312 (M$^+$); Anal. Calcd. for $C_{14}H_{20}N_2O_4S$: C, 53.83; H, 6.45; N, 8.97. Found: C, 53.62; H, 6.49; N, 9.11.

Example 1

Experiments were carried out under the following STD-NMR measuring conditions.
1. Samples
  (1) Protein: $^{15}$N-mSin3B [According to the method described in Example 1 in WO2006/030722, $^{15}$N-mSin3B (the PAH1 domain of mSin3B (a.a. 28-107) labeled with $^{15}$N) was prepared.]
  (2) Ligands: 3,5-dimethylpeperidyl 3-methyl-4-nitrophenyl ketone (purchased from SPECS); 1-[4-(difluoromethoxy)phenyl]-2-(3,5-dimethylpiperidyl)ethan-1-one (purchased from Enamine); 3,5-dimethylpiperidyl 4-chloro-3-nitrophenyl ketone (purchased from Vitas-M Laboratory, LTD.), 3,5-dimethylpiperidyl 4-fluorophenyl ketone (purchased from Vitas-M Laboratory, LTD.), 2-(2,6-dimethylmorpholin-4-yl)-N-(2-chloro-4-fluorophenyl)acetamide (purchased from Enamine); 1-benzoyl-3,5-dimethylpiperidine (NCR6) (prepared in Preparation Example 5); 3,5-dimethyl-1-(3-methyl-4-nitrobenzyl)piperidine (NCR7) (prepared in Preparation Example 21); 3,5-dimethyl-1-(4-chlorobenzoyl)piperidine (NCR11) (prepared in Preparation Example 7); 3-methyl-4-nitro-N,N-dipropylbenzamide (NCR13) (prepared in Preparation Example 11); N,N-diisobutyl-3-methyl-4-nitrobenzamide (NCR14) (prepared in Preparation Example 12); N,N-diisopropyl-3-methyl-4-nitrobenzamide (NCR15) (prepared in Preparation Example 13)

2. Sample Preparation
  (1) Samples necessary for measurement were prepared in 500 µl samples.
  (2) The concentration of the protein was 10 µM, and the concentration of the ligands was 400 µM.
  (3) As a solvent, 100 mM phosphate buffer (pH 7.2) (5% d-DMSO) was used. The protein and the ligand were mixed therein.
3. NMR Measuring Conditions
1H-STD; number of scans: 4; measurement time: 2 minutes
4. NMR Apparatus
Bruker AVANCE 600 MHz (cryo-probe), Bruker AVANCE 700 MHz (cryo-probe)

The results are shown in FIGS. 1 to 11. Since STD spectra were observed with the 11 ligands used in the measurement, it was judged that these ligands interact with the protein.

Example 2

Cell growth effects were examined on 3,5-dimethylpiperidyl 3-methyl-4-nitrophenyl ketone (compound 155) and 1-[4-(difluoromethoxy)phenyl]-2-(3,5-dimethylpiperidyl) ethan-1-one (compound A28) (MTT assay using a human medulloblastoma cell strain).
Materials and Methods
Compounds: 3,5-dimethylpiperidyl 3-methyl-4-nitrophenyl ketone (compound 155) (purchased from SPECS); 1-[4-(difluoromethoxy)phenyl]-2-(3,5-dimethylpiperidyl)ethan-1-one (compound A28) (purchased from Enamine)
Cell: DAOY (human medulloblastoma cell strain) (provided by Kanno, Department of Neurosurgery, School of Medicine, Yokohama City University)
Medium: DMEM (High Glucose, Nacalai Tesque)
Reagent for cell counting: MTT cell counting kit (Nacalai Tesque) MTT Assay: (operations)
Day −1: DAOY was plated on three 96-well plates at 5×10$^3$ cells/well. These three plates were for use on day 0, day 1 and day 3, respectively. As a medium, 10% FBS-containing DMEM was used.
Day 0: MTT assay was carried out using the plate for day 0 to measure the activity at the basal cell count. With respect to the plates for day 1 and day 3, the compound was added to give a concentration of 100 µg/ml (as controls, DMEM alone and DMEM containing DMSO (solvent) were used).
Specifically, the compound-containing DMEM was prepared in advance, and the compound was added to the plate through medium exchange. At this time, FBS concentration was lowered to 5% in order to prevent the masking of the compound's effect due to excessive growth signals.
Day 1: MTT assay was carried out using the plate for day 1.
Day 3: MTT assay was carried out using the plate for day 3.
Data Analysis: Relative growths on day 1 and day 3 were calculated, with the average of MTT activities (Ab 570 nm) on day 0 in the rows of wells for addition of the respective compounds being taken, as 100.

Each experiment was performed in quadruple and each run was repeated three times. Relative values based on the values of day 0 were used to calculate data for n=12 wells and statistical tests were performed.
Test was by t-test between the cell count with DMEM alone and the cell count with the compound or DMSO.
MIT Assay: A technique for cell counting using the respiratory activity of mitochondria as an indicator. When the respiratory activity is high (the value at Ab 570 nm is high), it can be interpreted that the cell count is large.

Results
The results are summarized in the following Table.

TABLE 43

| | Relative Growth | | | |
|---|---|---|---|---|
| | Compound 155 | A28 | DMEM + DMSO | DMEM only |
| Day 0 | 100.00 ± 5.08 | 100.00 ± 6.56 | 100.00 ± 3.76 | 100.00 ± 5.45 |
| Day 1 | 123.16 ± 10.03 | 233.28 ± 1.69 | 158.33 ± 15.78 | 146.33 ± 11.22 |
| Day 3 | 105.07 ± 17.53 | 90.17 ± 171 | 297.78 ± 15.42 | 282.09 ± 15.63 |

| Test (Two Sample t-Test) (Compound) or (DMEM + DMSO) vs (DMEM only) | | | |
|---|---|---|---|
| | Compound 155 | A28 | DMEM + DMSO |
| Day 1 | 0.12215 | 5.90E−08 | 0.52411 |
| Day 3 | 7.71E−08 | 1.23E−11 | 0.46362 |

Compound A28: This compound showed a transient, abnormal cell growth on Day 1. When cells were observed on day 3, they appeared morphologically dead. It is believed that cells finally die from depletion of nutrients in the medium or the like as a result of abnormally accelerated growth. The phenotype of this compound was very distinct even without performing MTT assay. Compound 155: Cell growth was inhibited on both day 1 and day 3. It seems that this compound is the most promising as a drug candidate.

Example 3

Materials and Methods

Compounds: No. 5, No. 15, No. 23, NCR 6, NCR 7, NCR 11, NCR 13, NCR 14, NCR 15
Cell: DAOY (human medulloblastoma cell strain)
Medium: DMEM (High Glucose, Nacalai Tesque)
Reagent for cell counting: MTT cell counting kit (Nacalai Tesque) *Hereinafter, referred to as MTT assay.
Operations
Day −1:
DAOY was plated on three 96-well plates at $5 \times 10^3$ cells/well. These three plates were for use on day 0, day 1 and day 3, respectively. As a medium, 10% FBS-containing DMEM was used.
Day 0:
The medium in the plate for day 0 was exchanged with 5% FBS-containing DMEM, and cells were cultured therein for 30 minutes. Then, MTT assay was carried out to measure the activity at the basal cell count.
With respect to the plates for day 1 and day 3, the medium was exchanged with 5% FBS-containing medium, and the compound was added simultaneously at this time (as a control, DMSO (the solvent) alone was added).
Day 1:
MTT assay was carried out using the plate for day 1.
Day 3:
MTT assay was carried out using the plate for day 3.
Data Analysis:
Relative growths on day 1 and day 3 were calculated, with the average of MTT activities (Ab 570 nm) on day in the rows of wells for the respective compounds being taken as 100. Each experiment was performed in quadruple.

Figure 12:
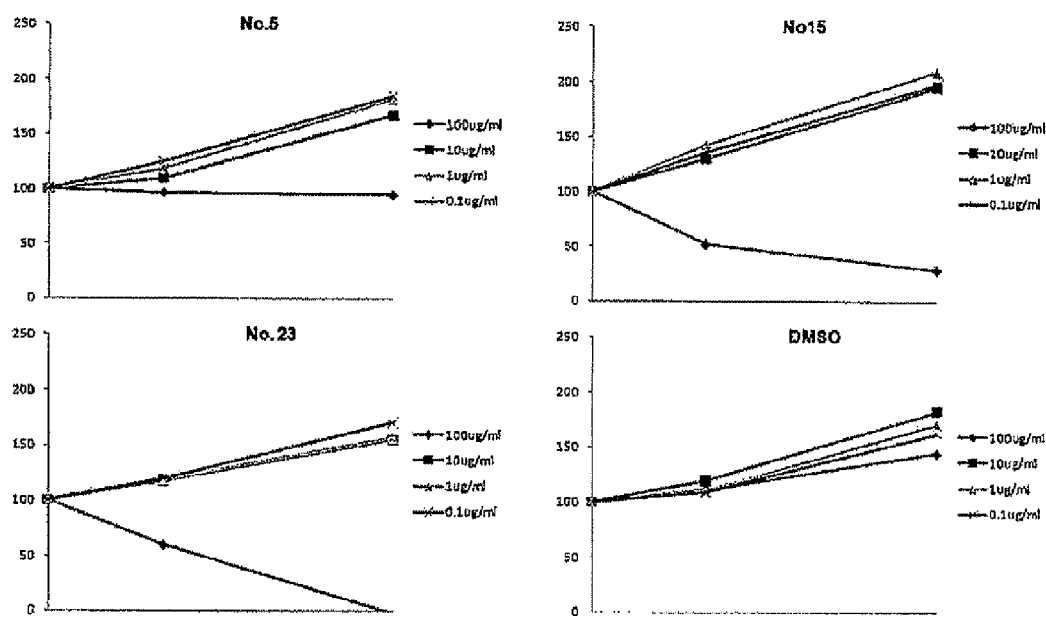
FIG. 12 shows the dose dependency of compounds 5, 15 and 23 (100 μg/ml) in their growth inhibition activities against human medulloblastoma cells.
Figure 13:
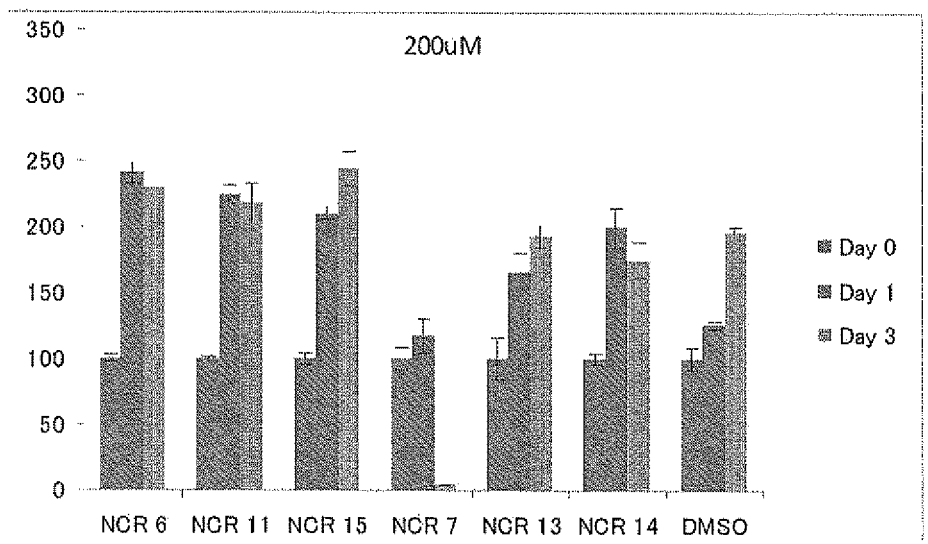
FIG. 13 shows the growth inhibition activities of compounds NCR6, 7, 11, 13, 14 and 15 (200 μM and 20 μM) against human medulloblastoma cells.
Figure 13:
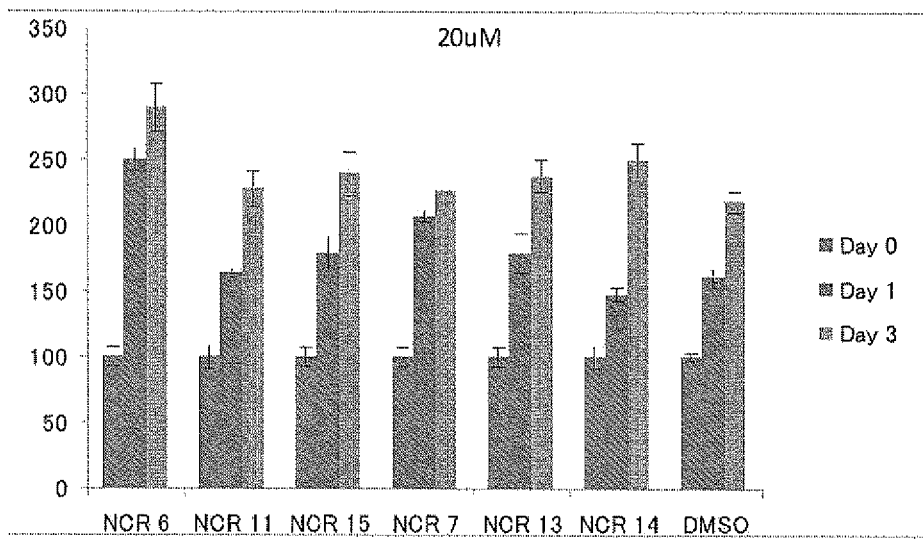

Statistical test was performed by compound-treated cells and DMSO-treated cells.
Results
Compounds No. 5, No. 15 and No. 23 were added to cells at final concentrations of 100 µg/ml, 10 µg/ml, 1 µg/ml and 0.1 µg/ml, and the relative growth rates of the cells were examined. With any of the compounds, measured values of MTT assay showed a significant decrease, compared to DMSO-added cells, when the concentration was 100 µg/ml. With compound No. 5, measured values of MTT assay did not change greatly during the experiment period; therefore, this compound is likely to have an inhibitory action on cell growth. On the other hand, with compounds No. 15 and No. 23, almost all cells had died three days after their addition. Therefore, it was suggested that these compounds have cytotoxicity (FIG. 12).
Compounds NCR 6, NCR 7, NCR 11, NCR 13, NCR 14 and NCR 15 were added at a final concentration of 200 µM/ml or 20 µM/ml. When NCR 7 was added at 200 µM/ml, cytotoxicity was observed (FIG. 13).

Example 4

Evaluation of Efficacies of mSin3B Compounds on Chronic Pain Model Animal

A neuropathic pain model was created by partial sciatic nerve ligation using 6-10 week old C57BL male mice (20-25 g) (TEXAM Corporation) (Inoue et al., Nature Medicine, 10: 712-718, 2004). mSin3B compounds were dissolved in 100% DMSO. Immediately before administration, the compound was diluted with artificial cerebrospinal fluid (DMSO final concentration: 0.5%) and administered into the spinal subarachnoid space (i.t.) at 0.5 nmol/5 µl. For control group, DMSO (0.5%) diluted with artificial cerebrospinal fluid was administered as a vehicle. In an experiment involving systemic administration of mSin3B compounds, the compound was diluted with physiological saline (DMSO final concentration: 10%) immediately before administration and administered at 5 mg/kg intraperitoneally (i.p.). For the control group in this experiment, DMSO (10%) diluted with physiological saline was administered as a vehicle. On the other hand, morphine was dissolved in physiological saline and administered intraplantarly (i.pl.) at 30 nmol/20 µl. ACU values from 10 to 60 minutes after morphine administration were calculated to evaluate of the analgesic effect of morphine. For behavioral analysis concerning pain, (1) "electrical stimulation-induced paw withdrawal (EPW) test" (Matsumoto et al., J Pharmacol Exp Ther, 318:735-740, 2006; Ueda, Mol Pain, 4:11, 2008, REVIEW) to evaluate a pain threshold in response to C-fiber specific electrical stimulation (5 Hz) and (2) "thermal paw withdrawal test" (Inoue et al., Nature Medicine, 10: 712-718, 2004) to evaluate a pain threshold in response to thermal stimulation were used. For expression analysis of a group of pain-associated genes ($Na_v$ 1.8 and MOP), the cell soma of primary sensory neuron (dorsal root ganglia) after nerve injury was used; evaluation was made by quantitative real time PCR.
mSin3B compounds: 3,5-dimethylpiperidyl 3-methyl-4-nitrophenyl ketone (compound 155), 1-[4-(difluoromethoxy)phenyl]-2-(3,5-dimethylpiperidyl)ethan-1-one (compound A28), N-[(4-fluorophenyl)methyl]-N'-(3-methylbutyl)butane-1,4-diamide (compound 106)

Results and Discussion

Experiment (1)

Figure 14:
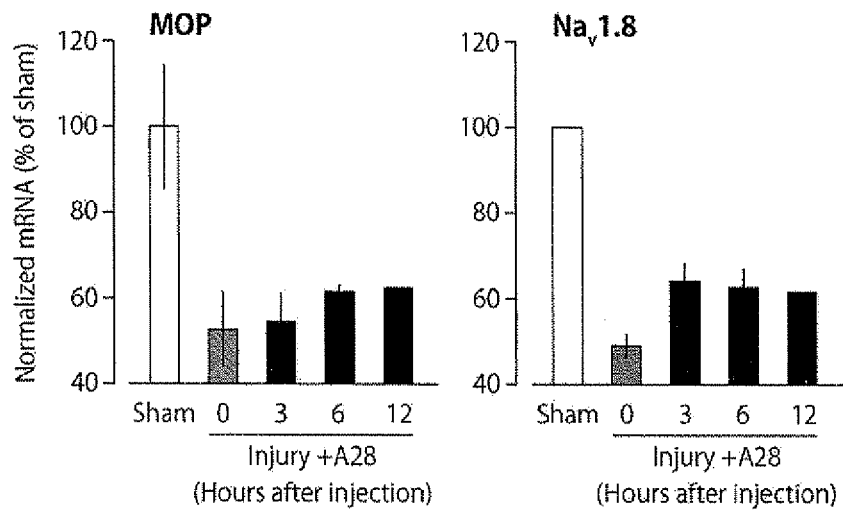
FIG. 14 shows the results of analysis of mRNA levels of pain-associated genes ($Na_v1.8$ and MOP) in dorsal root ganglia at 3, 6 and 12 hours after a single administration of mSin3B compound (A28) 3 days after nerve injury (n=3).

Three days after nerve injury, mSin3B compound (A28) was administered once, followed by analysis of mRNA levels of a group of pain-associated genes (Na$_v$1.8 and MOP) in dorsal root ganglia at 3, 6 and 12 hours after the administration (n=3 for each analysis). As a result, a tendency was observed that the lowering of expression of Na$_v$1.8 and MOP after nerve injury is recovered by about 10-15% by treatment with A28 (0.5 nmol i.t.) (FIG. 14). It was suggested that about 3-6 hours are needed for the effect to appear.

Experiment (2)

Figure 15:
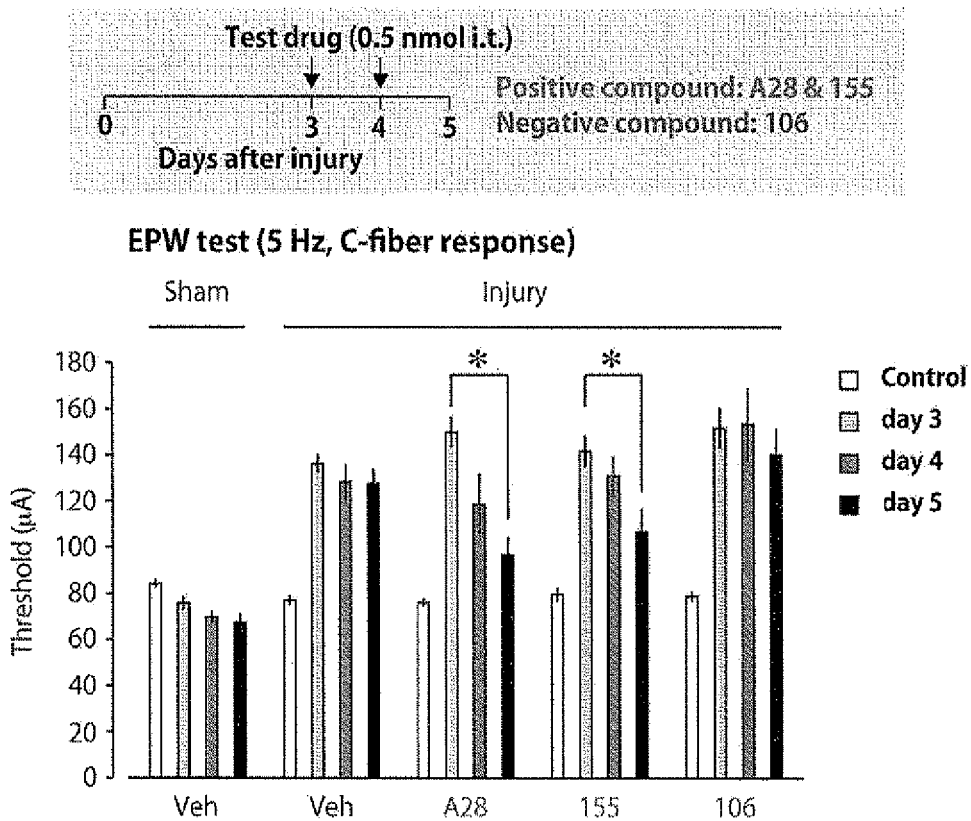
FIG. 15 shows the results of evaluation with EPW test of the efficacies of mSin3B compounds (A28, 155 and 106 (NC)) (0.5 nmol i.t.) against hypoesthesia after nerve injury.

Subsequently, the efficacies of mSin3B compounds (A28, 155, 106 (NC)) on hypoesthesia after nerve injury were evaluated by EPW test. Three days after nerve injury, increase of pain threshold in response to C-fiber stimulation (i.e., hypoesthesia) was observed in injury groups (injury-veh group: n=5; injury-A28 group: n=6; injury-155 group: n=6; injury-106 group: n=6) compared to control group (sham-veh group: n=6). Further, mSin3B compounds (A28, 155, 106 (NC)) or vehicle was administered once per day after behavioral analysis. As a result, a tendency of recovery from hypoesthesia was observed starting 4 days after nerve injury (1 day after the start of administration) in injury-A28 group and injury-155 group; this tendency became more marked 5 days after nerve injury (2 days after the start of administration) (FIG. 15). As a result of statistical analysis, a significant difference was recognized between pain threshold values at 3 days after nerve injury and 5 days after nerve injury in injury-A28 group and injury-155 group. On the other hand, no effect on pain threshold was recognized in injury-106 group.

Experiment (3)

Figure 16:
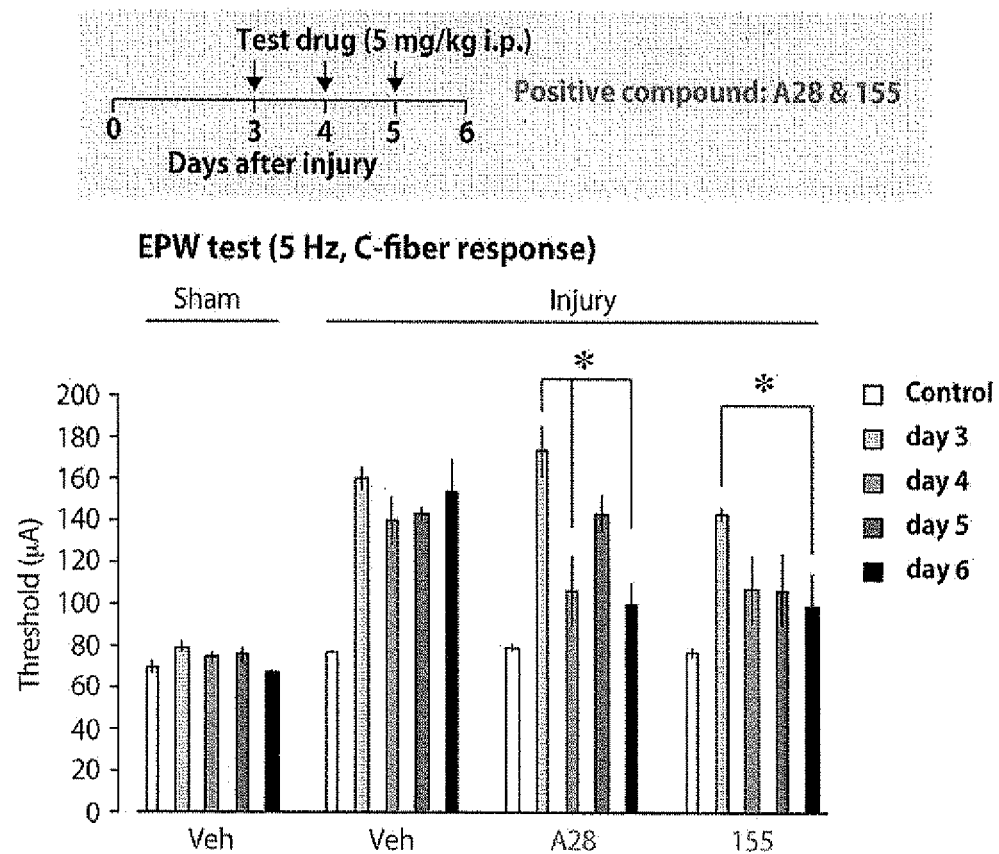
FIG. 16 shows the results of analysis of the effects of mSin3B compounds (A28 and 155) on pain threshold when they were systemically (intraperitoneally) administered (5 mg/kg) consecutively on day 3, 4 and 5 after injury.

Subsequently, in consideration of clinical indications, mSin3B compound (A28 or 155) was administered systemically (intraperitoneally) (5 mg/kg) and consecutively for 3, 4 and 5 days after nerve injury, followed by evaluation of the effect on pain threshold. Pain tests were performed prior to administration of the compound. As a result, time-dependent recovery from hypoesthesia was observed in both A28- and 155-administered groups (n=3 for each group) relative to the hypoesthesia at 3 days after nerve injury (control group) (FIG. 16).

Experiment (4)

Figure 17:
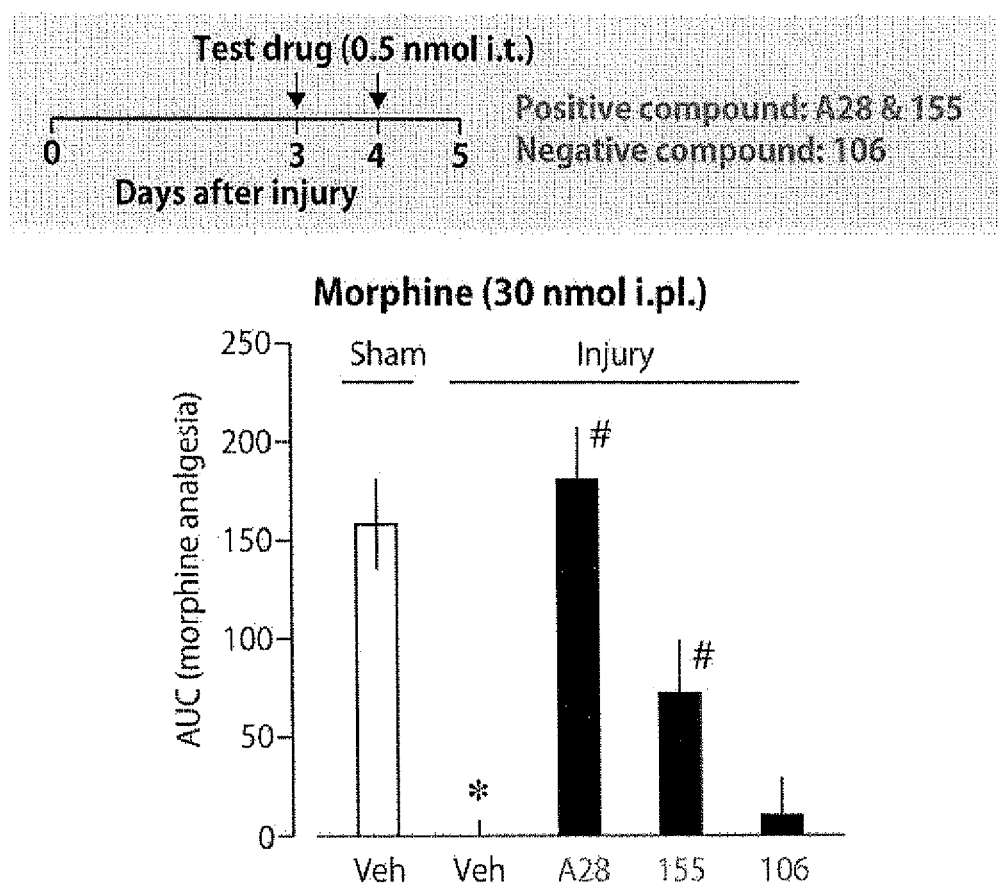
FIG. 17 shows the results of evaluation with thermal paw withdrawal test of the efficacies of mSin3B compounds (A28, 155 and 106 (NC)) (0.5 nmol i.t.) against morphine resistance after nerve injury.

Further, efficacies of mSinB3 compounds (A28, 155, 106 (NC)) on morphine resistance after nerve injury were evaluated using thermal paw withdrawal test. Administration of mSin3B compounds was started 3 days after nerve injury, and after 5 days after nerve injury 2 days after the start of administration, peripheral morphine (30 nmol i.pl.) analgesia was analyzed (sham-veh group: n=6; injury-veh group: n=5; injury-A28 group: n=6; injury-155 group: n=6; injury-106 group: n=3). The results revealed that, compared to sham-veh group, effect of morphine analgesia disappeared in injury-veh group, but morphine analgesia almost equivalent to that in sham-veh group was obtained in injury-A28 group. In injury-155 group, significant recovery of morphine analgesia was recognized. On the other hand, morphine analgesia was hardly recognized in injury-106 group. These results are shown in FIG. 17.

Figure 18:
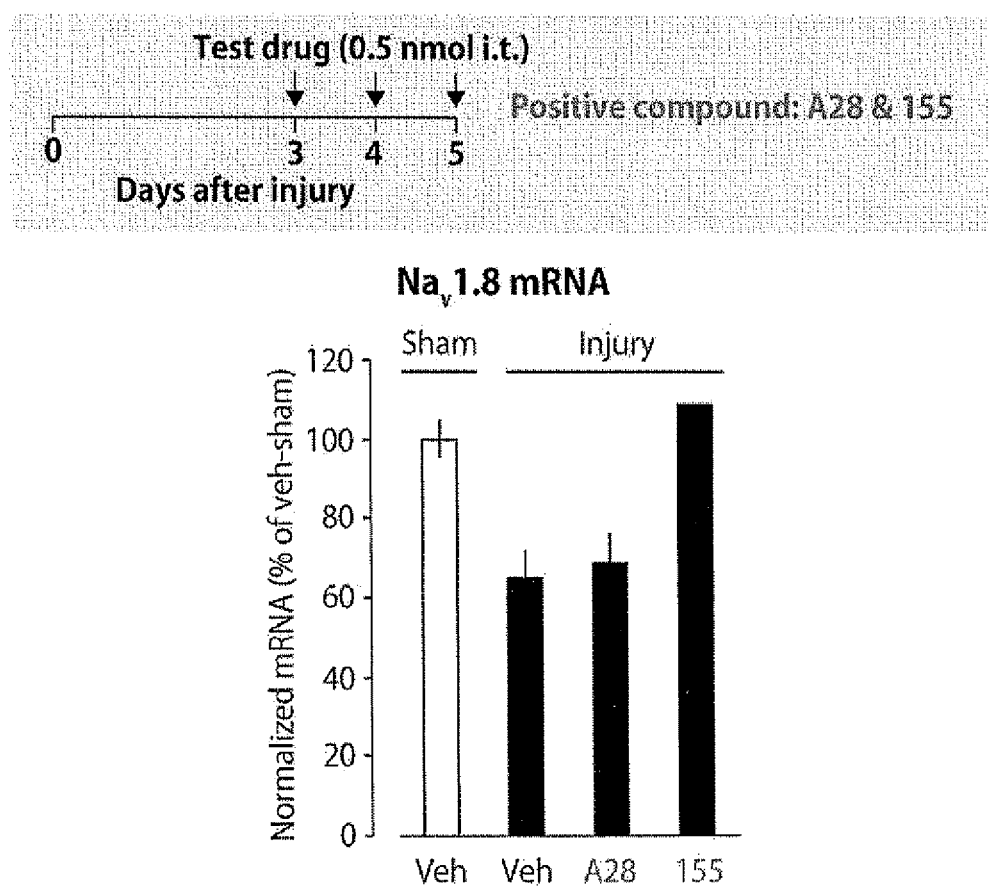
FIG. 18 shows the results of evaluation by a quantitative real time method of mRNA levels of $Na_v1.8$ in dorsal root ganglia after administration of mSin3B compounds (A28 and 155) (0.5 nmol i.t.).

Experiment (5)

mRNA levels of Na$_v$1.8 in dorsal root ganglia after administration of mSin3B compound (A28 or 155) (0.5 nmol i.t.) were evaluated by a quantitative real time method, revealing that compound 155 exhibited a remarkable inhibitory effect on the lowering of expression of Na$_v$1.8 due to nerve injury; however, A28 did not exhibit a significant change (sham-veh group: n=3; injury-veh group: n=3; injury-A28 group: n=3; injury-155 group: n=2) (FIG. 18).

All the publications, patents and patent applications cited herein are incorporated herein by reference in their entirety.

INDUSTRIAL APPLICABILITY

A substance capable of binding to the PAH1 domain of mSin3B (e.g., a compound represented by formula (I), pharmacologically acceptable salt thereof, or pharmacologically acceptable ester thereof) may be used as a medicine, especially as a prophylactic and/or a therapeutic for diseases associated with abnormal expression of neural restrictive silencer factor NRSF/REST or abnormal expression of genes targeted by NRSF/REST.

PRIOR ART LITERATURE

Patent Documents

Patent Document No. 1: WO2006/030722 International Publication

Non-Patent Documents

Non-Patent Document No. 1: Bahn S et al.: *Lancet*, 359, 310-315 (2002)

Non-Patent Document No. 2: Okazaki T et al.: *Neurobiol Aging*, 16, 883-894 (1995)

Non-Patent Document No. 3: Lawinger P et al.: *Nature Med.*, 7, 826-831 (2000)

Non-Patent Document No. 4: Zuccato C et al.: *Nature Genetics*, 35, 76-83 (2003)

Non-Patent Document No. 5: Naruse Y et al.: *Proc. Natl Acad. Sci. USA*, 96, 13691-13696 (1999)

Non-Patent Document No. 6: *J. Mol. Biol.*, 354, 903-915 (2005)

Non-Patent Document No. 7: Uchida et al., *Neuroscience* 166, 1-4, 2010

Non-Patent Document No. 8: Uchida et al., *J Neurosci* 30, 4806-4814, 2010

Non-Patent Document No. 9: Ueda, *Mol Pain* 4:11, 2008, Review

Non-Patent Document No. 10: Ueda, *Pharmacol Ther* 109: 57-77, 2006, Review

The invention claimed is:

1. A method of treating a disease associated with abnormal expression of neural restrictive silencer factor NRSF/REST or abnormal expression of genes targeted by NRSF/REST, comprising administering to a subject a pharmacologically effective amount of a substance capable of binding to the PAH1 domain of mSin3B, wherein the disease is neuropathic pain and the substance is a compound represented by A28 or 155 or a pharmacological acceptable salt or ester thereof, where A28 and 155 are:

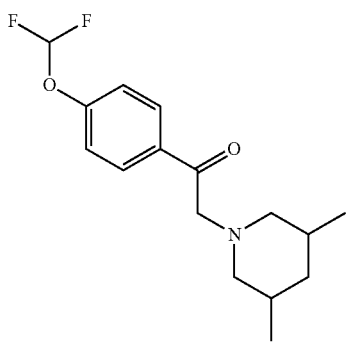

A28

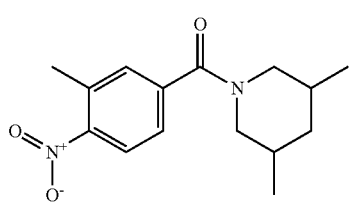

155

2. A method of preparing and administering a substance capable of binding to the PAH1 domain of mSin3B, comprising:

preparing a prophylactic and/or a therapeutic substance that binds to the PAH1 domain of mSin3B for a disease associated with abnormal expression of neural restrictive silencer factor NRSF/REST or abnormal expression of genes targeted by NRSF/REST; and administering to a subject the substance that binds to the PAH1 domain of mSin3B, wherein the disease is neuropathic pain and the substance is a compound represented by A28 or 155 or a pharmacological acceptable salt or ester thereof, where A28 and 155 are:

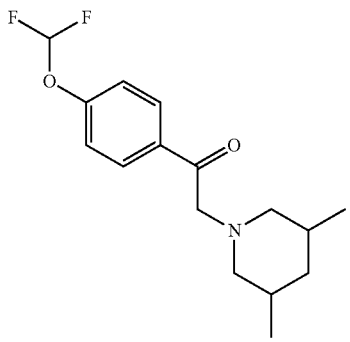

A28

-continued

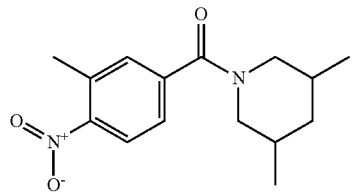

155

3. A method of treatment with a substance capable of binding to the PAH1 domain of mSin3B, comprising:

administering to a subject a substance capable of binding to the PAH1 domain of mSin3B to treat a disease associated with abnormal expression of neural restrictive silencer factor NRSF/REST or abnormal expression of genes targeted by NRSF/REST, wherein the disease is neuropathic pain and the substance is a compound represented by A28 or 155 or a pharmacological acceptable salt or ester thereof, where A28 and 155 are:

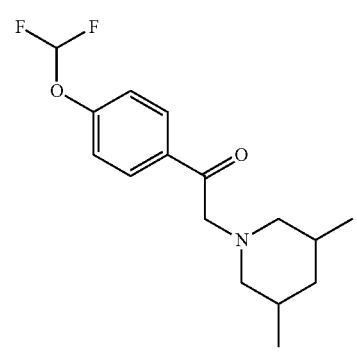

A28

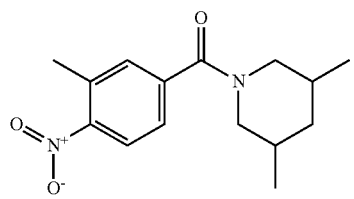

155

* * * * *